US006444823B1

(12) United States Patent
Biedermann et al.

(10) Patent No.: US 6,444,823 B1
(45) Date of Patent: *Sep. 3, 2002

(54) PYRIDYL ALKANE ACID AMIDES AS CYTOSTATICS AND IMMUNOSUPPRESSIVES

(75) Inventors: Elfi Biedermann, Vaterstetten; Max Hasmann, Neuried; Roland Löser, Feldafing; Benno Rattel, Munich; Friedemann Reiter, Putzbrunn; Barbara Schein, Neufahrn; Klaus Seibel, Grä felfing; Klaus Vogt, Munich, all of (DE)

(73) Assignee: Klinge Pharma GmbH, Munich (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/216,075

(22) Filed: Dec. 18, 1998

Related U.S. Application Data

(63) Continuation of application No. PCT/EP97/03243, filed on Jun. 20, 1997.

(30) Foreign Application Priority Data

Jun. 20, 1996 (DE) .................. DE 196 24 704

(51) Int. Cl.⁷ .................. C07D 401/12; C07D 401/08; A61K 31/444
(52) U.S. Cl. ............... 546/208; 546/207; 514/318; 514/317
(58) Field of Search ............... 546/290, 186, 546/193, 208, 207; 514/320, 318

(56) References Cited

U.S. PATENT DOCUMENTS

| 4,283,541 A | | 8/1981 | Shroff et al. ............ 546/336 |
| 5,169,856 A | * | 12/1992 | Goto et al. ............ 514/314 |
| 5,260,323 A | * | 11/1993 | Baader et al. ............ 514/356 |
| 5,326,772 A | * | 7/1994 | Klemm et al. ............ 514/318 |

FOREIGN PATENT DOCUMENTS

| CA | 2085954 | * | 6/1993 | |
| DE | 40 20 570 A1 | | 1/1992 | ......... C07D/213/89 |
| EP | 048045 | * | 3/1982 | |
| EP | 0 210 782 A2 | | 2/1987 | ......... C07D/213/56 |
| EP | 271023 | * | 6/1988 | |
| EP | 0 330 026 A1 | | 2/1989 | ......... C07D/211/26 |
| EP | 0 330 026 B1 | | 2/1989 | |
| EP | 0 343 307 A1 | | 11/1989 | ......... C07D/211/58 |
| EP | 416581 | * | 3/1991 | |
| EP | 471236 | * | 2/1992 | |
| EP | 479601 | * | 4/1992 | |
| EP | 522606 | * | 1/1993 | |
| EP | 0 530 444 A1 | | 3/1993 | ......... C07D/213/82 |
| EP | 0 548 883 A1 | | 6/1993 | ......... C07D/231/89 |
| EP | 512902 | * | 4/1994 | |
| EP | 428434 | * | 5/1994 | |
| GB | 2304714 | * | 11/1998 | |
| JP | 57136518 | * | 8/1982 | |
| JP | 63179869 | * | 7/1988 | |
| WO | WO89/07443 | | 8/1989 | |
| WO | WO 91/15484 A1 | | 10/1991 | ......... C07D/401/06 |
| WO | WO 91/15485 A1 | | 10/1991 | ......... C07D/401/12 |
| WO | WO93/14113 | | 7/1993 | |
| WO | WO 95/10514 A1 | | 4/1995 | ......... C07D/401/04 |
| WO | WO95/10516 | | 4/1995 | |
| WO | WO95/24894 | | 9/1995 | |
| WO | WO93/13083 | | 4/1997 | |

OTHER PUBLICATIONS

Rote Liste. 1997, (2 pages).

Chemical Abstracts, 15–Immunochemistry. vol. 124, No. 13, 1996, (1 page).

Chemical Abstracts. vol. 115, 1991, (1 p.).

Nishikawa et al., "Acrylamide Derivatives as Antiallergic Agents." Chem. Pharm. Bull. 37, No. 1, 1989,(6 pages).

W. C. J. Ross, "The Preparation of Some 4–Substituted Nicotinic Acids and Nicotinamides." J. Chem. Soc. 1966, (6pages).

R. Fischer, "Allgemeine Pathologie und Pathologische Anatomie." Published before filing date, (7 pages).

Nishikawa et al., "Acrylamide Derivatives as Antiallergic Agents. 2. Synthesis and Structure–Activity Relationships of N–[4–[4–(Diphenylmethyl) –1–piperazinyl]butyl] –3–(3–pyridyl) acrylamides" J. Med. Chem. 1989, 32, 583–593.*

Ishihara et al., "Central Cholinergeic Agents. II. Synthesis and Acetylcholinesterase Inhibitory Activities of N–[w–[N–Alkyl–N–(phenylmethyl) amino]alkyl]–3–arylpropenamides" Chem. Pharm. Bull. 39 (12) 3236–3234 (1991).

* cited by examiner

Primary Examiner—Alan L. Rotman
Assistant Examiner—Rita Desai
(74) Attorney, Agent, or Firm—Fitch, Even, Tabin & Flannery

(57) ABSTRACT

The invention relates to new pyridyl alkane acid amides according to general formula (I) as well as methods for their production, medicaments containing these compounds as well as their medical use, especially in the treatment of tumors or for immunosuppression.

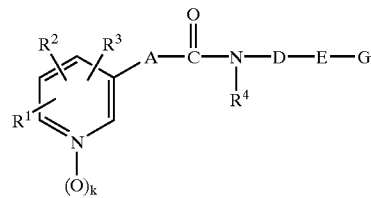

15 Claims, No Drawings

PYRIDYL ALKANE ACID AMIDES AS CYTOSTATICS AND IMMUNOSUPPRESSIVES

This application is a continuation of PCT/EP97/03243, filed Jun. 20, 1997.

The invention relates to new pyridine compounds, methods for their production, medicaments containing these compounds as well as their use, especially in the treatment of tumor conditions and/or as cytostatic agents or as immunosuppressive agents.

A strong need exists for the enrichment of cytostatic therapy to provide pharmaceuticals and/or medicaments which not only possess a strong activity, but also exert diminished side effects in comparison to many classical cancerostatic agents, whereby treatment of a broad as possible spectrum of tumors should be made accessible. Furthermore, effective cytostatic agents for an efficient therapy should be made available. Active ingredients of this type should also be exceptionally suitable in the mentioned indications for a combination therapy, be it in connection with other cytostatic agents or with radiation (for example X-rays, radioactive elements, such as cobalt, or linear accelerator, etc.), with operative procedures, heat treatment, etc.

In this connection, a strong need also exists to enrich tumor therapy with new compounds for overcoming or preventing resistances for example.

This object was successfully solved in a completely suprising manner by raking available the pyridyl alkane acid amide derivatives defined below.

It was known that various pyridine compounds substituted in a specific manner have pharmacologically useful properties which lie however in completely different indication areas.

Thus, ω-pyridyl alkane and/or alkene amides with anti-allergic activity are described in EP 0 210 782 which are referred to as having a 5-lipoxygenase-inhibiting and antihistamine action, wherein the amide components of these compounds contain a piperizine or homopiperizine ring and the pyridine ring can be linked together in the 2-, 3- or 4-position. JP 63,179,869 describes further pyridyl amides, ωn-pyridyl alkane and alkene amides as anti-allergic effective substances containing a substituted piperidine ring in the amine component. Such compounds with the same properties are mentioned in Chem. Pharm. Bull 37, 100–105 (1989) and in J. Med. Chem. 1989, 583–593.

Pyridyl ureas, pyridyl thioureas and pyridyl carbonamides, wherein the amide portion is bound over an aryl substituted alkyl chain with a piperidine ring or piprazine ring, are described for example in EP-A-0 428 434 or in EP-A-0 512 902 as antagonists of the neurokinin receptor and subtance P. Furthermore, pyridyl(alkyl)carbonamides, pyridyl(alkyl)sulfonamides and analogous ureas, wherein the amide portion is bound over an alkyl chain with a piperidine ring are disclosed in EP-A-0 479 601 as active ingredients with anti-arrhythmic properties.

In WO 91/15 485, the production of pyridine-3,5-dicarboxylic acid esters and amides as well as their use for the treatment of tumor conditions is described. These compounds differ from the compounds according to the invention described below in very important structural features, for example by the dicarboxyl grouping on the pyridine ring or the absence of the hydrocarbon chain between the pyridine ring and the amide grouping. The compounds disclosed in WO 89/07 443 in the form of optically pure R(-)-Niguldipine and further analogous dihydropyridines with cytotoxic activity have larger structural differences. However, the compounds according to the invention unexpectedly possess a better activity and a wider spectrum of action despite the large structural differences.

Structurally closely related compounds are represented by the antagonists of the histimine-$H_1$-receptor generally described in EP-A-0 343 307 which constitute substituted piperidine derivatives. However, no particular 3-pyridyl substitutions derivatives are concretely described in this publication.

In view of this art, the finding that the compounds according to the general formula (I) defined below have activities which make them particularly suitable in an excellent manner for the therapy of tumor illnesses was completely unexpected. Equally unexpected was the pharmacological finding that the compounds according to the invention also possess immunosuppressive properties besides cytostatic activity.

Pharmacological test results as well as the concrete tumor indications and combination possibilities are detailed and illustrated in the last part of the description.

Therefore, subject-matter of the invention relates to compounds of formula (I)

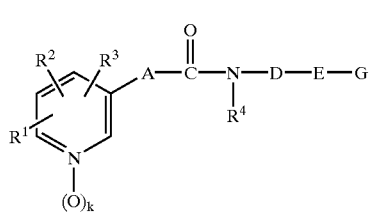

wherein $R^1$ is hydrogen, halogen, cyano, trifluoromethyl, hydroxy, benzyloxy, aminocarbonyl, carboxy, phenyl, phenoxy, phenylthio, pyridyloxy, pyridylthio, alkyl, especially $C_1$–$C_6$-alkyl, alkenyl, especially $C_3$–$C_6$-alkenyl, alkinyl, especially $C_3$–$C_6$-alkinyl, hydroxyalkyl, especially $C_1$–$C_6$-hydroxyalkyl, alkoxy, especially $C_1$–$C_6$-alkoxy, alkenyloxy, especially $C_3$–$C_6$-alkenyloxy, alkinyloxy, especially $C_3$–$C_6$-alkinyloxy, alkanoyloxy, especially $C_1$–$C_7$-alkanoyloxy, alkoxycarbonyloxy, especially $C_2$–$C_7$-alkoxycarbonyloxy, alkylthio, especially $C_1$–$C_6$-alkylthio, alkenylthio, especially $C_3$–$C_6$-alkenylthio, alkinylthio, especially $C_3$–$C_6$-alkinylthio, cycloalkyl, especially $C_3$–$C_8$-cycloalkyl, cycloalkyloxy, especially $C_3$–$C_8$-cycloalkyloxy, cycloalklylthio, especially $C_3$–$C_8$-cycloalkylthio, alkoxycarbonyl, especially $C_2$–$C_7$-alkoxycarbonyl, alkylaminocarbonyl, especially $C_2$–$C_7$-alkylaminocarbonyl, dialkylaminocarbonyl, especially $C_3$–$C_{13}$-dialkylaminocarbonyl, or $NR^5R^6$, wherein $R^5$ and $R^6$ are selected independently of each other from hydrogen, alkyl, especially $C_1$–$C_6$-alkyl, alkenyl, especially $C_3$–$C_6$-alkenyl and alkinyl, especially $C_3$–$C_6$-alkinyl, $R^2$ is hydrogen, halogen, cyano, hydroxy, trifluoromethyl, benzyloxy, alkyl, especially $C_1$–$C_6$-alkyl, alkoxy, especially $C_1$–$C_6$-alkoxy or alkanoyloxy, especially $C_1$–$C_7$-alkanoyloxy, wherein $R^1$ and $R^2$, if they are adjacent, optionally form a bridge which is selected from —$(CH_2)_4$—, —$(CH=CH)_2$— and —$CH_2O$—$CR^7R^8$—$O$—, wherein $R^7$ and R⁸ are, independently of each other, hydrogen or alkyl, especially $C_1$–$C_6$-alkyl, $R^3$ is hydrogen, halogen, alkyl, especially $C_1$–$C_6$-alkyl, trifluoromethyl or hydroxyalkyl, especially $C_1$–$C_6$-hydrohyalkyl and $R^4$ is hydrogen, hydroxy, benzyloxy, alkyl, especially $C_1$–$C_6$-alkyl, alkenyl, especially $C_3$–$C_6$-alkenyl, alkinyl, especially $C_3$–$C_6$-alkinyl, cycloalkyl, especially $C_3$–$C_6$-cycloalkyl or alkoxy, especially $C_1$–$C_6$-alkoxy, k is 0 or 1, A is alkylene, especially $C_1$–$C_6$-alkylene, which is optionally substituted once to three-fold by alkyl, especially $C_1$–$C_3$-alkyl, hydroxy, alkoxy, especially $C_1$–$C_3$-alkoxy, fluorine or phenyl, or 1,2-cyclopropylene or alkylene with at least two C-atoms, especially $C_1$–$C_6$-alkylene in which a methylene unit can be isosterically replaced by O, S, $NR^9$, CO, SO or $SO_2$, wherein the isosteric substitution, with the exception of =CO, cannot be adjacent to the amide group and wherein $R^9$ is selected from hydrogen, alkyl, especially $C_1$–$C_6$-alkyl, alkenyl, especially $C_3$–$C_6$-alkenyl, alkinyl, especially $C_3$–$C_6$-alkinyl, acyl, especially $C_1$–$C_6$-acyl or alkylsulfonyl, especially $C_1$–$C_6$-alkylsulfonyl, D is selected from alkylene, especially $C_1$–$C_{10}$-alkylene, optionally substituted once or twice by alkyl, especially $C_1$–$C_6$-alkyl, hydroxy, or alkoxy, especially $C_1$–$C_6$-alkoxy, alkenylene with at least two C-atoms, especially $C_2$–$C_{10}$-alkenylene, which is optionally substituted once or twice by alkyl, especially $C_1$–$C_6$-alkyl, hydroxy, or alkoxy, especially $C_1$–$C_6$-alkoxy, wherein the double bond can also be to ring E, alkinylene with at least three C-atoms, especially $C_3$–$C_{10}$-alkinylene, optionally substituted once or twice by alkyl, especially $C_1$–$C_6$-alkyl, hydroxy or alkoxy, especially $C_1$–$C_6$-alkoxy, and alkylene, especially $C_1$–$C_{10}$-alkylene, alkenylene with at least two C-atoms, especially $C_2$–$C_{10}$-alkenylene or alkinylene with at least three C-atoms, especially $C_3$–$C_{10}$-alkinylene, whereby one to three methylene units are each isosterically replaced by O, S, $NR^{10}$, CO, SO or $SO_2$ wherein $R^{10}$ has the same meaning as $R^9$ but is selected independently thereof, E is selected from

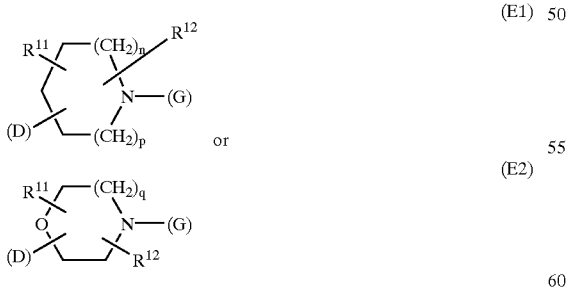

wherein the heterocyclic ring can also optionally have a double bond and n and p can be, independently of one another, 0, 1, 2 or 3, with the proviso that n+p≦4 and q is 2 or 3, $R^{11}$ is hydrogen, alkyl, especially $C_1$–$C_6$-alkyl, hydroxy, hydroxymethyl, carboxy or alkoxycarbonyl with at least two C-atoms, especially $C_2$–$C_7$-alkoxycarbonyl and $R^{12}$ is hydrogen, alkyl, especially $C_1$–$C_6$-alkyl or or an oxo group adjacent to the nitrogen atom, wherein $R^{11}$ and $R^{12}$ optionally together, form an alkylene bridge with 1, 2, 3, 4 or 5 C-atoms, especially a $C_1$–$C_3$-alkylene bridge under formation of a bicyclic ring system, G is selected from hydrogen, G1, G2, G3, G4 and G5, wherein G1 represents the residue

wherein r is an integer from 1 to 3 or 0 and s is 0 or 1, $R^{13}$ is selected from hydrogen, alkyl, especially $C_1$–$C_6$-alkyl, alkenyl with at least three C-atoms, especially $C_3$–$C_6$-alkenyl, alkinyl with at least three C-atoms, especially $C_3$–$C_6$-alkinyl, cycloalkyl with at least three C-atoms, especially $C_3$–$C_8$-cycloalkyl, saturated, five to seven membered heterocycles, which can contain one or two hetero-atoms from the group N and/or S and/or O, benzyl or phenyl, monocyclic aromatic five or six-membered heterocycles, which can contain one to three hetero-atoms from the group N and/or S and/or O and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic or a hydrated ring and either directly or over a methylene group, $R^{14}$ has the same meaning as $R^{13}$, but is selected independently thereof, $R^{15}$ is selected from hydrogen, hydroxy, methyl, benzyl, phenyl, monocyclic aromatic five- or six-membered heterocycles, which can contain one to three hetero-atoms selected from the group N and/or S and/or O and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 1 6 ring atoms and at least one aromatic ring, wherein one to three ring atoms can be selected from N and/or S and/or O and the linkage can occur either over an aromatic or a hydrated ring and either directly or over a methylene group, G2 is the residue

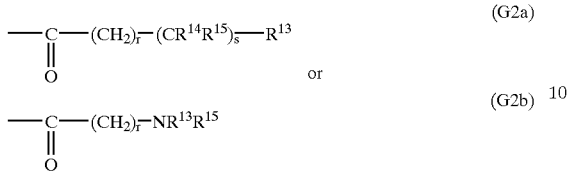

wherein the substituents $R^{13}$ and $R^{15}$ can have the above meaning or the grouping

—$NR^{13}R^{15}$ can also be a nitrogen heterocycle bound over the nitrogen atom, selected from saturated or unsaturated monocyclic, four- to eight-membered heterocycles, which, aside from the essential nitrogen atom, can optionally contain one or two further hetero-atoms selected from the group N and/or S and/or O, or saturated or unsaturated bi- or tricyclic, anellated or bridged heterocycles with 8 to 16 ring atoms, which, aside from the essential nitrogen atom, can optionally contain one or two further hetero-atoms selected from the group N and/or S and/or O, G3 is the residue —$SO_2$—$(CH_2)_r R^{13}$  (G3)

and
G4 is the residue

wherein
$Ar^1$ and $Ar^2$ are selected independently from one another from phenyl, pyridyl or naphthyl and G5 is the residue

—$COR^{16}$  (G5)

wherein
$R^{16}$ is selected from trifluoromethyl, alkoxy, especially $C_1$–$C_6$-alkoxy, alkenyloxy, especially $C_3$–$C_6$-alkenyloxy, or benzyloxy, wherein any aryl residues and/or aromatic ring systems in the substituents $R^1$, $R^2$, $R^4$, $R^{13}$, $R^{14}$, $R^{15}$, $R^{16}$, $Ar^1$ and $Ar^2$ and/or in the ring system —$NR^{13}R^{15}$ can be substituted independently from each other by one to three of the same or different residues which are selected from halogen, cyano, alkyl, especially $C_1$–$C_6$-alkyl, trifluoromethyl, cycloalkyl, especially $C_3$–$C_8$-cycloalkyl, phenyl, benzyl, hydroxy, alkoxy, especially $C_1$–$C_6$-alkoxy, alkoxy, substituted entirely or partially by fluorine, substituted alkoxy, especially $C_1$–$C_6$-alkoxy, benzyloxy, phenoxy, mercapto, alkylthio, especially $C_1$–$C_6$-alkylthio, carboxy, alkoxycarbonyl, especially $C_1$–$C_6$-alkoxycarbonyl, benzyloxycarbonyl, nitro, amino, monoalkylamino, especially mono-$C_1$–$C_6$-alkyl amino, dialkylamino, especially di-($C_1$–$C_6$-alkyl)-amino and methylenedioxy for two adjacent groups on the aromatic ring or ring system, wherein each of the residues alkyl, alkenyl, alkinyl, hydroxyalkyl, alkoxy, alkenyloxy, alkinyloxy, alkanoyloxy, alkoxycarbonyl, alkoxycarbonyloxy, alkylthio, alkenylthio, alkinylthio, alkylene, acyl, alkylsulfonyl, alkenylene, alkinylene, cycloalkyl, cycloalkyloxy, alkoxycarbonyl, alkylaminocarbonyl or dialkylaminocarbonyl of the substituents $R^1$ to $R^{14}$ can have 1 to 2 or 4, 6, 8, 10 or 12 C-atoms and/or 2 or 3 to 5, 7, 9, 11 or 13 and/or 15 C-atoms or 4, 5, 6, 7, 8, 9, 10, 11, 12, 13, 14 or 15 C-atoms depending on the structure, as well as stereoisomers and/or mixtures thereof and pharmacologically acceptable acid addition salts.

A preferred embodiment according to the invention relates to compounds of formula (I)

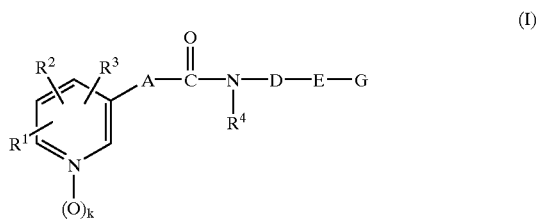

wherein
$R^1$ is a hydrogen, halogen, cyano, $C_1$–$C_6$-alkyl, $C_3$–$C_6$-alkenyl, $C_3$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, or $NR^5R^6$, wherein
$R^5$ and
$R^6$ are selected independently from each other from hydrogen, $C_1$–$C_6$-alkyl, $C_3$–$C_6$-alkenyl and $C_3$–$C_6$-alkinyl, $R^2$ is hydrogen, halogen, cyano, $C_1$–$C_6$-alkyl, trifluoromethyl, hydroxy, $C_1$–$C_6$-alkoxy, benzyloxy or $C_1$–$C_7$-alkanoyloxy, wherein $R^1$ and $R^2$, in case they are adjacent, optionally form a bridge which is selected from the bridge members —$(CH_2)_4$— and —$(CH=CH)_2$— and —$CH_2O$—$CR^7R^8$—O—, wherein
$R^7$ and
$R^8$ are, independently from each other, hydrogen or $C_1$–$C_6$-alkyl, $R^3$ is hydrogen, halogen, $C_1$–$C_6$-alkyl, trifluoromethyl or $C_1$–$C_6$-hydroxyalkyl and $R^4$ is hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy or benzyloxy, k is 0 or 1, A is $C_1$–$C_6$-alkylene, which is optionally substituted once to three-fold by $C_1$–$C_3$-alkyl, hydroxy, $C_1$–$C_3$-alkoxy, fluorine or phenyl, or 1,2-cyclopropylene or $C_2$–$C_6$-alkylene, wherein a methylene unit can be isosterically replaced by O, S, $NR^9$, CO, SO or $SO_2$, wherein the isosteric substitution, with the exception of =CO, cannot be adjacent to the amide group, and wherein R$^9$ is selected from hydrogen, $C_1$–$C_6$-alkyl, $C_3$–$C_6$-alkenyl, $C_3$–$C_6$-alkinyl, $C_1$–$C_6$-acyl or $C_1$–$C_6$-alkylsulfonyl, D is selected from $C_1$–$C_{10}$-alkylene, optionally substituted once or twice by $C_1$–$C_6$-alkyl, hydroxy, or $C_1$–$C_6$-alkoxy, $C_2$–$C_{10}$-alkenylene, which is optionally substituted once or twice by $C_1$–$C_6$-alkyl, hydroxy, or $C_1$–$C_6$-alkoxy, wherein the double bond can also be to ring E, $C_3$–$C_{10}$-alkinylene, optionally substituted once or twice by $C_1$–$C_6$-alkyl, hydroxy, or $C_1$–$C_6$-alkoxy, and $C_1$–$C_{10}$-alkylene, $C_2$–$C_{10}$-alkenylene or $C_3$–$C_{10}$-alkinylene, wherein one to three methylene units are each isosterically replaced by O, S, NR$^{10}$, CO, SO or SO$_2$, wherein R$^{10}$ has the same meaning as R$^9$, but is selected independently therefrom, E is selected from

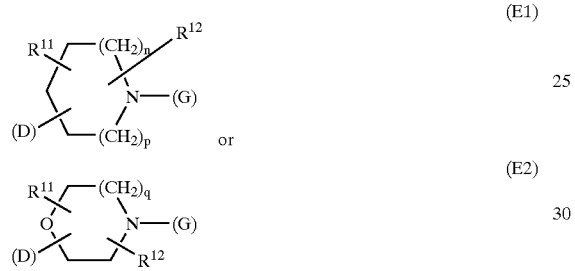

wherein the heterocyclic ring can optionally have a double bond and n and p can be, independently of each other, 0, 1, 2 or 3, with the proviso that n+p≦4 and q is 2 or 3, R$^{11}$ is hydrogen, $C_1$–$C_6$-alkyl, hydroxy, hydroxymethyl, carboxy or $C_2$–$C_7$-alkoxycarbonyl and R$^{12}$ hydrogen, $C_1$–$C_6$-alkyl or an oxo group adjacent to the nitrogen atom, wherein R$^{11}$ and R$^{12}$ optionally together form a $C_1$–$C_3$-alkylene bridge under formation of a bi-cyclic ring system, G is selected from hydrogen, G1, G2, G3, G4 and G5, wherein G1 represents the residue

wherein
r is an integer from 1 to 3 or 0 and
s is 0 or 1,
R$^{13}$ is selected from hydrogen, $C_1$–$C_6$-alkyl, $C_3$–$C_6$-alkenyl, $C_3$–$C_6$-alkinyl, $C_3$–$C_8$-cycloalkyl,
saturated, five- to seven-membered heterocycles, which can contain one or two hetero-atoms from the group N and/or S and/or O,
benzyl or phenyl,
monocyclic aromatic five or six-membered heterocycles, which can contain one to three hetero-atoms from the group N and/or S and/or O and are either bound directly or over a methylene group,
anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group,
anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group, R$^{14}$ has the same meaning as R$^{13}$, but is selected independently thereof, R$^{15}$ is selected from hydrogen, hydroxy, methyl, benzyl, phenyl,
monocyclic aromatic five- or six-membered heterocycles, which can contain one to three hetero-atoms selected from the group N and/or S and/or O and are either bound directly or over a methylene group,
anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group,
anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group, G2 is the residue

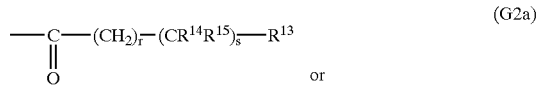

wherein the substituents R$^{13}$ and R$^{15}$ can have the above meaning or the grouping

can also be a nitrogen heterocycle bound over the nitrogen atom, selected from
saturated or unsaturated monocyclic, four- to eight-membered heterocycles, which, aside from the essential nitrogen atom, can optionally contain one or two further hetero-atoms selected from the group N and/or S and/or O, or
saturated or unsaturated bi- or tricyclic, anellated or bridged heterocycles with 8 to 16 ring atoms, which, aside from the essential nitrogen atom, can optionally contain one or two further hetero-atoms selected from the group N and/or S and/or O, G3 is the residue

and
G4 is the residue

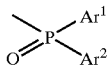
(G4)

wherein
Ar¹ and Ar² are selected independently from one another from phenyl, pyridyl or naphthyl and
G5 is the residue

—COR¹⁶   (G5)

wherein
R¹⁶ is selected from trifluoromethyl, $C_1$–$C_6$-alkoxy, $C_3$–$C_6$-alkenyloxy, or benzyloxy, and wherein
aromatic ring systems in the substituents R¹, R², R⁴, R¹³, R¹⁴, R¹⁵, R¹⁶, AR¹ and Ar² and/or in the ring system —NR¹³R¹⁵ can be substituted independently from each other by one to three of the same or different residues which are selected from halogen, cyano, $C_1$–$C_6$-alkyl, trifluoromethyl, $C_3$–$C_8$-Cycloalkyl, phenyl, benzyl, hydroxy, $C_1$–$C_6$-alkoxy, which can optionally be entirely or partially substituted by fluorine, benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino or di-($C_1$–$C_6$-alkyl)-amino and methylenedioxy for two adjacent groups on the aromatic ring or ring system,
stereoisomers thereof and/or mixtures thereof and pharmacologically acceptable
acid addition salts.

A further preferred embodiment of the invention constitutes compounds of the invention which are distinguished in that substituents R¹, R², R³, R⁴, R⁵, R⁶, R⁷, R⁸ R⁹, R¹⁰, R¹³, R¹⁴, R¹⁵ and R¹⁶ as well as A and D labelled therein have the following meaning in connection with the given substitutions according to this formula

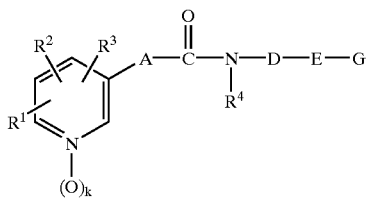
(I)

wherein
halogen is fluorine, chlorine, bromine or iodine,
$C_1$–$C_6$-alkyl can be straight chain or branched and is preferably a methyl-, ethyl-, propyl-, isopropyl-, butyl-, isobutyl-, sec-butyl-, tert-butyl-, cyclopropylmethyl-, pentyl-, isopentyl-, tert-pentyl-, neopentyl-, cyclopropylethyl-, cyclobutylmethyl- or a hexyl group,
alkylene is for example methylene, ethylene, propylene, tetramethylene, pentamethylene, hexamethylene, heptamethylene, octamethylene, nonamethylene or decamethylene,
$C_3$–$C_6$-alkenyl can be straight chain or branched and is preferably an allyl-, 2-butenyl-, 3-butenyl-, 2-methyl-2-propenyl-, 2-pentenyl-, 4-pentenyl-, 2-methyl-2-butenyl-, 3-methyl-2-butenyl-, 2-hexenyl-, 5-hexenyl-, 4-methyl-3-pentenyl- or 2,2-dimethyl-3-butenyl group,
alkenylene is for example ethenylene, propenylene, butenylene, pentenylene, hexenylene, hexathenylene, heptenylene, octenylene, nonenylene or decenylene,
$C_3$–$C_6$-alkinyl can be straight chain or branched and is preferably a propargyl-, 2-butinyl-, 3-butinyl-, 4-pentinyl-, 5-hexinyl- or 4-methyl-2-pentinyl group,
alkinylene is for example propinylene, butinylene, pentinylene, hexinylene, heptinylene, octinylene, noninylene or decinylene,
$C_3$–$C_8$-cycloalkyl is preferably cyclopropyl, cyclobutyl, cyclopentyl, cyclohexyl, cycloheptyl or cyclooctyl,
$C_1$–$C_6$-hydroxyalkyl contains a hydroxyl group in one of the above-named $C_1$–$C_6$-alkyl residues, especially in the form of the hydroxymethyl- and hydroxyethyl group, wherein
$C_1$–$C_6$-alkoxy, $C_3$–$C_6$-alkenyloxy, $C_3$–$C_6$-alkinyloxy each contain, aside from the oxygen atom, one of the $C_1$–$C_6$-alkyl-, $C_3$–$C_6$-alkenyl- and/or $C_3$–$C_6$-alkinyl groups named above and the methoxy-, ethoxy-, isopropoxy-, tert-butoxy-, allyloxy- and propargyloxy group are preferred and is to be understood as among $C_1$–$C_6$-alkoxy entirely or partially substituted with fluorine, for example difluormethoxy, trifluormethoxy or 2,2,2-trifluorethoxy,
$C_1$–$C_6$-alkylthio, $C_3$–$C_6$-alkenylthio, $C_3$–$C_6$-alkinylthio each contain, aside from the sulfur atom, one of the $C_1$–$C_6$-alkyl-, $C_3$–$C_6$-alkenyl- or $C_3$–$C_6$-alkinyl group named above, especially the methylthio-, ethylthio-, isopropylthio- and tert-butylthio groups,
$C_3$–$C_8$-cycloalkyloxy and $C_3$–$C_8$-cycloalkylthio are preferred as cyclopentyloxy- and cyclopentylthio- and/or cylohexyloxy- and cyclohexylthio groups,
$C_1$–$C_7$-alkanoyloxy groups contain, aside from the oxygen atom, an aliphatic acyl residue with 1 to 7 carbon atoms, especially the acetoxy-, propionyloxy- and pivaloyloxy group,
$C_2$–$C_7$-alkoxycarbonyl groups contain, aside from the carbonyl group, one of the $C_1$–$C_6$-alkoxy groups mentioned above, especially the methoxycarbonyl-, ethoxycarbonyl-, isopropoxycarbonyl-, isobutoxycarbonyl- and tert-butoxycarbonyl group,
$C_2$–$C_7$-alkoxycarbonyloxy groups contain, aside from the oxygen atom, one of the $C_2$–$C_7$-alkoxycarbonyl residues mentioned above, especially the methoxycarbonyloxy-, ethoxycarbonyloxy-, isopropoxycarbonyloxy-, isobutoxycarbonyloxy- and tert-butoxycarbonyl group as well as the allyloxycarbonyloxy group,
$C_2$–$C_7$-alkylaminocarbonyl and $C_3$–$C_{13}$-dialkylaminocarbonyl groups contain, beside the carbonyl group, an alkylamino- and/or dialkylamino residue, whose $C_1$–$C_6$-alkyl groups have the above meanings, wherein the dimethylaminocarbonyl-, diethylaminocarbonyl- and the diisopropylaminocarbonyl groups are preferred, and
aside from the unsubstituted amino group, one of the following $C_1$–$C_6$-alkylamino groups and/or di-($C_1$–$C_6$-alkyl)amino groups are to be understood under the amino groups of the formula NR⁵R⁶,
$C_1$–$C_6$-alkylamino contains one of the $C_1$–$C_6$-alkyl groups mentioned above, especially in form of the methylamino-, ethylamino-, propylamino-, isopropylamino-, butylamino- and the tert-butylamino group,
di-($C_1$–$C_6$-alkyl)amino carries two of the same or different of the above named $C_1$–$C_6$-alkyl groups on the nitrogen atom, especially in form of the dimethylamino-, diethylamino-, dipropylamino-, diisopropylamino-, isopropylmethylamino-, dibutylamino- or tert-butylmethylamino group, $C_1$–$C_6$-acyl is the residue of an aliphatic saturated or unsaturated, straight chain, branched or cyclic carboxylic acid, especially in form of the formyl-, acetyl-, propionyl-, acryloyl-, butyryl-, isobutyryl-, methacryloyl-, cyclopropylcarbonyl-, pentanoyl-, pivaloyl-, cyclobutylcarbonyl-, hexanoyl- and the dimethylacryloyl group, $C_1$–$C_6$-alkansulfonyl is preferably the methanesulfonyl-, ethanesulfonyl-, propanesulfonyl-, butanesulfonyl-, pentanesulfonyl- and the hexanesulfonyl group, saturated five- to seven-membered heterocycles with one or two hetero-atoms are especially tetrahydrofuryl, tetrahydrothienyl, pyrrolidinyl, tetrahydropyranyl, piperdinyl, hexahydroazepinyl, piperazinyl, hexahydrodiazepinyl or morpholinyl, monocyclic aromatic five- or six-membered heterocycles with one to three hetero-atoms are especially furyl, thienyl, pyrrolyl, oxazolyl, isoxazolyl, thiazolyl, isothiazolyl, imidazolyl, pyrazolyl, oxadiazolyl, thiadiazolyl, triazolyl, pyridyl, pyrazinyl, pyridazinyl, pyrimidinyl or triazinyl, anellated bi- and tricyclic aromatic or partially hydrated carbocyclic ring systems with 8 to 16 ring atoms and at least one aromatic ring are preferably benzocyclobutyl, indanyl, indenyl, naphthyl, dihydronaphthyl, tetrahydronaphthyl, biphenylenyl, fluorenyl, anthryl, dihydroanthryl, phenanthryl, dihydrophenanthryl, dibenzocycloheptenyl, dihydrodibenzocycloheptenyl, dihydrodibenzocyclooctenyl or tetrahydrodibenzocyclooctenyl, wherein mono- or dioxo-derivates, wherein the residues of indanone, tetralone, anthrone, anthraquinone, fluorenone, phenanthrone, dibenzocycloheptenone, dihydrodibenzocycloheptenone or tetrahydrodibenzocyclooctenone are for example also to be understood as partially hydrated carbocyclic ring systems, anellated bi- and tricyclische aromatic or partially hydrated heterocyclic ring systems with 8 to 16 ring atoms and at least one aromatic ring are, for example, imidazothiazolyl, benzofuryl, dihydrobenzofuryl, benzothienyl, dihydrobenzothienyl, indolyl, indolinyl, benzimidazolyl, indazolyl, benzoxazolyl, benzisoxazolyl, benzothiazolyl, benzoisothiazolyl, benzofurazanyl, benzothiadiazolyl, benzotriazolyl, oxazolopyridyl, thiazolopyridyl, isothiazolopyridyl, imidazopyridyl, pyrazolopyridyl, thienopyrimidinyl, chromanyl, benzopyranyl, quinolyl, isoquinolyl, dihydroquinolyl, tetrahydroquinolyl, benzodioxanyl, quinoxalinyl, quinazolinyl, naphthyridinyl, carbazolyl, tetrahydrocarbazolyl, pyridoindolyl, acridinyl, phenothiazinyl, dihydrodibenzoxepinyl, benzocycloheptathienyl, dihydrothienobenzothiepinyl, dihydrodibenzothiepinyl, octahydrodibenzothiepinyl, dihydrodibenzazepinyl, octahydrodibenzazepinyl, benzocycloheptapyridyl, dihydropyridobenzodiazepinyl, dihydrodibenzoxazepinyl, dihydropyridobenzoxepinyl, dihydropyridobenzoxazepinyl, dihydrodibenzothiazepinyl or dihydropyridobenzothiazepinyl, wherein their mono- or dioxo-derivates and/or optionally their possible tautomeres are also to be understood as partially hydrated heterocyclic ring systems, for example, the residues of indolinone, isatin, benzoxazolone and/or its tautomeres hydroxybenzoxazol, of benzisoxazolone, benzothiazolone, benzoisothiazolone and benzimidazolone and/or their tautomeres, hydroxybenzisoxazol, hydroxybenzothiazol, hydroxybenzoisothiazol and hydroxybenzimidazol, of indazolinone, of oxazolopyridinone, thiazolopyridinones, pyrazolopyridinones and imidazopyridinones and/or their tautomeres hydroxyoxazolopyridine, hydroxythiazolopyridines, hydroxypyrazolopyridines and hydroxyimidazopyridines, the residues of chromanone, chromone, quinolinone, dihydroquinolinone, tetrahydrocarbazolone, acridone, of dihydrodibenzoxepinones, benzocycloheptathiophenones, dihydrothienobenzothiepinones, dihydrodibenzothiepinones, dihydrodibenzoazepinones, benzocycloheptapyridinones, dihydropyridobenzoxazepinones, dihydrodibenzothiazepinones and of dihydropyridobenzothiazepinones, saturated and unsaturated monocyclic, four- to eight-membered heterocycles are —$NR^{13}R^{15}$ as a grouping which, aside from the essential nitrogen atom, can optionally contain one or two further hetero-atoms selected from N and/or S and/or O, for example azetidine, pyrrolidine, piperidine, (1H) tetrahydropyridine, hexahydroazepine, (1H) tetrahydroazepine, octahydroazocine, pyrazolidine, piperazine, hexahydrodiazepine, morpholine, hexahydrooxazepine, thiomorpholine or thiomorpholine-1,1-dioxide, saturated or unsaturated bi- or tricyclic, anellated or bridged heterocycles with 8 to 16 ring atoms, represent —$NR^{13}R^{15}$ as a grouping which, aside from the essential nitrogen atom optionally contain one or two further hetero-atoms, selected from N and/or S and/or O, for example 5-aza-bicyclo[2.1.1]hexane, 2-aza-bicyclo [2.2.1]heptane, 7-aza-bicyclo[2.2.1]heptane, 2,5-diaza-bicyclo[2.2.1]heptane, 2-aza-bicyclo[2.2.2]octane, 8-aza-bicyclo[3.2.1]octane, 2,5-diaza-bicyclo[2.2.2] octane, 9-aza-bicyclo[3.3.1]nonane, indoline, isoindoline, (1H)-dihydroquinoline, (1H)-tetrahydroquinoline, (2H)-tetrahydroisoquinoline, (1H)-tetrahydroquinoxaline, (4H)-dihydrobenzoxazine, (4H)-dihydrobenothiazine, (1H)-tetrahydrobenzo[b]azepine, (1H)-tetrahydrobenzo[c] azepine, (1H)-tetrahydrobenzo[d]azepine, (5H)-tetrahydroben-zo[b]oxazepine, (5H)-tetrahydrobenzo [b]thiazepine, 1,2,3,4-tetrahydro-9H-pyrido[3,4-b] indol, (10H)-dihydroacridine, 1,2,3,4-tetrahydroacridanone, (10H)-phenoxazin, (10H)-phenothiazine, (5H)-dibenzazepine, (5H)-dihydrodibenzazepine, (5H)-octahydrodibenzazepine, (5H)-dihydrodibenzodiazepine, (11H)-dihydrodibenzo [b,e]oxazepine, (11H)-dihydrodibenzo[b,e]thiazepine, (10H)-dihydrodibenzo[b,f]oxazepine, (10H)-dihydrodibenzo[b,f]thiazepine or (5H)-tetrahydrodibenzazocine, as well as optionally possible tautomeres in the case of substitution of the heterocycle as such or in an anellated ring system by free hydroxy, mercapto- and/or amino groups, and stereoisomers such as, if applicable, cis/trans-isomers, endo/exo-isomers, optic isomers such as enantiomers, diastereomers as pure isomers or mixtures and/or racemic mixtures as well as the pharmacologically acceptable acid addition salts with inorganic or organic acids, wherein the hydrochlorides, hydrobromides, hydroiodides, sulfates and phosphates, are preferred as addition salts with suitable inorganic acids and acetates, benzoates, 4-methoxybenzoate, 2- or 4-hydroxybenzoate, 4-chlorobenzoate, ascorbate, salicylate, formiate, glutarate, tricarballylate, citrates, fumarates, gluconates, malates, maleates, methanesulfonates, lactates, oxalates, succinates, tartrates and toluolsulfonates, for example p-toluolsulfonate are preferred as addition salts of organic acids.

Compounds in which the substitutents labelled in formula (I)

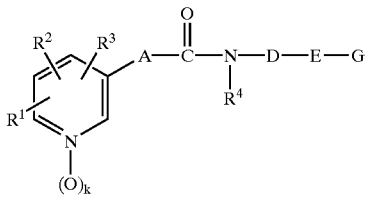
(I)

have the following meanings, are especially preferred:

$R^1$ is hydrogen, halogen, cyano, $C_1$–$C_6$-alkyl, trifluoromethyl, $C_3$–$C_8$-cycloalkyl, $C_1$–$C_4$-hydroxyalkyl, hydroxy, $C_1$–$C_4$-alkoxy, benzyloxy, $C_1$–$C_4$-alkanoyloxy, $C_1$–$C_4$-alkylthio, $C_2$–$C_5$-alkoxycarbonyl, aminocarbonyl, $C_3$–$C_9$-dialkylaminocarbonyl, carboxy, phenyl, phenoxy, pyridyloxy or $NR^5R^6$, wherein $R^5$ and $R^6$ are selected independently from each other form hydrogen and $C_1$–$C_6$-alkyl, $R^2$ is hydrogen, halogen, $C_1$–$C_6$-alkyl, trifluoromethyl or hydroxy, wherein $R^1$ and $R^2$, in the case they are adjacent, optionally form a bridge which are selected from the group of bridge members —$(CH_2)_4$— and —$(CH=CH)_2$— and —$CH_2O$—$CR^7R^8$—O—, wherein $R^7$ and $R^8$ can be, independently from each other, hydrogen and $C_1$–$C_6$-alkyl, $R^3$ is selected from hydrogen, halogen and $C_1$–$C_6$-alkyl and $R^4$ is selected from hydrogen, $C_1$–$C_6$-alkyl, $C_3$–$C_6$-alkenyl, hydroxy, $C_1$–$C_6$-alkoxy and benzyloxy, k is 0 or 1, A is selected from $C_1$–$C_6$-alkylene, which is optionally substituted once to three-fold by $C_1$–$C_3$-alkyl, hydroxy, fluorine or phenyl, 1,2-cyclopropylene, or $C_2$–$C_6$-alkylene, wherein a methylene unit can be isosterically replaced by O, S, $NR^9$, CO, SO or $SO_2$, and wherein the isosteric substitute, with the exception of =CO, cannot be adjacent to the amide group, and wherein $R^9$ is hydrogen, $C_1$–$C_3$-alkyl, $C_1$–$C_6$-acyl or methanesulfonyl, D is selected from $C_1$–$C_{10}$-alkylene, which is optionally substituted once or twice by $C_1$–$C_3$-alkyl or hydroxy, $C_2$–$C_{10}$-alkenylene, optionally substituted once or twice by $C_1$–$C_3$-alkyl or hydroxy, wherein the double bond can also be to ring E or $C_3$–$C_{10}$-alkinylene, which is optionally substituted once or twice by $C_1$–$C_3$-alkyl or hydroxy, and can be selected as well from $C_1$–$C_{10}$-alkylene, $C_2$–$C_{10}$-alkenylene or $C_3$–$C_{10}$-alkinylene, in which one to three methylene units are isosterically replaced by O, S, $NR^{10}$, CO, SO or $SO_2$, wherein $R^{10}$ has the same meaning as $R^9$, but is selected independently therefrom, E is

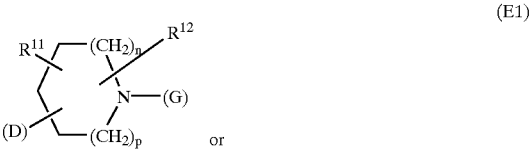
(E1)

or

(E2)

wherein the heterocyclic ring can optionally have a double bond and n and p can be, independent of each other, 0, 1, 2 or 3, with the proviso that n+p≦4, q is 2 or 3, $R^{11}$ is selected from hydrogen, $C_1$–$C_3$-alkyl, hydroxy, hydroxymethyl, carboxy or $C_2$–$C_7$-alkoxycarbonyl and $R^{12}$ is selected from hydrogen or an oxo group adjacent to the nitrogen atom, G is selected from hydrogen, G1, G2, G3, G4 and G5, wherein G1 represents the residue

(G1)

wherein r is 0, 1 or 2 and s is 0 or 1, $R^{13}$ is selected from hydrogen, $C_1$–$C_6$-alkyl, $C_3$–$C_6$-alkenyl, $C_3$–$C_6$-alkinyl, $C_3$–C-cycloalkyl, benzyl, phenyl, monocyclic aromatic five- or six-membered heterocycles, which contain one to three hetero-atoms from the group N and/or S and/or O and are either bound directly or over a methylene group, anellated bi- and tricyclic aromatic or partially hydrated carbocyclic ring systems with 8 to 16 ring atoms and at least one aromatic ring, whereby the bond can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from the groups N and/or S and/or O and the bond can occur either over an aromatic or a hydrated ring and either directly or over a methylene group, $R^{14}$ has the same meaning as $R^{13}$, but is selected independently thereof, $R^{15}$ is selected from hydrogen, hydroxy, methyl, benzyl or phenyl, monocyclic aromatic five- or six-membered heterocycles, which can contain one to three hetero-atoms selected from the group N and/or S and/or O and are bound either directly or over a methylene group, anellated bi- and tricyclic aromatic or partially hydrated carbocyclic ring systems with 8 to 16 ring atoms and at least einem aromatic ring, wherein the bond can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from the group N and/or S and/or O and the bond can occur either over an aromatic or a hydrated ring and either directly or over a methylene group, G2 is selected from the residues

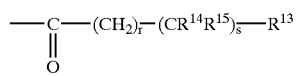
(G2a)

and

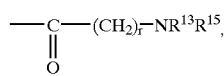
(G2b)

wherein the substituents $R^{13}$ and $R^{15}$ the can have the above meaning, or the grouping

can also be a nitrogen heterocycle bound over the nitrogen atom, selected from saturated or unsaturated monocyclic, four- to eight-membered heterocycles, which, aside from the essential nitrogen atom, can optionally contain one or two further hetero-atoms selected from N and/or S and/or O, or saturated or unsaturated bi- or tricyclic, anellated or bridged heterocycles with 8 to 16 ring atoms, which, aside from the essential nitrogen atom, can optionally contain one or two further hetero-atoms selected from N and/or S and/or O, G3 is the residue

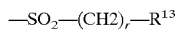
(G3),

G4 is the residue

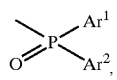
(G4)

wherein
Ar$^1$ and
Ar$^2$ are selected independently of each other from phenyl, pyridyl or naphthyl, G5 is the residue

(G5)

wherein
$R^{16}$ is trifluoromethyl, $C_1$–$C_6$-alkoxy, $C_3$–$C_6$-alkenyloxy or benzyloxy and aromatic ring systems in which the substituents $R^1$, $R^2$, $R^4$, $R^{13}$, $R^{14}$, $R^{15}$, $R^{16}$, AR$^1$ and Ar$^2$ and/or in the ring system —NR$^{13}$R$^{15}$ can carry independently of each other one to three of the same or different substituents from the series halogen, cyano, $C_1$–$C_6$-alkyl, trifluoromethyl, $C_3$–$C_8$-cycloalkyl, phenyl, benzyl, hydroxy, $C_1$–$C_6$-alkoxy, which is optionally entirely or partially substituted by fluorine, benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino, di-($C_1$–$C_6$-alkyl)-amino, wherein two adjacent groups on the aromatic ring or ring system can form an additional ring over a methylenedioxy bridge.

Compounds in which the substiutents labelled in formula (I)

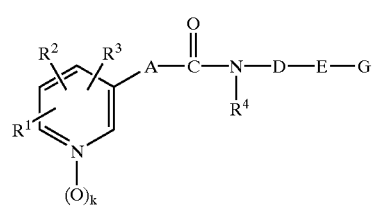
(I)

have the following meanings are particularly preferred:

$R^1$ is hydrogen, halogen, cyano, methyl, trifluoromethyl, hydroxy, $C_1$–$C_4$-alkoxy, ethylthio, methoxycarbonyl, tert-butoxycarbonyl, aminocarbonyl, carboxy, and phenoxy, $R^2$ is hydrogen, halogen, trifluoromethyl or hydroxy, $R^3$ is hydrogen or halogen, $R^4$ is selected from hydrogen, $C_1$–$C_3$-alkyl, hydroxy and $C_1$–$C_3$-alkoxy, k is 0 or 1, A is $C_2$–$C_6$-alkylene, which is optionally substituted once or twice by $C_1$–$C_3$-alkyl, hydroxy or fluorine, as well as $C_2$–$C_6$-alkylene, wherein a methylene unit can be isosterically replaced by O, S, CO or $SO_2$, and the isosteric substitute, with the exception of =CO, cannot be adjacent to the amide group, D is $C_1$–$C_8$-alkylene, which is optionally substituted once twice by methyl or hydroxy, $C_2$–$C_8$-alkenylene, which is optionally substituted once or twice by methyl or hydroxy, wherein the double bond can also be to ring E, $C_3$–$C_8$-alkinylene, which is optionally substituted once or twice by methyl or hydroxy, as well as $C_1$–$C_8$-alkylene, $C_2$–$C_8$-alkenylene or $C_3$–$C_8$-alkinylene, in which one to three methylene units can be isosterically replaced by O, S, NH, N($CH_3$), N($COCH_3$), N($SO_2CH_3$), CO, SO or $SO_2$, E is

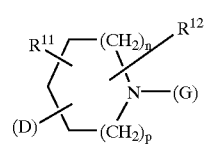
(E1)

or

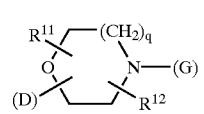
(E2)

wherein the heterocyclic ring can optionally have a double bond and n and p can be independent of each other 0, 1, 2 or 3, with the proviso that n+p≦3, q is 2 or 3, $R^{11}$ is selected from hydrogen, $C_1$–$C_3$-alkyl, hydroxy, hydroxymethyl and $R^{12}$ is selected from hydrogen or an oxo group which is adjacent to the nitrogen atom, G is hydrogen or G1, G2, G3, G4 and G5, wherein G1 represents the residue

  (G1)

wherein r is 0, or 2 and s is 0 or 1, $R^{13}$ is selected from hydrogen, $C_1$–$C_6$-alkyl, $C_3$–$C_8$-cycloalky, benzyl or phenyl, benzocyclobutyl, indanyl, indenyl, oxoindanyl, naphthyl, dihydronaphthyl, tetrahydronaphthyl, oxotetrahydronaphthyl, biphenylenyl, fluorenyl, oxofluorenyl, anthryl, dihydroanthryl, oxodihydroanthryl, dioxodihydroanthryl, phenanthryl, dihydrophenanthryl, oxodihydrophenanthryl, dibenzocycloheptenyl, oxodibenzocycloheptenyl, dihydrodibenzocycloheptenyl, oxodihydrodibenzocycloheptenyl, dihydrodibenzocyclooctenyl, tetrahydrodibenzocyclooctenyl and oxotetrahydrodibenzocyclooctenyl, bound directly or over a methylene group, furyl, thienyl, pyrrolyl, oxazolyl, isoxazolyl, thiazolyl, isothiazolyl, pyrazolyl, imidazolyl, oxadiazolyl, thiadiazolyl, triazolyl, pyridyl, pyrazinyl, pyridazinyl, pyrimidinyl, triazinyl, imidazothiazolyl, benzofuryl, dihydrobenzofuryl, benzothienyl, dihydrobenzothienyl, indolyl, indolinyl, oxoindolinyl, dioxoindolinyl, benzoxazolyl, oxobenzoxazolinyl, benzisoxazolyl, oxobenzisoxazolinyl, benzothiazolyl, oxobenzthiazolinyl, benzoisothiazolyl, oxobenzoisothiazolinyl, benzimidazolyl, oxobenzimidazolinyl, indazolyl, oxoindazolinyl, benzofurazanyl, benzothiadiazolyl, benzotriazolyl, oxazolopyridyl, oxodihydrooxazolopyridyl, thiazolopyridyl, oxodihydrothiazolopyridyl, isothiazolopyridyl, imidazopyridyl, oxodihydroimidazopyridyl, pyrazolopyridyl, oxodihydropyrazolopyridyl, thienopyrimidinyl, chromanyl, chromanonyl, benzopyranyl, chromonyl, quinolyl, isoquinolyl, dihydroquinolyl, oxodihydroquinolinyl, tetrahydroquinolyl, oxotetrahydroquinolinyl, benzodioxanyl, quinoxalinyl, quinazolinyl, naphthyridinyl, carbazolyl, tetrahydrocarbazolyl, oxotetrahydrocarbazolyl, pyridoindolyl, acridinyl, oxodihydroacridinyl, phenothiazinyl, dihydrodibenzoxepinyl, oxodihydrodibenzoxepinyl, benzocycloheptathienyl, oxobenzocycloheptathienyl, dihydrothienobenzothiepinyl, oxodihydrothienobenzothiepinyl, dihydrodibenzothiepinyl, oxodihydrodibenzothiepinyl, octahydrodibenzothiepinyl, dihydrodibenzazepinyl, oxodihydrodibenzazepinyl, octahydrodibenzazepinyl, benzocycloheptapyridyl, oxobenzocycloheptapyridyl, dihydropyridobenzodiazepinyl, dihydrodibenzoxazepinyl, dihydropyridobenzoxepinyl, dihydropyridobenzoxazepinyl, oxodihydropyridobenzoxazepinyl, dihydrodibenzothiazepinyl, oxodihydrodibenzothiazepinyl, dihydropyridobenzothiazepinyl, oxodihydropyridobenzoxazepinyl, bound directly or over a methylene group, $R^{14}$ has the same meaning as $R^{13}$, but is selected independently therefrom, $R^{15}$ is selected from hydrogen, hydroxy, methyl, benzyl or phenyl, indanyl, indenyl, naphthyl, dihydronaphthyl, tetrahydronaphthyl, furyl, thienyl, pyrrolyl, oxazolyl, isoxazolyl, thiazolyl, isothiazolyl, pyrazolyl, imidazolyl, oxadiazolyl, thiadiazolyl, triazolyl, pyridyl, pyrazinyl, pyridazinyl, pyrimidinyl, triazinyl, benzofuryl, benzothienyl, indolyl, indolinyl, benzoxazolyl, benzothiazolyl, benzimidazolyl, chromanyl, quinolyl or tetrahydroquinolyl, bound directly or over a methylene group, G2 is selected from the residues

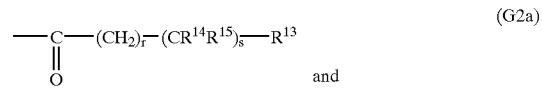  (G2a)

and

  (G2b)

wherein the substituents $R^{13}$ and $R^{15}$ can have the above meanings, or represents the grouping

each over the nitrogen-bound ring atom of azetidine, pyrrolidine, piperidine, (1H)tetrahydropyridine, hexahydroazepine, (1H)tetrahydroazepine, octahydroazocine, pyrazolidine, piperazine, hexyhydrodiazepine, morpholine, hexahydrooxazepine, thiomorpholine, thiomorpholine-1,1-dioxide, 5-aza-bi-cyclo[2.1.1]hexane, 2-aza-bicyclo[2.2.1]heptane, 7-aza-bicyclo[2.2.1]heptane, 2,5-diaza-bicyclo[2.2.1]heptane, 2-aza-bicyclo[2.2.2]octane, 8-aza-bicyclo[3.2.1]octane, 2,5-diazabicyclo[2.2.2]octane, 9-azabicyclo[3.3.1]nonane, indoline, isoindoline, (1H)-dihydroquinoline, (1H)-tetrahydroquinoline, (2H)-tetrahydroisoquinoline, (1H)-tetrahydroquinoxaline, (4H)-dihydrobenzoxazine, (4H)-dihydrobenzothiazine, (1H)-tetrahydrobenzo[b]azepine, (1H)-tetrahydrobenzo[c]azepine, (1H)-tetrahydrobenzo[d]azepine, (5H)-tetrahydrobenzo[b]oxazepine, (5H)-tetrahydrobenzo[b]thiazepine, 1,2,3,4- tetrahydro-9H-pyrido[3,4-b]indole, (10H)-dihydroacridine, 1,2,3,4-tetrahydroacridanone, (10H)-phenoxazine, (10H)-phenothiazine, (5H)-dibenzazepine, (5H)-dihydrodibenzazepine, (5H)-octahydrodibenzazepine, (5H)-dihydrodibenzodiazepine, (11H)-dihydrodibenzo[b,e]oxazepine, (11H)-dihydrodibenzo[b,e]thiazepine, (10H)-dihydrodibenzo[b,f]oxazepine, (10H)-dihydrodibenzo[b,f]thiazepine or (5H)-tetrahydrodibenzazocine, G3 is the residue $$-SO_2-(CH_2)_r-R^{13} \quad (G3),$$

G4 is the residue $$\underset{O}{\overset{}{\underset{}{\text{P}}}}\underset{Ar^2}{\overset{Ar^1}{\diagup}} \quad (G4)$$

wherein
Ar$^1$ and
Ar$^2$ are selected independently of each other from phenyl, pyridyl or naphthyl,
G5 is the residue $$-COR^{16} \quad (G5)$$

wherein
R$^{16}$ is trifluoromethyl, C$_1$–C$_6$-alkoxy, C$_3$–C$_6$-alkenyloxy or benzyloxy and aromatic ring systems in which the substituents can be substituted independently of each other by one to three of the same or different substituents from the series halogen, cyano, C$_1$–C$_6$-alkyl, trifluoromethyl, C$_3$–C$_8$-cycloalkyl, phenyl, benzyl, hydroxy, C$_1$–C$_6$-alkoxy, C$_1$–C$_6$-alkoxy, which can be entirely or partially substituted by fluorine, can carry benzyloxy, phenoxy, mercapto, C$_1$–C$_6$-alkylthio, carboxy, C$_1$–C$_6$-alkoxycarbonyl, benzyloxycarbonyl, nitro, amino, mono-C$_1$–C$_6$-alkylamino, di-(C$_1$–C$_6$-alkyl)-amino, wherein two adjacent groups can form an additional ring with a methylenedioxy bridge.

A further preferred embodiment of the invention comprises compounds which are distinguished in that the substituents labelled in formula (I)

$$\text{(I)}$$

have the following meaning:
R$^1$ is hydrogen, halogen, cyano, methyl, trifluoromethyl, hydroxy, methoxy or methoxycarbonyl,
R$^2$ is hydrogen or halogen,
R$^3$ is hydrogen,
R$^4$ is selected from hydrogen, C$_1$–C$_3$-alkyl or hydroxy,
k is 0 or 1,
A is selected from C$_2$–C$_6$-alkylene, which is optionally substituted once or twice by hydroxy or fluorine and
C$_2$–C$_6$-alkylene, wherein a methylene unit can be isosterically replaced by O, S or CO, and the isosteric substitute, with the exception of =CO, cannot be adjacent to the amide group and,
D is C$_2$–C$_8$-alkylene, which is optionally substituted by methyl or hydroxy,
C$_2$–C$_8$-alkenylene, which is optionally substituted by methyl or hydroxy, wherein the double bond can also be to ring E, or
C$_2$–C$_8$-alkylene, C$_2$–C$_8$-alkenylene, wherein one to three methylene units can be isosterically replaced by O, NH, N(CH$_3$), N(COCH$_3$), N(SO$_2$CH$_3$) or CO,
E is selected from the residues $$\text{(E1)}$$

or $$\text{(E2)}$$

wherein the heterocyclic ring can optionally have a double bond and
n and p can be, independent of each other, 0, 1, 2 or 3, with the proviso that n+p≦3 and
q is 2
R$^{11}$ is hydrogen, methyl or hydroxyl and
R$^{12}$ is hydrogen or an oxo group adjacent to the nitrogen atom,
G is selected from hydrogen, C$_3$–C$_8$-cycloalkyl, methoxycarbonyl, tert-butoxycarbonyl, benzyloxycarbonyl, trifluoroacetyl, diphenylphosphinoyl or the residues $$-(CH2)_r-(CR^{14}R^{15})_s-R^{13} \quad (G1)$$

and $$-\underset{\overset{\|}{O}}{C}-(CH_2)_r-(CR^{14}R^{15})_s-R^{13} \quad (G2a)$$

and $$-\underset{\overset{\|}{O}}{C}-(CH_2)_r-NR^{13}R^{15} \quad (G2b)$$

and $$-SO_2-(CH_2)_r-R^{13} \quad (G3)$$

wherein
r is 0, 1 or 2 and
s is 0 or 1,
R$^{13}$ is hydrogen, methyl, benzyl or phenyl, indanyl, indenyl, oxoindanyl, naphthyl, dihydronaphthyl, tetrahydronaphthyl, oxotetrahydronaphthyl, fluorenyl, oxofluorenyl, anthryl, dihydroanthryl, oxodihydroanthryl, dioxodihydroanthryl, dibenzocycloheptenyl, oxodibenzocycloheptenyl, dihydrodibenzocycloheptenyl, oxodihydrodibenzocycloheptenyl bound directly or over a methylene group, furyl, thienyl, pyrrolyl, oxazolyl, isoxazolyl, thiazolyl, isothiazolyl, pyrazolyl, imidazolyl, oxadiazolyl, thiadiazolyl, triazolyl, pyridyl, pyrazinyl, pyridazinyl, pyrimidinyl, imidazothiazolyl, benzofuryl, dihydrobenzofuryl, benzothienyl, dihydrobenzothienyl, indolyl, indolinyl, oxoindolinyl, dioxoindolinyl, benzoxazolyl, oxobenzoxazolinyl, benzisoxazolyl, oxobenzisoxazolinyl, benzothiazolyl, oxobenzthiazolinyl, benzoisothiazolyl, oxobenzoisothiazolinyl, benzimidazolyl, oxobenzimidazolinyl, benzofurazanyl, benzothiadiazolyl, benzotriazolyl, oxazolopyridyl, oxodihydrooxazolopyridyl, thiazolopyridyl, oxodihydrothiazolopyridyl, isothiazolopyridyl, imidazopyridyl, oxodihydroimidazopyridyl, pyrazolopyridyl, thienopyrimidinyl, chromanyl, chromanonyl, benzopyranyl, chromonyl, quinolyl, isoquinolyl, dihydroquinolyl, oxodihydroquinolinyl, tetrahydroquinolyl, oxotetrahydroquinolinyl, benzodioxanyl, quinoxalinyl, quinazolinyl, naphthyridinyl, carbazolyl, tetrahydrocarbazolyl, oxotetrahydrocarbazolyl, pyridoindolyl, acridinyl, oxodihydroacridinyl, phenothiazinyl, dihydrodibenzoxepinyl, benzocycloheptathienyl, oxobenzocycloheptathienyl, dihydrothienobenzothiepinyl, oxodihydrothienobenzothiepinyl dihydrodibenzothiepinyl, oxodihydrodibenzothiepinyl, dihydrodibenzazepinyl, oxodihydrodibenzazepinyl, octahydrodibenzazepinyl, benzocycloheptapyridyl, oxobenzocycloheptapyridyl, dihydropyridobenzoxepinyl, dihydrodibenzothiazepinyl, oxodihydrodibenzothiazepinyl bound directly or over a methylene group, $R^{14}$ is hydrogen, methyl, benzyl or phenyl, $R^{15}$ is selected from hydrogen, hydroxy, methyl, benzyl, phenyl, naphthyl, furyl, thienyl, oxazolyl, thiazolyl, pyrazolyl, imidazolyl, oxadiazolyl, thiadiazolyl, pyridyl, benzofuryl, benzothienyl, indolyl, indolinyl, benzoxazolyl, benzothiazolyl, benzimidazolyl, chromanyl, quinolyl or tetrahydroquinolyl, bound directly or over a methylene group, wherein in formula (I)

(G2b)

the group $NR^{13}R^{15}$ can also be selected from pyrrolidine, piperidine, (1H)tetrahydropyridine, hexahydroazepine, Octahydroazocine, piperazine, hexahydrodiazepine, morpholine, hexahydrooxazepine, 2-azabicyclo[2.2.1]heptane, 7-azabicyclo[2.2.1]heptane, 2,5-diazabicyclo[2.2.1]heptane, 8-azabicyclo[3.2.1]octane, 2,5-diazabicyclo[2.2.2]octane, indoline, isoindoline, (1H)-dihydroquinoline, (1H)-tetrahydroquinoline, (2H)-tetrahydroisoquinoline, (1H)-tetrahydroquinoxaline, (4H)-dihydrobenzoxazine, (4H)-dihydrobenzothiazine, (1H)-tetrahydrobenzo[b]azepine, (1H)-tetrahydrobenzo[d]azepine, (5H)-tetrahydrobenzo[b]oxazepine, (5H)-tetrahydrobenzo[b]thiazepine, 1,2,3,4-tetrahydro-9H-pyrido[3,4-b]indol, (10H)-dihydroacridine, 1,2,3,4-tetrahydroacridanone, (5H)-dihydrodibenzazepine, (5H)-dihydrodibenzodiazepine, (11H)-dihydrodibenzo[b,e]oxazepine, (11H)-dihydrodibenzo[b,e]thiazepine, (10H)-dihydrodibenzo[b,f]oxaze-pine or (5H)-tetrahydrodibenzazocine.

Compounds in which the labelled substituents in the formula (I)

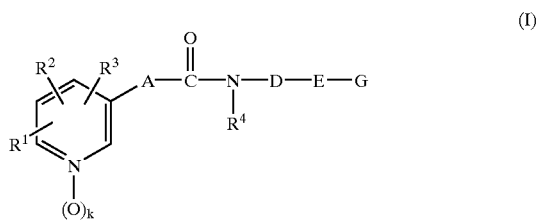
(I)

have the following meanings are very particularly preferred:

$R^1$ is hydrogen, fluorine, chlorine, bromine, methyl, trifluoromethyl or hydroxy, $R^2$ and $R^3$ are hydrogen, $R^4$ is hydrogen or hydroxy, k is 0 or 1, A is selected from $C_2$–$C_6$-alkylene, which is optionally substitued once or twice by hydroxy or fluorine, D is selected from $C_2$–$C_6$-alkylene, $C_2$–$C_6$-alkenylene, wherein the double bond can also be to ring E, and $C_2$–$C_6$-alkylene and $C_2$–$C_6$-alkenylene, wherein a methylene unit can be isosterically replaced by O, NH, N(CH$_3$) or CO or an ethylene group can be isosterically replaced by NH—CO and/or CO—NH or a propylene group can be isosterically replaced by NH—CO—O and/or O—CO—NH, E is selected from pyrrolidine, piperidine, 1,2,5,6-tetrahydropyridine, hexahydroazepine, morpholine and hexahydro-1,4-oxazepine, wherein the heterocyclic ring optionally adjacent to the nitrogen atom, can be substituted by an oxo group, G is selected from hydrogen, tert-butoxycarbonyl, diphenylphosphinoyl, or one of the residues

(G1)

and

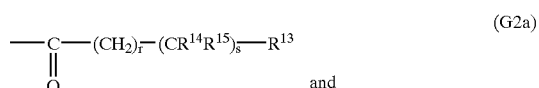
(G2a)

and

(G2b)

and

(G3)

wherein
r is 0 or 1 and
s is 0 or 1,
R¹³ is hydrogen, methyl, benzyl or phenyl,
  indenyl, oxoindanyl, naphthyl, tetrahydronaphthyl, fluorenyl, oxofluorenyl, anthryl, dihydroanthryl, oxodihydroanthryl, dioxodihydroanthryl, dibenzocycloheptenyl, dihydrodibenzocycloheptenyl bound directly or over a methylene group,
  furyl, thienyl, oxazolyl, thiazolyl, imidazolyl, oxadiazolyl, thiadiazolyl, pyridyl, pyrazinyl, pyrimidinyl, imidazothiazolyl, benzofuryl, benzothienyl, indolyl, oxoindolinyl, dioxoindolinyl, benzoxazolyl, oxobenzoxazolinyl, benzothiazolyl, oxobenzthiazolinyl, benzimidazolyl, oxobenzimidazolinyl, benzofurazanyl, benzotriazolyl, oxazolopyridyl, oxodihydrooxazolopyridyl, thiazolopyridyl, oxodihydrothiazolopyridyl, chromanyl, chromanonyl, benzopyranyl, chromonyl, quinolyl, isoquinolyl, oxodihydroquinolinyl, tetrahydroquinolyl, oxotetrahydroquinolinyl, benzodioxanyl, quinazolinyl, acridinyl, oxodihydroacridinyl, phenothiazinyl, dihydrodibenzoxepinyl, benzocycloheptathienyl, dihydrothienobenzothiepinyl, dihydrodibenzothiepinyl, oxodihydrodibenzothiepinyl, dihydrodibenzazepinyl, oxodihydrodibenzazepinyl, octahydrodibenzazepinyl, benzocycloheptapyridyl, oxobenzocycloheptapyridyl, dihydrodibenzothiazepinyl bound directly or over a methylene group, R¹⁴ is hydrogen, methyl, benzyl or phenyl,
R¹⁵ is hydrogen, hydroxy, methyl, benzyl or phenyl, naphthyl, furyl, thienyl, pyridyl, benzofuryl, benzothienyl, indolyl, benzoxazolyl, benzothiazolyl, benzimidazolyl, chromanyl, quinolyl or tetrahydroquinolyl bound directly or over a methylene group, wherein in the formula

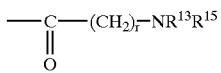 (G2b)

the group NR¹³R¹⁵ can be selected from pyrrolidine, piperidine, hexahydroazepine, morpholine, 2,5-diazabicyclo[2.2.1]heptane, indoline, isoindoline, (1H)-dihydroquinoline, (1H)-tetrahydroquinoline, (2H)-tetrahydroisoquinoline, (1H)-tetrahydrobenzo[b]azepine, (1H)-tetrahydrobenzo[d]azepine, (5H)-tetrahydrobenzo[b]oxazepine, (5H)-tetrahydrobenzo[b]thiazepine, 1,2,3,4-tetrahydroacridanone, (5H)-dihydrodibenzazepine, (11H)-dihydrodibenzo[b,e]-oxazepine or (11H)-dihydrodibenzo[b,e]thiazepine and wherein aromatic ring systems in the substituents can be substituted, independently of each other, by one to three of the same or different substituents from the series halogen, cyano, $C_1$–$C_6$-alkyl, trifluoromethyl, $C_3$–$C_8$-cycloalkyl, phenyl, benzyl, hydroxy, $C_1$–$C_6$-alkoxy, $C_1$–$C_6$-alkoxy, which can be entirely or partially substituted by fluorine, can carry benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino or di-($C_1$–$C_6$-alkyl)-amino, whereby two adjacent groups on the aromatic ring or ring system for an additional ring over a methylenedioxy bridge.

Compounds are especially preferred which distinguish themselves in that the substituents labelled in the formula (I)

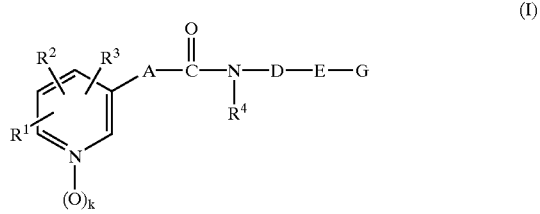 (I)

have the following meanings:
R¹ is hydrogen, fluorine, methyl, trifluoromethyl or hydroxy,
R² and
R³ are hydrogen,
R⁴ is hydrogen or hydroxy,
k is 0,
A is selected from ethylene, propylene or butylene optionally substituted by hydroxy or one or two fluorine atoms,
D is selected from $C_2$–$C_6$-alkylene or $C_2$–$C_6$-alkenylene, wherein the double bond can also be to ring E,
E is selected from pyrrolidine, piperidine, hexahydroazepine or morpholine,
G is selected from benzyl, phenethyl, fluorenymethyl, anthrylmethyl, diphenylmethyl, fluorenyl or dihydrodibenzocycloheptenyl,
  furylmethyl, thienylmethyl, thiazolylmethyl, pyridylmethyl, benzothienylmethyl, quinolylmethyl, phenyl-thienylmethyl, phenyl-pyridylmethyl, dihydrodibenzoxepinyl, dihydrodibenzothiepinyl,
  acetyl, pivaloyl, phenylacetyl, diphenylacetyl, diphenylpropionyl, naphthylacetyl, benzoyl, naphthoyl, anthrylcarbonyl, oxofluorenylcarbonyl, oxodihydroanthrylcarbonyl or dioxodihydroanthrylcarbonyl,
  furoyl, pyridylcarbonyl, chromonylcarbonyl, quinolylcarbonyl,
  naphthylaminocarbonyl, dibenzylaminocarbonyl, benzylphenylaminocarbonyl, diphenylaminocarbonyl, indolinyl-1-carbonyl, dihydrodibenzazepin-N-carbonyl, tetrahydroquinolinyl-N-carbonyl, tetrahydrobenzo[b]azepinyl-N-carbonyl,
  methanesulfonyl, phenylsulfonyl, p-toluolsulfonyl, naphthylsulfonyl, quinolinsulfonyl and
diphenylphosphinoyl,
  wherein aromatic ring systems can be substituted independently of each other by one to three of the same or different substituents from the series halogen, cyano, $C_1$–$C_6$-alkyl, trifluoromethyl, $C_3$–$C_8$-cycloalkyl, phenyl, benzyl, hydroxy, $C_1$–$C_6$-alkoxy, $C_1$–$C_6$-alkoxy, which can be entirely or partially substituted by fluorine, benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino or di-($C_1$–$C_6$-alkyl)-amino, wherein two adjacent groups in the ring or ring system can form an additional ring over a methylendioxy bridge.

A series of exemplary compounds with the respective substituent definitions are listed in the following Table 1 for illustration of the invention without restricting the scope of the compounds according to the invention.

TABLE 1

Exemplifying compounds of formula (I) according to the invention

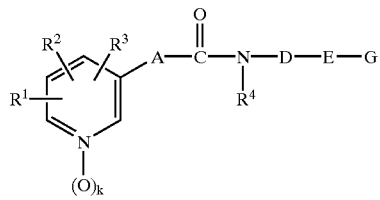

| Nr | $R^1$ | k | A | $R^4$ | D-E-G |
|---|---|---|---|---|---|
| 1 | H | 0 | $CH_2CH_2$ | H | 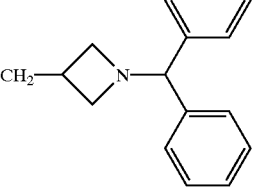 |
| 2 | H | 0 | $CH_2CH_2CH_2CH_2$ | H | 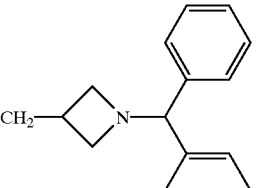 |
| 3 | H | 0 | $CH_2CH_2$ | H | 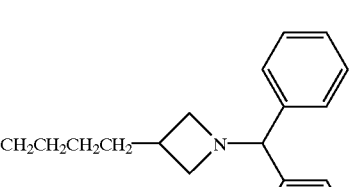 |
| 4 | H | 0 | $CH_2CH_2$ | H | 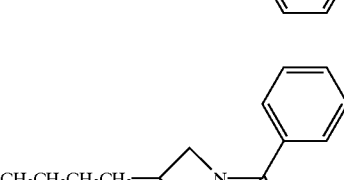 |
| 5 | H | 0 | $CH_2CH_2$ | H | 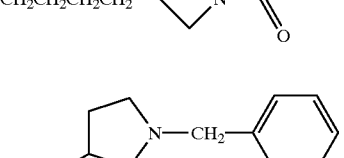 |

TABLE 1-continued
Exemplifying compounds of formula (I) according to the invention
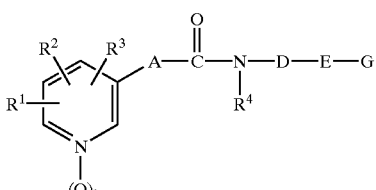
| Nr | R¹ | k | A | R⁴ | D-E-G |
|---|---|---|---|---|---|
| 6 | H | 0 | CH₂CH₂CH₂CH₂ | H | 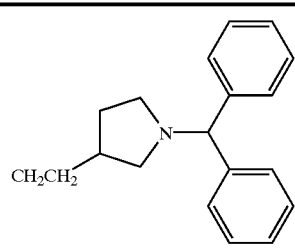 |
| 7 | H | 0 | CH₂CH₂CH₂ | H | 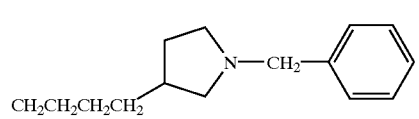 |
| 8 | H | 0 | CH₂CH₂ | H | 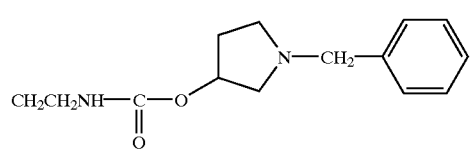 |
| 9 | H | 0 | CH₂CH₂ | H | 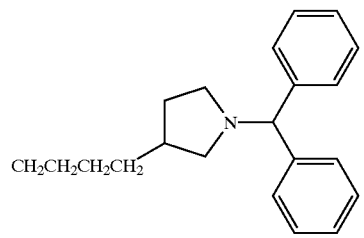 |
| 10 | H | 0 | CH₂CH₂ | H | 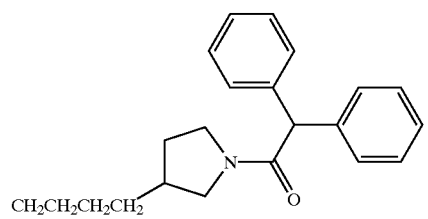 |
| 11 | H | 0 | CH₂CH₂ | H | 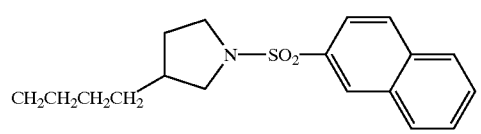 |
| 12 | H | 0 | CH₂CH₂ | H | 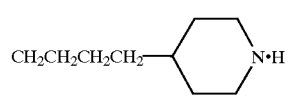 |
| 13 | H | 0 | CH₂CH₂CH₂CH₂ | H | 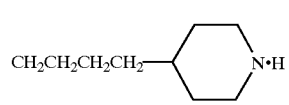 |

TABLE 1-continued

Exemplifying compounds of formula (I) according to the invention

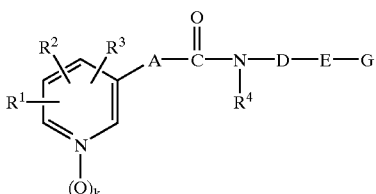

| Nr | R¹ | k | A | R⁴ | D-E-G |
|---|---|---|---|---|---|
| 14 | H | 0 | CH$_2$CH$_2$ | H | CH$_2$CH$_2$CH$_2$O—<piperidine>N•H |
| 15 | H | 0 | CH$_2$CH$_2$ | H | CH$_2$CH$_2$CH$_2$CH$_2$—<piperidine>N—CH$_3$ |
| 16 | H | 0 | CH$_2$CH$_2$ | H | CH$_2$CH$_2$CH$_2$CH$_2$—<piperidine>N—CH(CH$_3$)$_2$ |
| 17 | H | 0 | CH$_2$CH$_2$ | H | CH$_2$CH$_2$CH$_2$CH$_2$—<piperidine>N—cyclopropyl |
| 18 | H | 0 | CH$_2$CH$_2$ | H | CH$_2$CH$_2$CH$_2$CH$_2$—<piperidine>N—cyclohexyl |
| 19 | H | 0 | OCH$_2$ | H | CH$_2$CH$_2$—<piperidine>N—CH$_2$-cyclopropyl |
| 20 | H | 0 | CH$_2$CH$_2$ | H | CH$_2$CH$_2$—<piperidine>N—CH$_2$-cyclopropyl |
| 21 | H | 0 | CH$_2$CH$_2$ | H | CH$_2$CH$_2$—<piperidine>N—CH$_2$-cyclohexyl |
| 22 | H | 0 | CH$_2$CH$_2$ | H | CH$_2$CH$_2$CH$_2$CH$_2$—<piperidine>N—CH$_2$-(3-piperidinyl-NH) |
| 23 | H | 0 | CH$_2$CH$_2$ | H | CH$_2$CH$_2$CH$_2$CH$_2$—<piperidine>N—CH$_2$CH$_2$-(4-piperidinyl-NH) |

TABLE 1-continued
Exemplifying compounds of formula (I) according to the invention
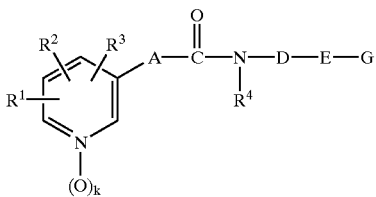
| Nr | R¹ | k | A | R⁴ | D-E-G |
|---|---|---|---|---|---|
| 24 | H | 0 | CH₂CH₂ | H | 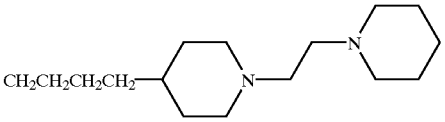 |
| 25 | H | 0 | CH₂CH₂ | H | 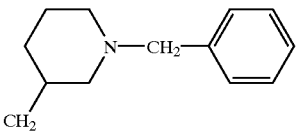 |
| 26 | H | 0 | CH₂CH₂ | H | 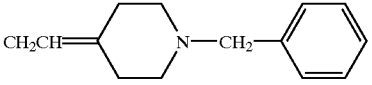 |
| 27 | H | 0 | CH₂CH₂CH₂CH₂ | H | 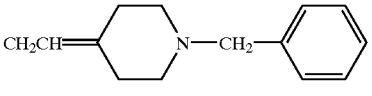 |
| 28 | H | 0 | CH₂CH₂ | H | 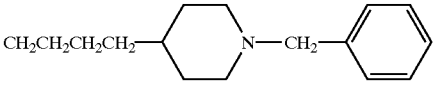 |
| 29 | 2-F | 0 | CH₂CH₂ | H | 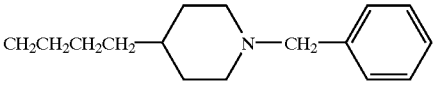 |
| 30 | H | 1 | CH₂CH₂ | H | 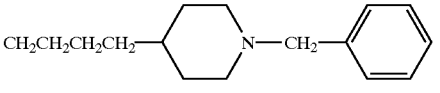 |
| 31 | H | 0 | CH₂CH₂ | OH | 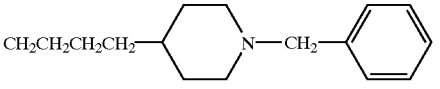 |
| 32 | H | 0 | △ | H | 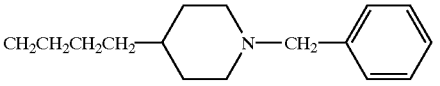 |
| 33 | H | 0 | CHCH₂ / CH₃ | H | 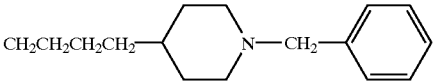 |
| 34 | H | 0 | CH₂CH₂CH₂CH₂ | H | 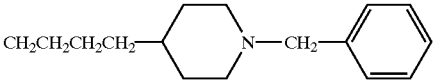 |
| 35 | H | 0 | (CH₂)₆ | H | 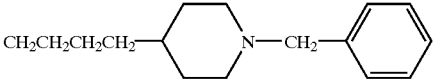 |

TABLE 1-continued
Exemplifying compounds of formula (I) according to the invention
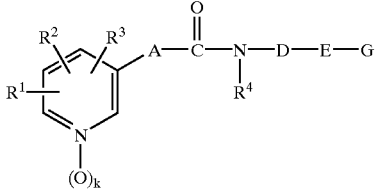
| Nr | R¹ | k | A | R⁴ | D-E-G |
|----|----|----|------|----|-------|
| 36 | H | 0 | CH₂CH₂ | H | 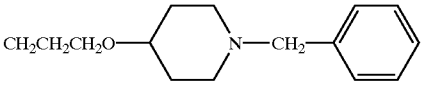 |
| 37 | H | 0 | CH₂CH₂ | H | 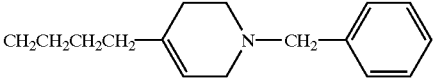 |
| 38 | H | 0 | CH₂CH₂ | H | 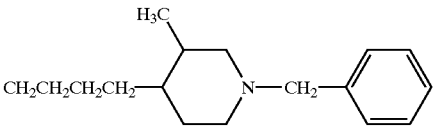 |
| 39 | H | 0 | CH₂CH₂ | H | 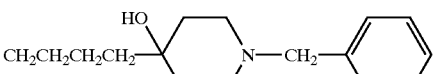 |
| 40 | H | 0 | CH₂CH₂ | H | 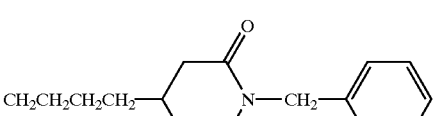 |
| 41 | H | 0 | CH₂CH₂ | H | 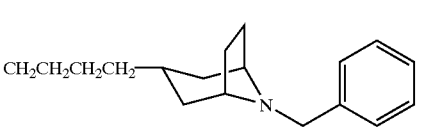 |
| 42 | H | 0 | CH₂CH₂ | H | 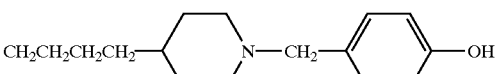 |
| 43 | H | 0 | CH₂CH₂ | H | 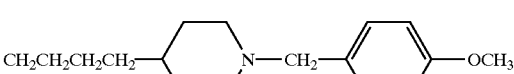 |
| 44 | H | 0 | CH₂CH₂ | H |  |
| 45 | H | 0 | CH₂CH₂ | H | 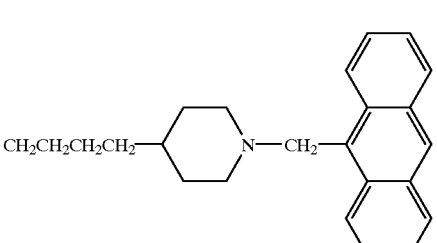 |

TABLE 1-continued

Exemplifying compounds of formula (I) according to the invention

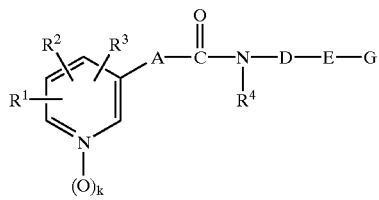

| Nr | R¹ | k | A | R⁴ | D-E-G |
|---|---|---|---|---|---|
| 46 | H | 0 | CH₂CH₂ | H | CH₂CH₂CH₂CH₂—[4-piperidinyl]—N—CH(phenyl)(cyclohexyl) |
| 47 | H | 0 | CH₂CH₂ | H | CH₂CH₂—[3-piperidinyl]—N—CH₂—(4-pyridyl) |
| 48 | H | 0 | CH₂CH₂CH₂CH₂ | H | CH₂CH₂CH₂CH₂—[4-piperidinyl]—N—CH₂—(3-pyridyl) |
| 49 | H | 0 | CH₂CH₂ | H | CH₂CH₂CH₂CH₂—[4-piperidinyl]—N—CH₂—(benzo[2,1,3]oxadiazol-5-yl) |
| 50 | H | 0 | CH₂CH₂ | H | CH₂CH₂—[3-piperidinyl]—N—CH(C₆H₅)₂ |
| 51 | H | 0 | CH₂CH₂ | H | CH₂CH₂CH₂CH₂—[4-piperidinyl]—N—CH(C₆H₅)₂ |
| 52 | H | 0 | CH₂CH₂ | H | CH₂CH₂NH—[4-piperidinyl]—N—CH(C₆H₅)₂ |
| 53 | H | 0 | CH₂ | H | CH₂CH₂CH₂CH₂—[4-piperidinyl]—N—CH(C₆H₅)₂ |
| 54 | H | 0 | CH₂CH₂ | H | CH₂CH₂CH₂CH₂—[4-piperidinyl]—N—CH(C₆H₅)₂ |

TABLE 1-continued

Exemplifying compounds of formula (I) according to the invention

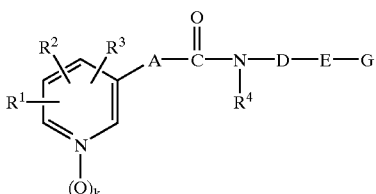

| Nr | R¹ | k | A | R⁴ | D-E-G |
|----|----|----|----|----|----|
| 55 | H | 1 | CH₂CH₂ | H | CH₂CH₂CH₂CH₂—piperidine—N—CH(C₆H₅)₂ |
| 56 | 2-F | 0 | CH₂CH₂ | H | CH₂CH₂CH₂CH₂—piperidine—N—CH(C₆H₅)₂ |
| 57 | 2-F | 0 | CH₂CH₂ | OH | CH₂CH₂CH₂CH₂—piperidine—N—CH(C₆H₅)₂ |
| 58 | 4-F | 0 | CH₂CH₂ | H | CH₂CH₂CH₂CH₂—piperidine—N—CH(C₆H₅)₂ |
| 59 | 5-F | 0 | CH₂CH₂ | H | CH₂CH₂CH₂CH₂—piperidine—N—CH(C₆H₅)₂ |
| 60 | 5-F | 0 | CH₂CH₂ | OH | CH₂CH₂CH₂CH₂—piperidine—N—CH(C₆H₅)₂ |
| 61 | 6-F | 0 | CH₂CH₂ | H | CH₂CH₂CH₂CH₂—piperidine—N—CH(C₆H₅)₂ |
| 62 | 2-Cl | 0 | CH₂CH₂ | H | CH₂CH₂CH₂CH₂—piperidine—N—CH(C₆H₅)₂ |
| 63 | 6-Cl | 0 | CH₂CH₂ | H | CH₂CH₂CH₂CH₂—piperidine—N—CH(C₆H₅)₂ |
| 64 | 6-CH₃ | 0 | CH₂CH₂CH₂CH₂ | H | CH₂CH₂CH₂CH₂—piperidine—N—CH(C₆H₅)₂ |
| 65 | 2-OH | 0 | CH₂CH₂ | H | CH₂CH₂CH₂CH₂—piperidine—N—CH(C₆H₅)₂ |
| 66 | 6-CH₃O | 0 | CH₂CH₂ | H | CH₂CH₂CH₂CH₂—piperidine—N—CH(C₆H₅)₂ |

TABLE 1-continued

Exemplifying compounds of formula (I) according to the invention

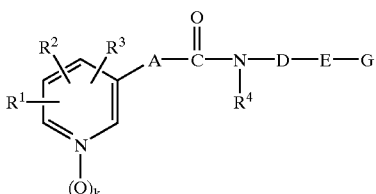

| Nr | R¹ | k | A | R⁴ | D-E-G |
|---|---|---|---|---|---|
| 67 | 6-C₆H₅O | 0 | CH₂CH₂ | H | CH₂CH₂CH₂CH₂—[piperidine]—N—CH(C₆H₅)₂ |
| 68 | H | 0 | CH₂CH₂ | CH₃CH₂ | CH₂CH₂CH₂CH₂—[piperidine]—N—CH(C₆H₅)₂ |
| 69 | H | 0 | CH₂CH₂ | OH | CH₂CH₂CH₂CH₂—[piperidine]—N—CH(C₆H₅)₂ |
| 70 | H | 0 | CH₂CH₂ | OCH₃ | CH₂CH₂CH₂CH₂—[piperidine]—N—CH(C₆H₅)₂ |
| 71 | H | 0 | CH₂CH₂ | OCH₂C₆H₅ | CH₂CH₂CH₂CH₂—[piperidine]—N—CH(C₆H₅)₂ |
| 72 | H | 0 | CHCH₂(CH₃) | H | CH₂CH₂CH₂CH₂—[piperidine]—N—CH(C₆H₅)₂ |
| 73 | H | 0 | CH₂CH(C₂H₅) | H | CH₂CH₂CH₂CH₂—[piperidine]—N—CH(C₆H₅)₂ |
| 74 | H | 0 | CH₂CH(C₆H₅) | H | CH₂CH₂CH₂CH₂—[piperidine]—N—CH(C₆H₅)₂ |
| 75 | H | 0 | CHFCH₂ | H | CH₂CH₂CH₂CH₂—[piperidine]—N—CH(C₆H₅)₂ |
| 76 | H | 0 | CH₂CHF | H | CH₂CH₂CH₂CH₂—[piperidine]—N—CH(C₆H₅)₂ |
| 77 | H | 0 | CHCH₂(OH) | H | CH₂CH₂CH₂CH₂—[piperidine]—N—CH(C₆H₅)₂ |
| 78 | H | 0 | CH₂CH(OH) | H | CH₂CH₂CH₂CH₂—[piperidine]—N—CH(C₆H₅)₂ |

TABLE 1-continued

Exemplifying compounds of formula (I) according to the invention

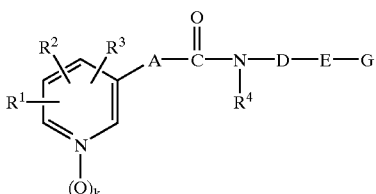

| Nr | R¹ | k | A | R⁴ | D-E-G |
|---|---|---|---|---|---|
| 79 | H | 0 | CCH₂ ‖ O | H | CH₂CH₂CH₂CH₂—⟨piperidine⟩N—CH(C₆H₅)₂ |
| 80 | H | 0 | CH₂C ‖ O | H | CH₂CH₂CH₂CH₂—⟨piperidine⟩N—CH(C₆H₅)₂ |
| 81 | H | 0 | CF₂CH₂ | H | CH₂CH₂CH₂CH₂—⟨piperidine⟩N—CH(C₆H₅)₂ |
| 82 | H | 0 | CH₂CF | H | CH₂CH₂CH₂CH₂—⟨piperidine⟩N—CH(C₆H₅)₂ |
| 83 | H | 0 | CHCF₂ \| OH | H | CH₂CH₂CH₂CH₂—⟨piperidine⟩N—CH(C₆H₅)₂ |
| 84 | H | 0 | OCH₂ | H | CH₂CH₂CH₂CH₂—⟨piperidine⟩N—CH(C₆H₅)₂ |
| 85 | H | 0 | △ | H | CH₂CH₂CH₂CH₂—⟨piperidine⟩N—CH(C₆H₅)₂ |
| 86 | H | 0 | CH₂CH₂CH₂ | H | CH₂CH₂CH₂CH₂—⟨piperidine⟩N—CH(C₆H₅)₂ |
| 87 | H | 0 | SCH₂CH₂ | H | CH₂CH₂CH₂CH₂—⟨piperidine⟩N—CH(C₆H₅)₂ |
| 88 | H | 0 | SO₂CH₂CH₂ | H | CH₂CH₂CH₂CH₂—⟨piperidine⟩N—CH(C₆H₅)₂ |
| 89 | H | 1 | SO₂CH₂CH₂ | H | CH₂CH₂CH₂CH₂—⟨piperidine⟩N—CH(C₆H₅)₂ |
| 90 | H | 0 | CH₂CH₂CH₂CH₂ | H | CH₂CH₂CH₂CH₂—⟨piperidine⟩N—CH(C₆H₅)₂ |

TABLE 1-continued

Exemplifying compounds of formula (I) according to the invention

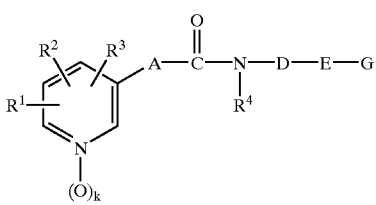

| Nr | R¹ | k | A | R⁴ | D-E-G |
|---|---|---|---|---|---|
| 91 | H | 0 | CH₂NHCH₂CH₂ | H | CH₂CH₂CH₂CH₂—[piperidine]—N—CH(C₆H₅)₂ |
| 92 | H | 0 | CH₂NCH₂CH₂ (N-CH₃) | H | CH₂CH₂CH₂CH₂—[piperidine]—N—CH(C₆H₅)₂ |
| 93 | H | 0 | CH₂NCH₂CH₂ (N-CHO) | H | CH₂CH₂CH₂CH₂—[piperidine]—N—CH(C₆H₅)₂ |
| 94 | H | 0 | CH₂NCH₂CH₂ (N-SO₂CH₃) | H | CH₂CH₂CH₂CH₂—[piperidine]—N—CH(C₆H₅)₂ |
| 95 | H | 0 | (CH₂)₅ | H | CH₂CH₂CH₂CH₂—[piperidine]—N—CH(C₆H₅)₂ |
| 96 | H | 0 | CH₂CH₂ | H | CH₂CH₂NH—C(=O)—[piperidine]—N—CH(C₆H₅)₂ |
| 97 | H | 0 | CH₂CH₂ | H | CH₂CH₂CH₂CH=[piperidine]—N—CH(C₆H₅)₂ |
| 98 | H | 0 | CH₂CH₂ | H | CH₂CH=CHCH₂—[piperidine]—N—CH(C₆H₅)₂ |
| 99 | H | 0 | CH₂CH₂ | H | CH₂C≡CCH₂—[piperidine]—N—CH(C₆H₅)₂ |
| 100 | H | 0 | CH₂CH₂ | H | CH₂CH₂CH₂CH₂—[tetrahydropyridine]—N—CH(C₆H₅)₂ |
| 101 | H | 0 | CH₂CH₂ | H | CH₂CH₂CH₂CH₂CH₂—[piperidine]—N—CH(C₆H₅)₂ |
| 102 | H | 0 | CH₂CH₂ | H | CH₂CH₂CH₂OCH₂—[piperidine]—N—CH(C₆H₅)₂ |

TABLE 1-continued

Exemplifying compounds of formula (I) according to the invention

| Nr | R¹ | k | A | R⁴ | D-E-G |
|---|---|---|---|---|---|
| 103 | H | 0 | $CH_2CH_2$ | H | $OCH_2CH_2CH_2CH_2$—[piperidine-4-yl]—N—$CH(C_6H_5)_2$ |
| 104 | H | 0 | $CH_2CH_2$ | H | $CH_2CH_2CH_2CH_2CH_2CH_2$—[piperidine-4-yl]—N—$CH(C_6H_5)_2$ |
| 105 | H | 0 | $CH_2CH_2$ | H | $CH_2CH_2CH_2OCH_2CH_2$—[piperidine-4-yl]—N—$CH(C_6H_5)_2$ |
| 106 | H | 0 | $CH_2CH_2$ | H | $CH_2CH_2CH_2CH_2NH$—C(=O)—[piperidine-3-yl]—N—$CH(C_6H_5)_2$ |
| 107 | H | 0 | $CH_2CH_2$ | H | $(CH_2)_8$—[piperidine-4-yl]—N—$CH(C_6H_5)_2$ |
| 108 | H | 0 | $CH_2CH_2$ | H | $(CH_2)_6NH$—C(=O)—[piperidine-3-yl]—N—$CH(C_6H_5)_2$ |
| 109 | H | 0 | $CH_2CH_2$ | H | $CH_2CH_2CH_2CH_2$—[3-methylpiperidine-4-yl]—N—$CH(C_6H_5)_2$ |
| 110 | H | 0 | $CH_2CH_2$ | H | $CH_2CH_2CH_2CH_2$—[4-hydroxypiperidine-4-yl]—N—$CH(C_6H_5)_2$ |
| 111 | H | 0 | $CH_2CH_2$ | H | $CH_2CH_2CH_2CH_2$—[2-oxopiperidine-3-yl]—N—$CH(C_6H_5)_2$ |

TABLE 1-continued
Exemplifying compounds of formula (I) according to the invention
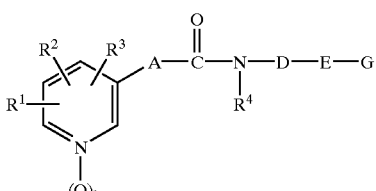
| Nr | R¹ | k | A | R⁴ | D-E-G |
|---|---|---|---|---|---|
| 112 | H | 0 | CH₂CH₂ | H | 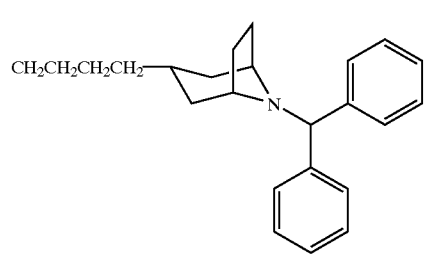 |
| 113 | H | 0 | CH₂CH₂ | H | 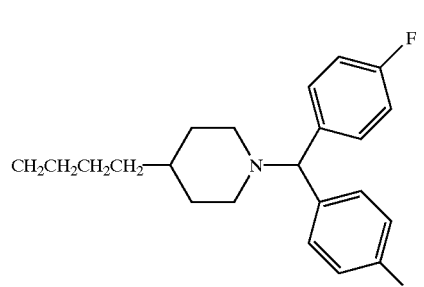 |
| 114 | H | 1 | CH₂CH₂ | H | 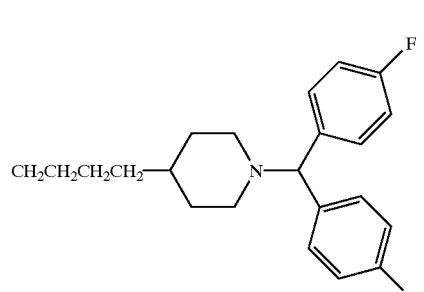 |
| 115 | H | 0 | CH₂CH₂CH₂CH₂ | H | 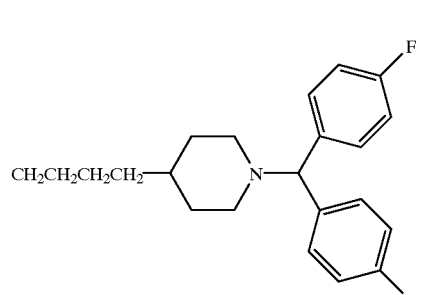 |

TABLE 1-continued

Exemplifying compounds of formula (I) according to the invention

| Nr | R¹ | k | A | R⁴ | D-E-G |
|---|---|---|---|---|---|
| 116 | H | 0 | CH$_2$CH$_2$ | H | CH$_2$CH$_2$CH$_2$CH$_2$-[4-piperidinyl]-N-CH(4-Cl-C$_6$H$_4$)(4-Cl-C$_6$H$_4$) |
| 117 | H | 0 | CH$_2$CH$_2$CH$_2$ | H | CH$_2$CH$_2$CH$_2$CH$_2$-[4-piperidinyl]-N-CH(4-Cl-C$_6$H$_4$)(4-Cl-C$_6$H$_4$) |
| 118 | H | 0 | CH$_2$CH$_2$ | H | CH$_2$CH$_2$CH$_2$CH$_2$-[4-piperidinyl]-N-CH(2-Cl-C$_6$H$_4$)(2-Cl-C$_6$H$_4$) |
| 119 | H | 0 | cyclopropyl | H | CH$_2$CH$_2$CH$_2$CH$_2$-[4-piperidinyl]-N-CH(2-Cl-C$_6$H$_4$)(2-Cl-C$_6$H$_4$) |
| 120 | H | 0 | CH$_2$CH$_2$CH$_2$CH$_2$ | H | CH$_2$CH$_2$CH$_2$CH$_2$-[4-piperidinyl]-N-CH(2-Cl-C$_6$H$_4$)(2-Cl-C$_6$H$_4$) |

TABLE 1-continued
Exemplifying compounds of formula (I) according to the invention
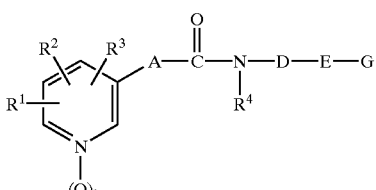
| Nr | R¹ | k | A | R⁴ | D-E-G |
|---|---|---|---|---|---|
| 121 | H | 0 | CH₂CH₂ | H | 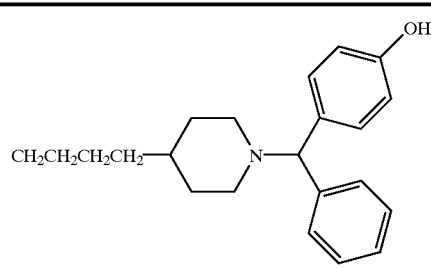 |
| 122 | H | 0 | CH₂CH₂CH₂CH₂ | H | 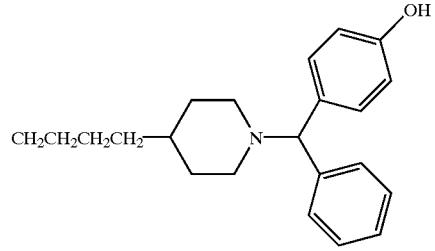 |
| 123 | H | 0 | CH₂CH₂ | H | 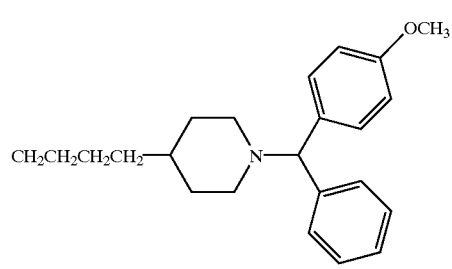 |
| 124 | H | 0 | CH₂CH₂CH₂CH₂ | H | 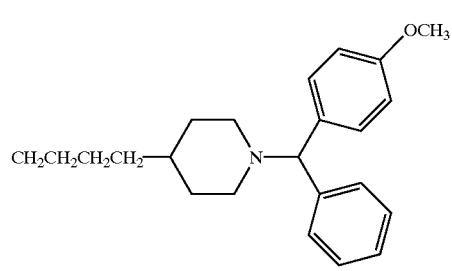 |
| 125 | H | 0 | CH₂CH₂ | H | 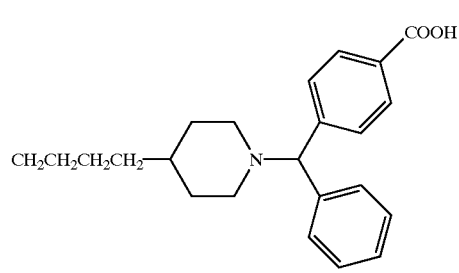 |

TABLE 1-continued
Exemplifying compounds of formula (I) according to the invention
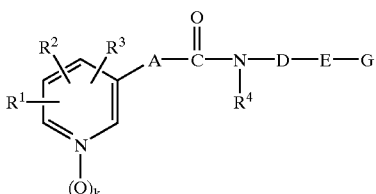
| Nr | R¹ | k | A | R⁴ | D-E-G |
|----|----|----|---|----|-------|
| 126 | H | 0 | $CH_2CH_2$ | H | 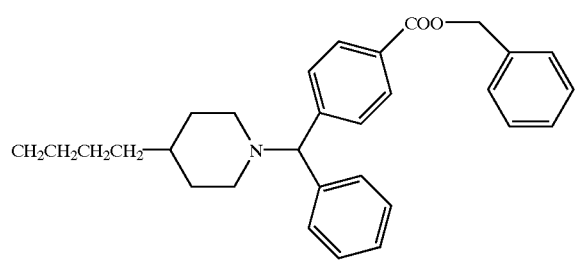 |
| 127 | H | 0 | $CH_2CH_2$ | H | 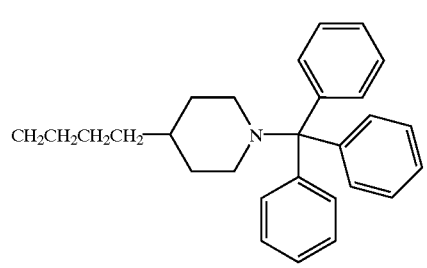 |
| 128 | H | 0 | $CH_2CH_2CH_2CH_2$ | H | 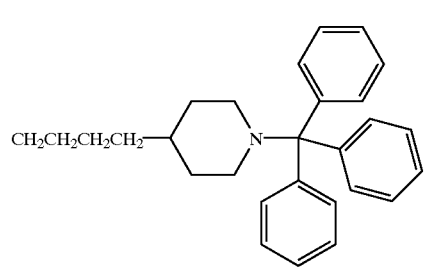 |
| 129 | H | 0 | $CH_2CH_2$ | H | 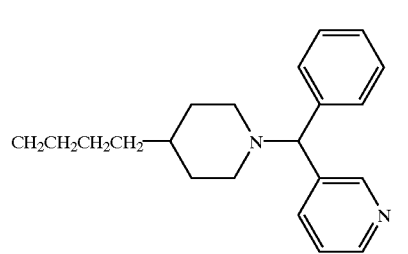 |
| 130 | H | 0 | $CH_2CH_2CH_2CH_2$ | H | 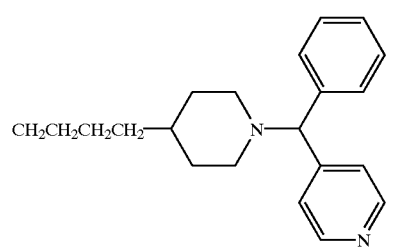 |

TABLE 1-continued
Exemplifying compounds of formula (I) according to the invention
| Nr | R¹ | k | A | R⁴ | D-E-G |
|---|---|---|---|---|---|
| 131 | H | 0 | CH₂CH₂ | H | 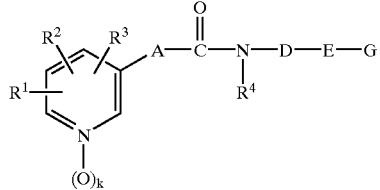 |
| 132 | H | 0 | CH₂CH₂CH₂CH₂ | H | 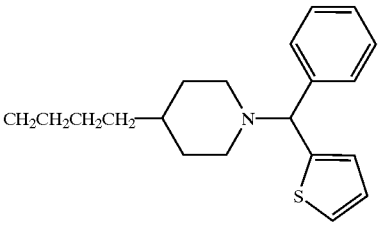 |
| 133 | H | 0 | CH₂CH₂ | H | 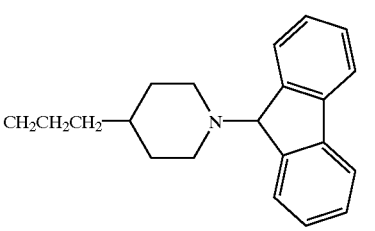 |
| 134 | 5-F | 0 | CH₂CH₂ | H | 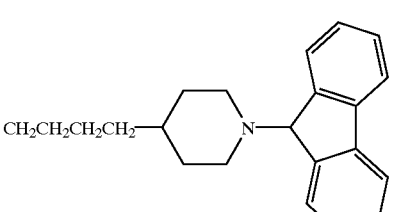 |
| 135 | H | 0 | CH₂CH₂ | H | 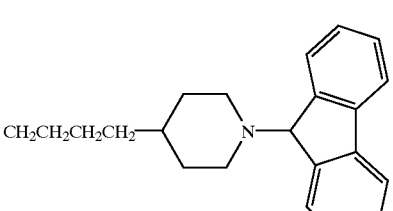 |

TABLE 1-continued
Exemplifying compounds of formula (I) according to the invention
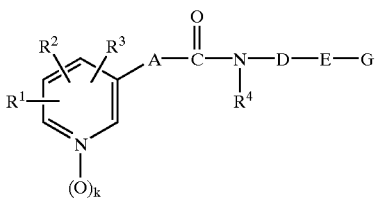
| Nr | R¹ | k | A | R⁴ | D-E-G |
|---|---|---|---|---|---|
| 136 | H | 0 | CH₂CH₂CH₂CH₂ | H | 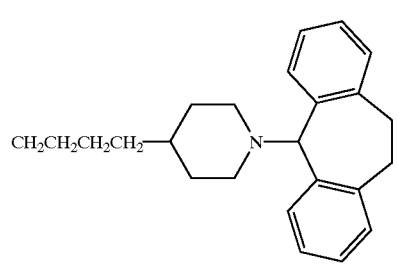 |
| 137 | H | 0 | CH₂CH₂ | H | 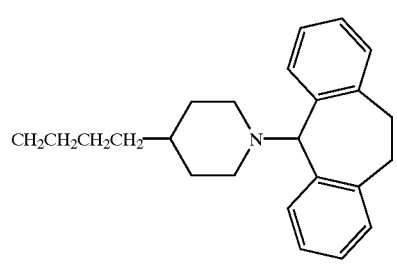 |
| 138 | H | 0 | CH₂CH₂ | H | 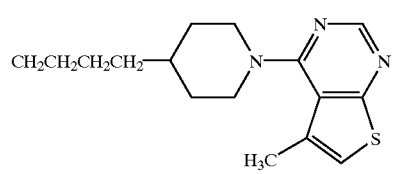 |
| 139 | H | 0 | CH₂CH₂CH₂CH₂ | H | 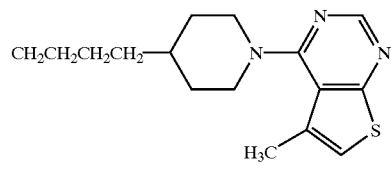 |
| 140 | H | 0 | CH₂CH₂ | H | 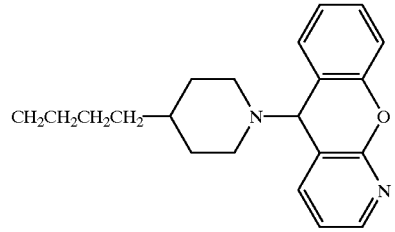 |

TABLE 1-continued
Exemplifying compounds of formula (I) according to the invention
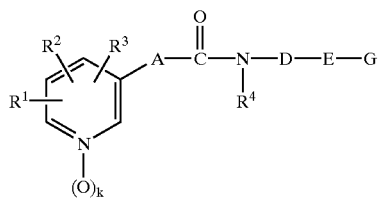
| Nr | R¹ | k | A | R⁴ | D-E-G |
|---|---|---|---|---|---|
| 141 | H | 0 | CH₂CH₂ | H | |
| 142 | H | 0 | CH₂CH₂ | H | |
| 143 | H | 0 | CH₂CH₂CH₂CH₂ | H | |
| 144 | H | 0 | CH₂CH₂ | H | |
| 145 | H | 0 | CH₂CH₂ | H | |
| 146 | H | 0 | CH₂CH₂ | H | |
| 147 | H | 0 | CH₂CH₂ | H | |

TABLE 1-continued
Exemplifying compounds of formula (I) according to the invention
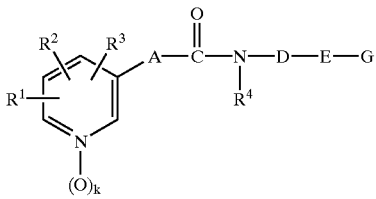
| Nr | R¹ | k | A | R⁴ | D-E-G |
|---|---|---|---|---|---|
| 148 | H | 0 | (CH$_2$)$_5$ | H | 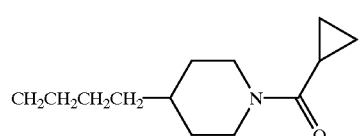 |
| 149 | H | 0 | CH$_2$CH$_2$ | H | 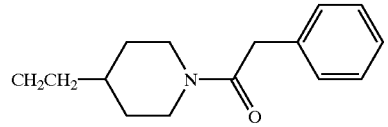 |
| 150 | H | 0 | CH$_2$CH$_2$ | H | 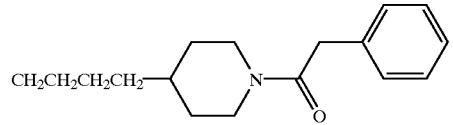 |
| 151 | H | 0 | CH$_2$CH$_2$CH$_2$CH$_2$ | H | 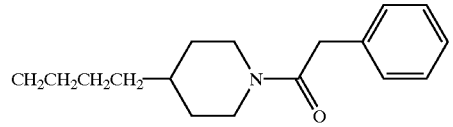 |
| 152 | H | 0 | CH$_2$CH$_2$CH$_2$ | H | 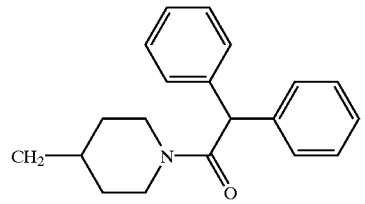 |
| 153 | H | 0 | CH$_2$CH$_2$ | H | 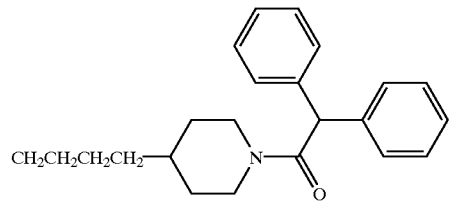 |
| 154 | H | 0 | CH$_2$CH$_2$ | H | 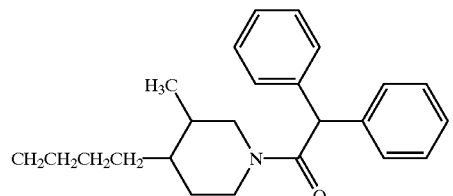 |

TABLE 1-continued
Exemplifying compounds of formula (I) according to the invention
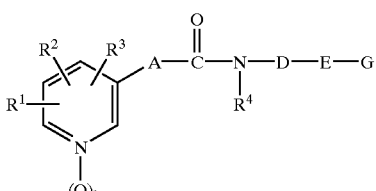
| Nr | R¹ | k | A | R⁴ | D-E-G |
|---|---|---|---|---|---|
| 155 | H | 0 | SCH₂CH₂ | H | 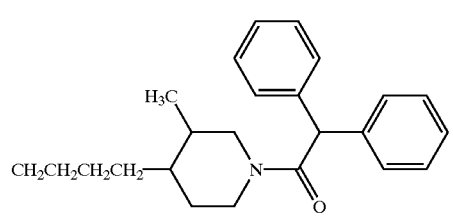 |
| 156 | H | 0 | CH₂CH₂ | H | 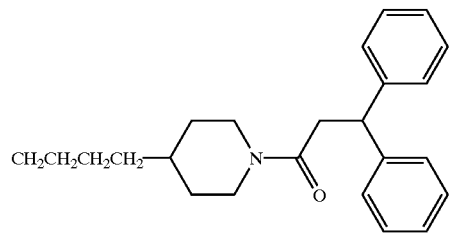 |
| 157 | H | 0 | CH₂CH₂CH₂CH₂ | H | 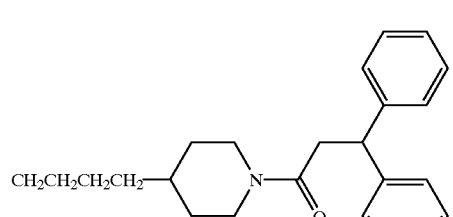 |
| 158 | H | 0 | CH₂CH₂ | H | 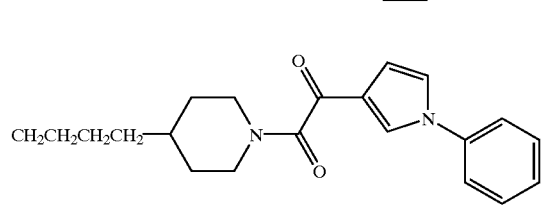 |
| 159 | H | 0 | CH₂CH₂ | H | 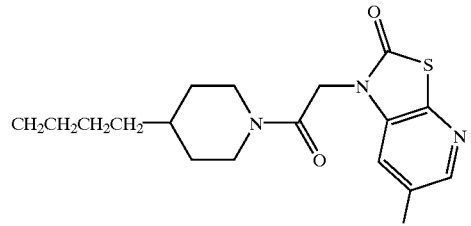 |

TABLE 1-continued
Exemplifying compounds of formula (I) according to the invention
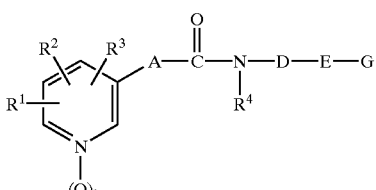
| Nr | R¹ | k | A | R⁴ | D-E-G |
|---|---|---|---|---|---|
| 160 | H | 0 | CH₂CH₂CH₂CH₂ | H | 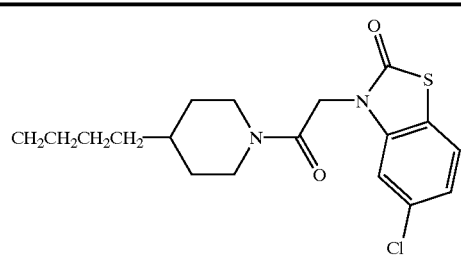 |
| 161 | H | 0 | CH₂ | H | 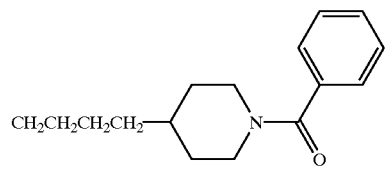 |
| 162 | H | 0 | CH₂CH₂ | H | 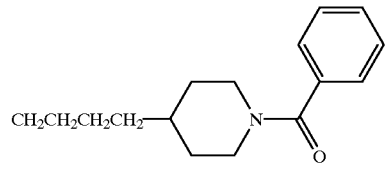 |
| 163 | H | 0 | CH₂CH₂CH₂CH₂ | H | 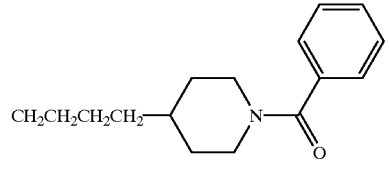 |
| 164 | H | 0 | CH₂CH₂ | H | 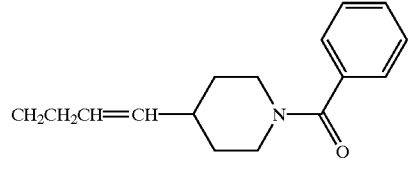 |
| 165 | H | 0 | CH₂CH₂ | CH₃ | 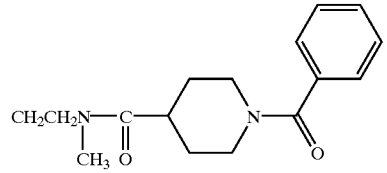 |
| 166 | H | 0 | CH₂CH₂ | H | 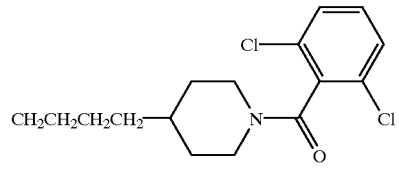 |

TABLE 1-continued
Exemplifying compounds of formula (I) according to the invention
| Nr | R¹ | k | A | R⁴ | D-E-G |
|---|---|---|---|---|---|
| 167 | H | 0 | CH₂CH₂ | H | 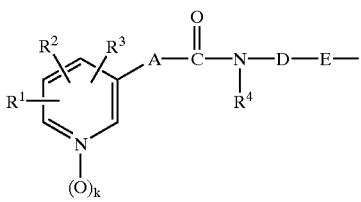 |
| 168 | H | 0 | CH₂CH₂ | H | 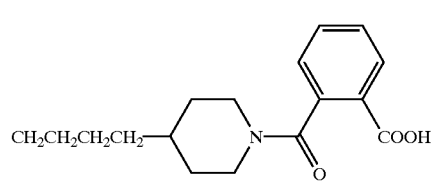 |
| 169 | H | 0 | CH₂CH₂CH₂CH₂ | H | 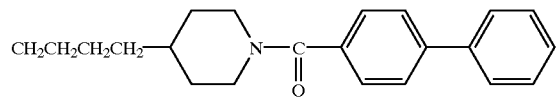 |
| 170 | H | 0 | CH₂CH₂ | H | 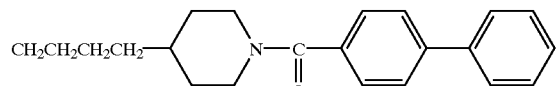 |
| 171 | H | 0 | CH₂CH₂CH₂ | H | 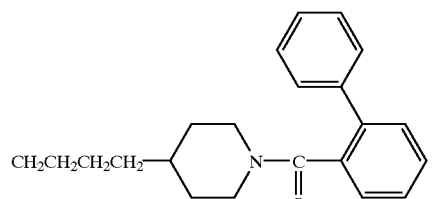 |
| 172 | H | 0 | CH₂CH₂ | H | 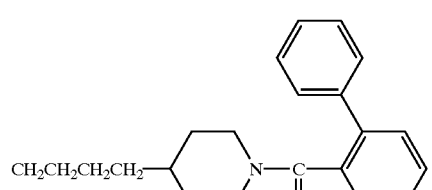 |
| 173 | 2-F | 0 | CH₂CH₂ | H | 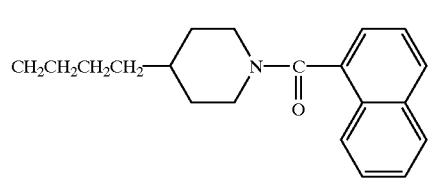 |

TABLE 1-continued

Exemplifying compounds of formula (I) according to the invention

| Nr | R¹ | k | A | R⁴ | D-E-G |
|----|----|----|----|----|-------|
| 174 | H | 0 | CH$_2$CH$_2$ | H | (CH$_2$)$_8$-piperidine-N-C(O)-1-naphthyl |
| 175 | H | 0 | CH$_2$CH$_2$ | H | CH$_2$CH$_2$CH$_2$CH$_2$-piperidine-N-C(O)-2-naphthyl |
| 176 | H | 0 | CH$_2$CH$_2$CH$_2$CH$_2$ | H | CH$_2$CH$_2$CH$_2$CH$_2$-piperidine-N-C(O)-2-naphthyl |
| 177 | H | 0 | CH$_2$CH$_2$ | H | CH$_2$CH$_2$CH$_2$CH$_2$-piperidine-N-C(O)-(9-oxofluoren-4-yl) |
| 178 | H | 0 | CH$_2$CH$_2$CH$_2$CH$_2$ | H | CH$_2$CH$_2$CH$_2$CH$_2$-piperidine-N-C(O)-(9-oxofluoren-4-yl) |
| 179 | H | 0 | CH$_2$CH$_2$ | H | (CH$_2$)$_6$-piperidine-N-C(O)-(9-oxofluoren-4-yl) |
| 180 | H | 0 | CH$_2$CH$_2$ | H | CH$_2$CH$_2$CH$_2$CH$_2$-piperidine-N-C(O)-(9,10-dioxoanthracen-2-yl) |

TABLE 1-continued
Exemplifying compounds of formula (I) according to the invention
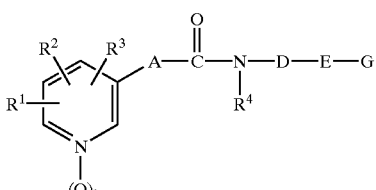
| Nr | R¹ | k | A | R⁴ | D-E-G |
|---|---|---|---|---|---|
| 181 | 4-F | 0 | $CH_2CH_2$ | H | 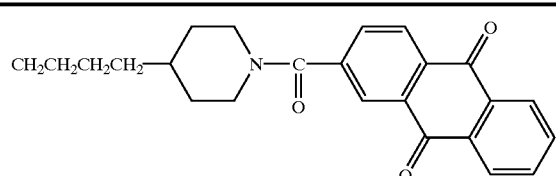 |
| 182 | H | 0 | $CH_2CH_2CH_2CH_2$ | H | 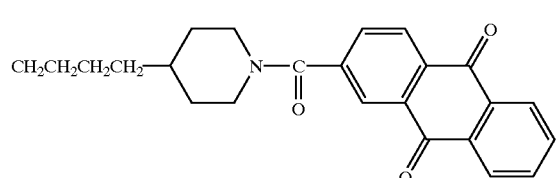 |
| 183 | H | 0 | $CH_2CH_2$ | H | 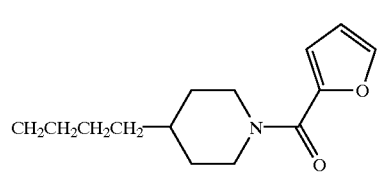 |
| 184 | H | 0 | $CH_2CH_2$ | H | 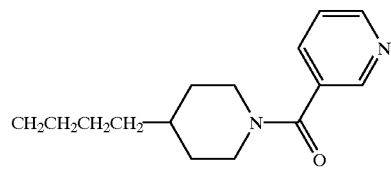 |
| 185 | H | 0 | $(CH_2)_5$ | H | 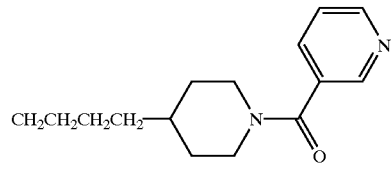 |
| 186 | H | 0 | $CH_2CH_2$ | H | 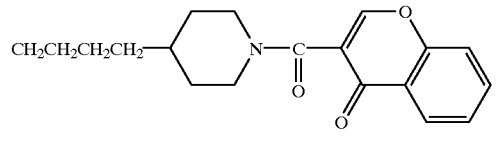 |
| 187 | H | 0 | $CH_2CH_2CH_2CH_2$ | H | 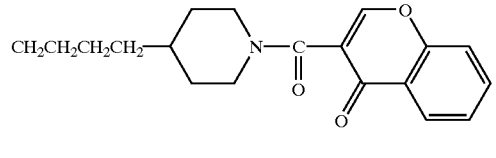 |
| 188 | H | 0 | $CH_2CH_2$ | H | 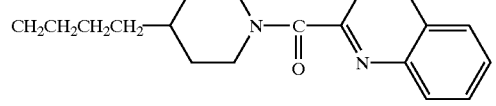 |

TABLE 1-continued

Exemplifying compounds of formula (I) according to the invention

| Nr | R¹ | k | A | R⁴ | D-E-G |
|---|---|---|---|---|---|
| 189 | H | 0 | SCH$_2$CH$_2$ | H | CH$_2$CH$_2$CH$_2$CH$_2$-piperidine-C(O)-quinoxalin-2-yl |
| 190 | H | 0 | CH$_2$CH$_2$ | H | CH$_2$CH$_2$CH$_2$CH$_2$-piperidine-C(O)-N(CH$_3$)$_2$ |
| 191 | H | 0 | CH$_2$CH$_2$ | H | CH$_2$CH$_2$CH$_2$CH$_2$-piperidine-C(O)-N(CH(CH$_3$)$_2$)$_2$ |
| 192 | H | 0 | CH$_2$CH$_2$ | H | CH$_2$CH$_2$CH$_2$CH$_2$-piperidine-C(O)-N(CH$_2$C$_6$H$_5$)$_2$ |
| 193 | H | 0 | CH$_2$CH$_2$CH$_2$CH$_2$ | H | CH$_2$CH$_2$CH$_2$CH$_2$-piperidine-C(O)-NH-CH$_2$-(2-furyl) |
| 194 | H | 0 | CH$_2$CH$_2$ | H | CH$_2$CH$_2$CH$_2$CH$_2$-piperidine-C(O)-NH-(1-naphthyl) |
| 195 | 2-Cl | 0 | CH$_2$CH$_2$ | H | CH$_2$CH$_2$CH$_2$CH$_2$-piperidine-C(O)-NH-(1-naphthyl) |

TABLE 1-continued
Exemplifying compounds of formula (I) according to the invention
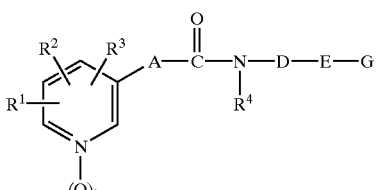
| Nr | R¹ | k | A | R⁴ | D-E-G |
|---|---|---|---|---|---|
| 196 | H | 0 | CH₂CH₂ | H | 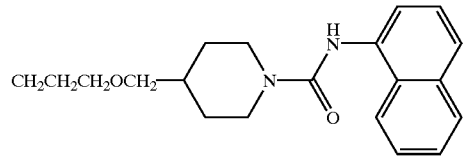 |
| 197 | H | 0 | CH₂CH₂ | H | 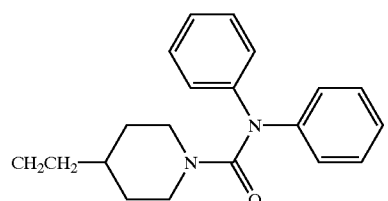 |
| 198 | H | 0 | CH₂CH₂CH₂CH₂ | H | 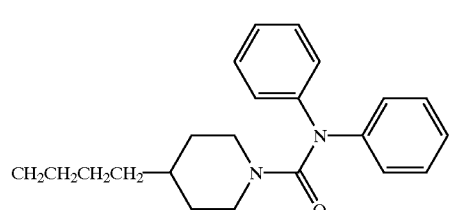 |
| 199 | H | 0 | CH₂CH₂ | H | 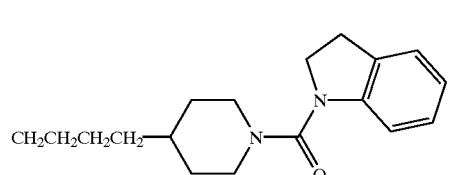 |
| 200 | H | 0 | CH₂CH₂CH₂CH₂ | H | 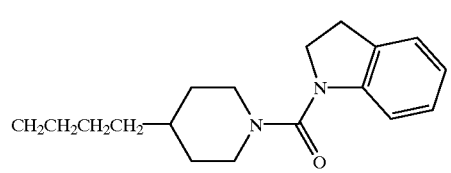 |
| 201 | H | 0 | CH₂CH₂ | H | 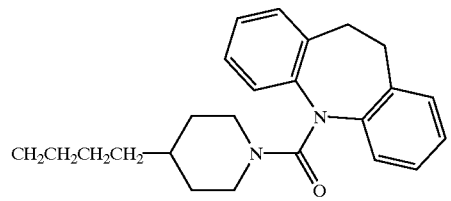 |

TABLE 1-continued

Exemplifying compounds of formula (I) according to the invention

| Nr | R¹ | k | A | R⁴ | D-E-G |
|---|---|---|---|---|---|
| 202 | H | 0 | CH₂CH₂CH₂CH₂ | H | CH₂CH₂CH₂CH₂-[piperidine-N]-C(O)-N(dibenzo[b,f][1,4]diazepine-10,11-dihydro) |
| 203 | H | 0 | CH₂CH₂ | H | CH₂CH₂CH₂CH₂-[piperidine-N]-C(O)-N(dibenzo[b,f]azocine) |
| 204 | H | 0 | CH₂CH₂CH₂CH₂ | H | CH₂CH₂CH₂CH₂-[piperidine-N]-C(O)-N(dibenzo[b,f]azocine) |
| 205 | H | 0 | CH₂CH₂ | H | CH₂CH₂CH₂CH₂-[piperidine]-N-SO₂-CH₃ |
| 206 | H | 0 | CH₂CH₂CH₂CH₂ | H | CH₂CH₂CH₂CH₂-[piperidine]-N-SO₂-CH₃ |
| 207 | H | 0 | CH₂CH₂ | H | CH₂CH₂CH₂NH-[piperidine]-N-SO₂-CH₃ |
| 208 | H | 0 | CH₂CH₂ | H | CH₂-[piperidine]-N-SO₂-C₆H₄-CH₃ |
| 209 | H | 0 | CH₂CH₂ | H | CH₂CH₂CH₂CH₂-[piperidine]-N-SO₂-C₆H₄-CH₃ |
| 210 | H | 0 | CH₂CH₂CH₂CH₂ | H | CH₂CH₂CH₂CH₂-[piperidine]-N-SO₂-C₆H₄-CH₃ |

TABLE 1-continued
Exemplifying compounds of formula (I) according to the invention
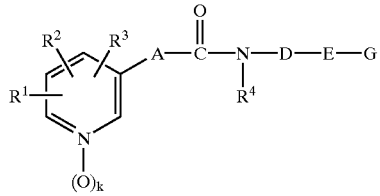
| Nr | R¹ | k | A | R⁴ | D-E-G |
|---|---|---|---|---|---|
| 211 | H | 0 | $CH_2CH_2$ | H | 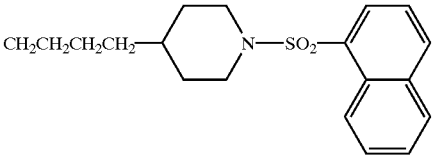 |
| 212 | H | 0 | $CH_2CH_2$ | H | 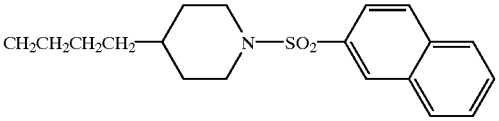 |
| 213 | H | 0 | △ | H | 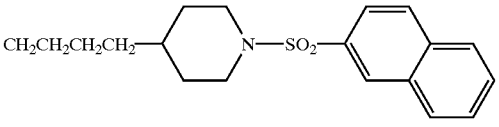 |
| 214 | H | 0 | $CH_2CH_2CH_2CH_2$ | H | 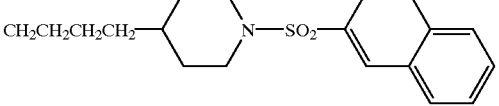 |
| 215 | H | 0 | $CH_2CH_2$ | H | 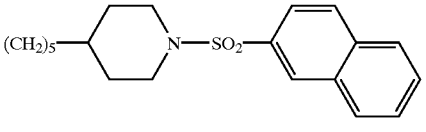 |
| 216 | H | 0 | $CH_2CH_2$ | H | 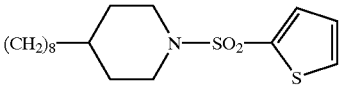 |
| 217 | 6-F | 0 | $CH_2CH_2$ | H | 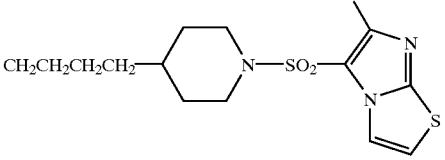 |
| 218 | H | 0 | $CH_2CH_2CH_2CH_2$ | H | 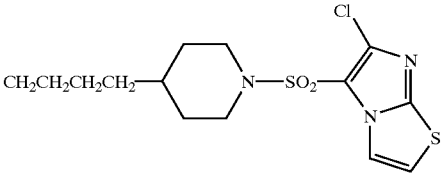 |

TABLE 1-continued
Exemplifying compounds of formula (I) according to the invention
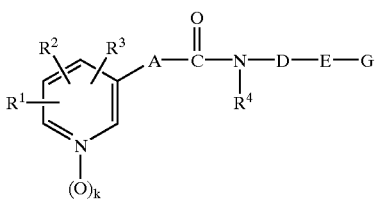
| Nr | R¹ | k | A | R⁴ | D-E-G |
|---|---|---|---|---|---|
| 219 | H | 0 | CH₂CH₂ | H | 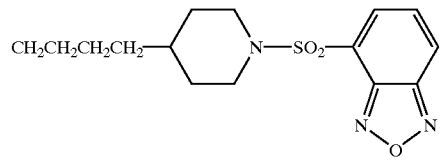 |
| 220 | H | 0 | CH₂CH₂ | H | 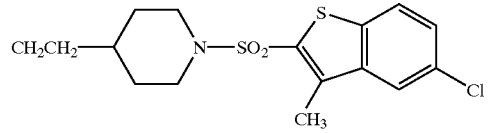 |
| 221 | H | 0 | CH₂CH₂ | H | 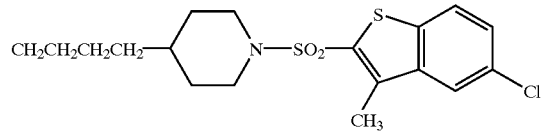 |
| 222 | H | 0 | CH₂CH₂CH₂ | H | 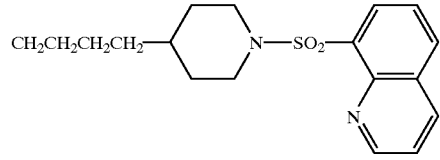 |
| 223 | H | 0 | CH₂CH₂ | H | 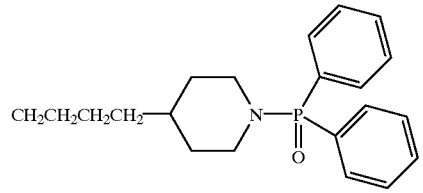 |
| 224 | H | 0 | CH₂CH₂CH₂CH₂ | H | 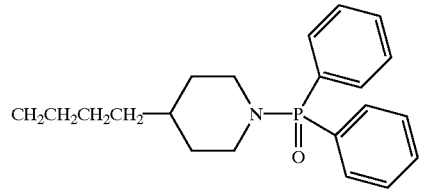 |
| 225 | H | 0 | CH₂CH₂ | H | 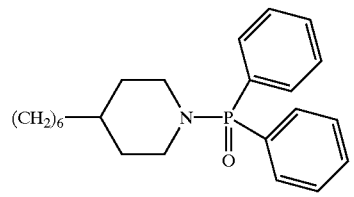 |

TABLE 1-continued

Exemplifying compounds of formula (I) according to the invention

| Nr | R¹ | k | A | R⁴ | D-E-G |
|---|---|---|---|---|---|
| 226 | H | 0 | CH₂CH₂ | H | CH₂CH₂CH₂CH₂-piperidine-N-C(O)-CF₃ |
| 227 | H | 0 | CH₂CH₂CH₂CH₂ | H | CH₂CH₂CH₂CH₂-piperidine-N-C(O)-CF₃ |
| 228 | H | 0 | CH₂CH₂ | H | CH₂CH₂CH₂CH₂-piperidine-N-C(O)-OCH₃ |
| 229 | H | 0 | CH₂CH₂ | H | CH₂CH₂CH₂CH₂-piperidine-N-C(O)-O-CH₂CH=CH₂ |
| 230 | H | 0 | CH₂CH₂ | H | CH₂CH₂-piperidine-N-C(O)-O-C(CH₃)₃ |
| 231 | H | 0 | CH₂CH₂ | H | CH₂CH₂CH₂CH₂-piperidine-N-C(O)-O-C(CH₃)₃ |
| 232 | H | 0 | cyclopropyl | H | CH₂CH₂CH₂CH₂-piperidine-N-C(O)-O-C(CH₃)₃ |
| 233 | H | 0 | CH₂CH₂CH₂CH₂ | H | CH₂CH₂CH₂CH₂-piperidine-N-C(O)-O-C(CH₃)₃ |
| 234 | H | 0 | CH₂CH₂ | H | CH₂CH₂CH₂CH=piperidine-N-C(O)-O-C(CH₃)₃ |
| 235 | H | 0 | CH₂CH₂ | H | CH₂CH=CHCH₂-piperidine-N-C(O)-O-C(CH₃)₃ |

TABLE 1-continued
Exemplifying compounds of formula (I) according to the invention
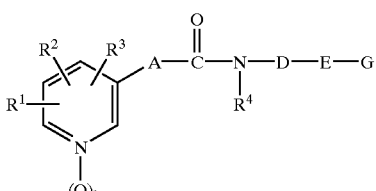
| Nr | R¹ | k | A | R⁴ | D-E-G |
|---|---|---|---|---|---|
| 236 | H | 0 | CH₂CH₂ | H | 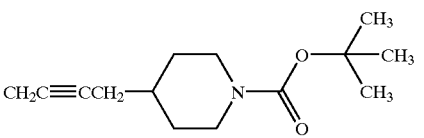 |
| 237 | H | 0 | CH₂CH₂ | H | 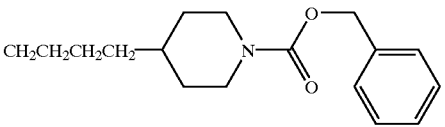 |
| 238 | H | 0 | CH₂CH₂CH₂CH₂ | H | 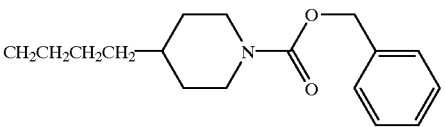 |
| 239 | H | 0 | CH₂CH₂ | H | 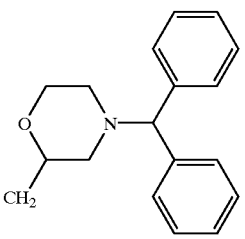 |
| 240 | H | 0 | CH₂CH₂CH₂CH₂ | H | 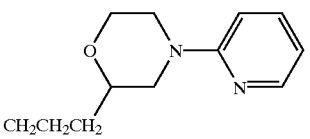 |
| 241 | H | 0 | CH₂CH₂ | H | 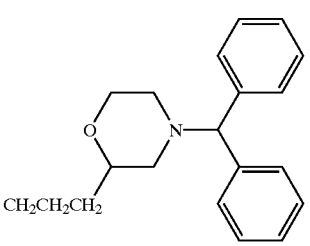 |

TABLE 1-continued
Exemplifying compounds of formula (I) according to the invention
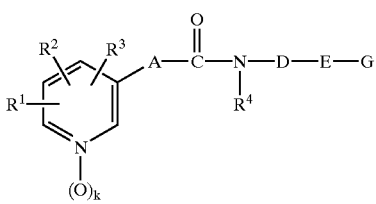
| Nr | R¹ | k | A | R⁴ | D-E-G |
|---|---|---|---|---|---|
| 242 | H | 0 | CH₂CH₂ | H | 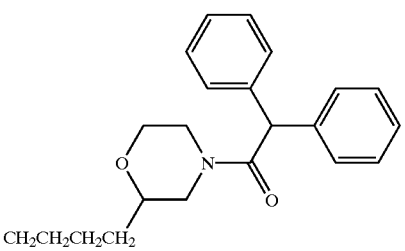 |
| 243 | H | 0 | CH₂CH₂ | H | 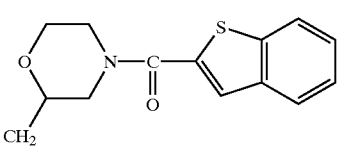 |
| 244 | H | 0 | CH₂CH₂CH₂CH₂ | H | 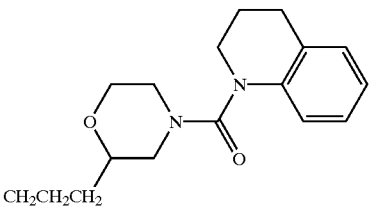 |
| 245 | H | 0 | CH₂CH₂ | H | 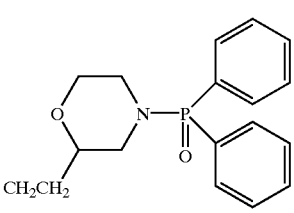 |
| 246 | H | 0 | CH₂CH₂CH₂CH₂ | H | 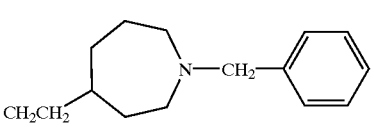 |
| 247 | 6-F | 0 | CH₂CH₂ | H | 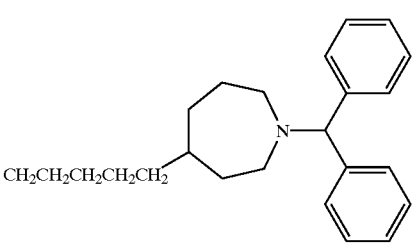 |

TABLE 1-continued
Exemplifying compounds of formula (I) according to the invention
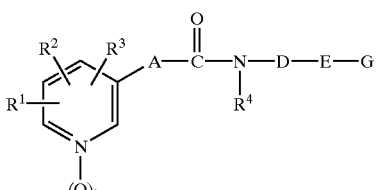
| Nr | R¹ | k | A | R⁴ | D-E-G |
|---|---|---|---|---|---|
| 248 | H | 0 | CH$_2$CH$_2$ | H | 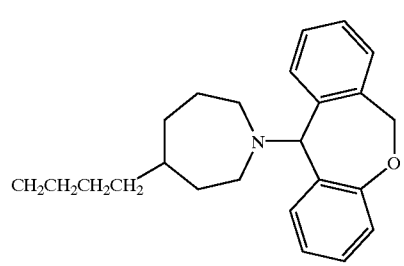 |
| 249 | H | 0 | CH$_2$CH$_2$ | H | 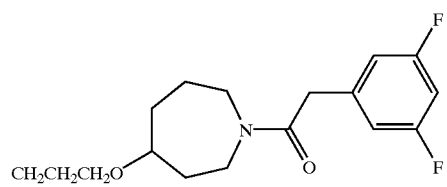 |
| 250 | H | 0 | CH$_2$CH$_2$CH$_2$CH$_2$ | H | 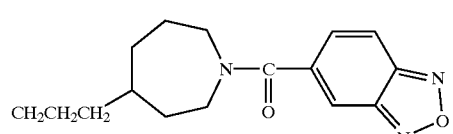 |
| 251 | H | 0 | △ | H | 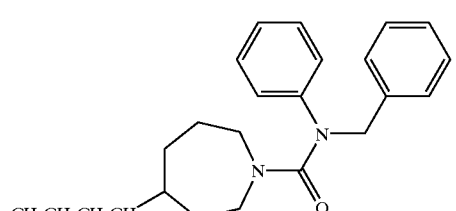 |
| 252 | H | 0 | CH$_2$CH$_2$ | H | 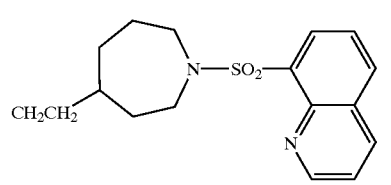 |
| 253 | H | 0 | CH$_2$CH$_2$ | H | 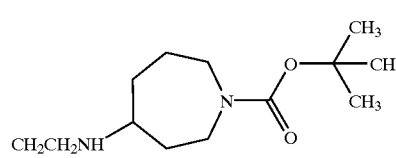 |

TABLE 1-continued

Exemplifying compounds of formula (I) according to the invention

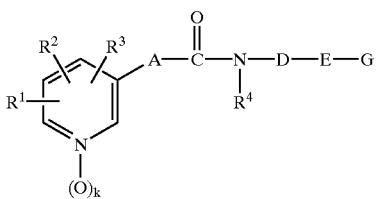

| Nr | R¹ | k | A | R⁴ | D-E-G |
|---|---|---|---|---|---|
| 254 | H | 0 | $CH_2CH_2$ | H | 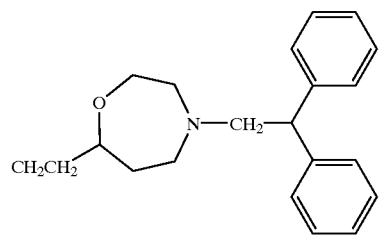 |
| 255 | H | 0 | $CH_2CH_2$ | H | 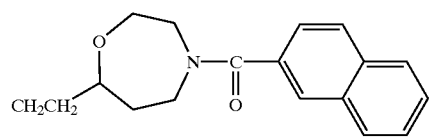 |
| 256 | H | 0 | $CH_2CH_2$ | H | 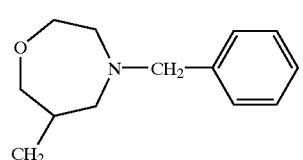 |
| 257 | H | 0 | $CH_2CH_2CH_2CH_2$ | H | 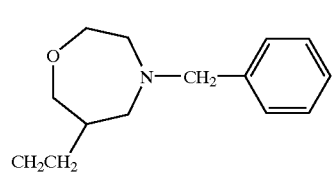 |

SYNTHESIS METHODS

Further subject-matter of the invention are analogous methods for the production of the compounds of formula (I) according to the invention.

Method (A):

Compounds of formula (I) are (a) obtained by reacting carboxylic acids of formula (II)

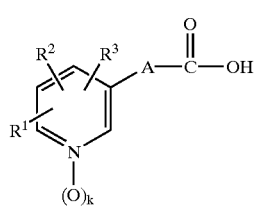
(II)

in which R¹, R², R³, A and k have the meaning described above or their reactive derivatives are reacted with compounds of formula (III)

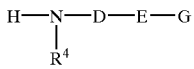
(III)

wherein D, E, G and R⁴ also have the above described meanings.

Reactive derivatives of compound (II) can be, for example, activated esters, anhydrides, acid halides (especially acid chlorides) or simple low alkyl esters. Suitable activated esters are, for example, p-nitrophenyl ester, 2,4,6-trichlorophenyl ester, pentachlorophenyl ester, cyanomethyl ester, esters of N-hydroxysuccinimide, of N-hydroxyphthalimides, of 1-hydroxybenzotriazol, of N-hydroxypiperidine, of 2-hydroxypyridine or of 2-mercaptopyridine, etc. Anhydrides can be symmetric anhydrides or mixed, as they are obtained, for example, with pivaloyl chloride or with chloroformates. Aromatic (for example chloroformic phenyl ester), araliphatic (for example chloroformic benzyl ester) or aliphatic chloroformates (for example chloroformic methyl ester, -ethyl ester or -isobutyl ester) can be used for this.

Reaction of compounds (II) with compounds (III) can also be carried out in the presence of condensation agents such as dicyclohexylcarbodiimide, 1-ethyl-3-(3-dimethylaminopropyl)carbodiimide hydrochloride, N,N'-carbonyldiimidazol, 1-ethoxycarbonyl-2-ethoxy-1,2-dihydroquinoline, etc. If carbodiimides are used as the condensation agent, reagents such as N-hydroxysuccinimide, N-hydroxyphthalimide, 1-hydroxybenzotriazol, N-hydroxypiperidine, etc. can be advantageously added.

Compounds of formula (III) can be used for reaction as free bases as well as in the form of their acid addition salts. For this, the salts of inorganic acids are to be preferred, i.e. hydrochlorides, hydrobromides or sulfates.

Reaction of compounds (II) or their reactive derivatives with compounds (III) are normally carried out in a suitable, preferably inert solvent. As examples, aromatic hydrocarbons such as benzene, toluene, xylene, halogenated hydrocarbons (for example dichloromethane, chloroform, 1,2-dichloroethane, trichloroethylene), ether (for example diethyl ether, tetrahydrofuran, dioxane, glycol dimethyl ether), ethyl acetate, acetonitrile or polar aprotic solvents such as, for example, dimethylsulfoxide, dimethylformamide or N-methylpyrrolidone are to be named. Pure solvents, as well as mixtures of two or more, can be used.

The reaction is optionally carried out in the presence of an auxiliary base. Suitable examples for this are alkali metal carbonates (sodium carbonate, potassium carbonate), alkali metal hydrogen carbonates (sodium hydrogen carbonate, potassium hydrogen carbonate), or organic bases such as, for example, triethylamine, ethyl diisopropylamine, tributylamine, N-methylmorpholine or pyridine. A suitable excess of compound (III) can also be used as a base. If compounds (III) are used in form of their acid addition salts, then it is appropriate to consider the amount of auxiliary base used as equivalent.

The reaction temperatures can - depending on reactivity of the educts—vary in a wide range. Generally, the reaction is carried out at temperatures between −40° C. and 180° C., preferably between −10° C. and 130° C., especially at the boiling point of the solvent used.

The starting compounds (II) and (III) are known and/or can be produced according to known methods in an analogous manner. Moreover, the production of representative examples is further described below.

Compounds of formula (I) can be (b) produced by reaction of compounds of formula (I), wherein G is hydrogen, and which themselves also have the activities found according to the invention, with a compound of formula (IV),

L—G    (IV)

in which G has the meaning given above, with the exception of hydrogen, and L represents a suitable nucleofuge or reactive group. The type of nucleofuge or reactive group L and the conditions of the reaction are dependent of the nature of group G.

Compounds of formula (I), in which G, with the exception of hydrogen, has the meaning of (G1) according to the above definition can, aside from method (a), also be (c) produced by reacting compounds of formula (I), in which G is hydrogen, with a suitable alkylation agent and/or arylation agent of formula (IV), wherein G is an alkyl-, alkenyl-, alkinyl-, cycloalkyl-, aryl-, aralkyl-, heteroaryl- or heteroaralkyl residue and the leaving group L can represent a reactive derivative of an alcohol, for example, a halogen atom such as chlorine, bromine or iodine or a sulfonic acid ester, i.e. for example a methanesulfonyloxy-, trifluoromethanesulfonyloxy-, ethanesulfonyloxy-, benzenesulfonyloxy-, p-toluenesulfonyloxy-, p-bromobenzenesulfonyloxy- or m-nitrobenzenesulfonyloxy residue, etc. or a reactive group L can also be an epoxide group, wherein the reaction occurs under addition.

The reaction of compounds (I), in which G is a hydrogen, and (IV) is usually conducted in a suitably inert solvent. As solvents of this type, aromatic hydrocarbons (benzene, toluene, xylene), ethers (for example tetrahydrofuran, dioxane, glycol dimethyl ether), ethyl acetate, acetonitrile, ketones (acetone, ethyl methyl ketone), polar protic solvents such as alcohols (ethanol, isopropanol, butanol, glycol monomethyl ether) or polar aprotic solvents such as, for example, dimethylsulfoxide, dimethylformamide or N-methylpyrrolidone can be considered. Pure solvents as well as mixtures of two or more can also be used. Preferably, the reactions are carried out in the presence of bases, whereby said bases can be used as in method (a) above. If chlorides or bromides are used as compound (IV), the reaction can be accelerated by the addition of alkali metal iodides (sodium iodide, potassium iodide). The reaction temperatures can vary between 0° C. and 180° C. depending on the reactivity of the educts, but preferably lie between 20° C. and 130° C.

Compounds of formula (I), in which G represents an acyl residue, a carbamoyl residue, a sulfonyl residue or a phosphinoyl residue according to the above definition, can also be produced, aside from the above method (a), (d) by reacting compounds of formula (I), wherein G is hydrogen, with a carboxylic acid, carbamic acid, sulfonic acid and/or phosphinic acid of formula (V),

HO—G    (V)

wherein G is an acyl residue, carbamoyl residue, sulfonyl residue or phosphinoyl residue according to definition, or their derivatives capable of reaction. Preferred derivatives of carboxylic acids and/or sulfonic acids (V) which are capable of reaction are symmetric or unsymmetric carboxylic acid anhydrides and/or sulfonic acid anhydrides or acyl- and/or sulfonyl halides, especially acyl- and/or sulfonyl chlorides. Preferably, derivatives of carbamates and/or phosphinic acids which are capable of reaction are the carbamoyl halides and/or phosphinyl halides, especially carbamyl- and/or phosphinyl chlorides. The reaction of the acids (V) and/or their reactive derivatives with compounds (I), in which G is hydrogen, preferably occurs in the presence of auxiliary bases in solvents and under conditions as they are described in method (a).

Compounds of formula (I), wherein G represents a carbamoyl residue according to the definition (G2b) with the proviso that r=0, the grouping is

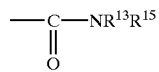

can also be produced, aside from the methods (a) and (d)

(e) by reacting compounds of formula (I), in which G is hydrogen with a carbonyl group transmitter to an intermediate product and subsequently reacting this directly with a primary or secondary amine with the formula (VI)

H—NR$^{13}$R$^{15}$ (VI)

wherein R$^{13}$ and R$^{15}$ and/or the grouping —NR$^{13}$R$^{15}$ have the meanings according to the above definitions without having to purify or isolate the intermediate product.

To-trichloromethyl carbonate (triphosgene) and carbonyldiimidazol have been proven as particularly reactive carbonyl group transmitters. The reaction of compounds of formula (I), wherein G is hydrogen, with triphosgene and/or carbonyldiimidazol are typically conducted in an absolute, inert solvent in the presence of a tertiary organic amine as an auxiliary base in such a manner that the solution of compounds (I) and the auxiliary base are slowly poured into a solution of an equivalent amount of carbonyl group transmitter. Thereby, the reaction requires molar ratios of 1:1 for the reaction of compound (I) and carbonyldiimidazol, and, in contrast, a ratio of 1:0.35 for the use of triphosgene. After complete reaction of the components to the intermediate product, compound (VI) is added in stochiometric amounts or in excess as a solution or a solid and the reaction is typically completed at elevated temperature. Suitable inert solvents are, for example hydrocarbons such as hexane, heptane, benzene, toluene, xylene, chlorinated hydrocarbons (for example dichloromethane, chloroform, 1,2-dichloroethane, trichloroethylene), ethers (for example diethyl ether, tetrahydrofuran, dioxane), esters such as ethyl acetate, butyl acetate, acetonitrile or polar aprodic solvents such as formamide or dimethylformamide. Pure solvents as well as mixtures can be used diversely. Sometimes it is of advantage to carry out the first partial reaction at low temperature in a low-viscosity, highly-volatile solvent and to remove the solvent after formation of the intermediate and replace it by a higher boiling solvent.

Amines such as for example triethylamine, ethyl diisopropylamine, tributylamine, N-methylmorpholine or pyridine are suitable as auxiliary bases. If compounds (I) or (VI) are used as salts, the amount of the auxiliary base is increased accordingly. The reaction temperatures can lie in between −40° C. and 50° C. for the first partial reaction, preferably at 0° C. to 30° C., and between 0° C. and 150° C. for the second partial reaction, preferably at 20° C. to 120° C.

Compounds of formula (I), wherein G represents a carbamoyl residue according to the definition (G2b) with the proviso that r=0 and R$^{15}$=hydrogen, the grouping is

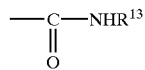

can also be produced, aside from methods (a), (d) and (e)

(f) by reacting the compounds of formula (I) in which G is hydrogen, with an isocyanate of formula (VII) in which R$^{13}$ has the meaning according to the above definition

O=C=N—R$^{13}$ (VII).

Reaction of the compounds of formula (I), in which G is hydrogen, with the isocyanates of formula (VII) are conducted thereby in an absolute, inert solvent which can be a hydrocarbon such as pentane, hexane, heptane, benzene, toluene, or xylene, chlorinated hydrocarbons (such as dichloromethane, chloroform, 1,2-dichloroethane, trichloroethylene), ethers (for example, diethyl ether, tetrahydrofuran, dioxane), esters such as ethyl acetate, butyl acetate, or polar aprotic solvents such as formamide or dimethylformamide. Mixtures of various solvents can also be used. Thereby, the reaction temperatures can vary in the region from −20° C. to 150° C., but preferably lie at 20° C. to 100° C.

As already mentioned, the compounds of formula (I), wherein G is hydrogen, are themselves compounds with tumor growth inhibiting activity and/or cytostatic and immunosuppressive effectiveness. However, independent of their therapeutic applicability, they also represent useful intermediate compounds for the production of a multitude of other compounds according to the invention corresponding to (c) to (f).

They themselves can, in principle, be produced according to method A by reacting a carboxylic acid of formula (II) with amines of formula (III) in which G is hydrogen as described above. However, since the compounds of formula (III) with hydrogen as G represent α,ω-diamines, the formation of product mixtures is always to be expected in their reaction with carboxylic acids (II) or their reactive derivatives making a subsequent separation necessary.

In contrast, compounds of formula (I), in which G is hydrogen, are essentially more advantageously produced from other compounds of formula (I), in which G is a selectively cleavable group under mild conditions, i.e. corresponds to a nitrogen protective group.

Among the compounds according to formula (I) with tumor growth inhibiting and/or cytostatic or immunomodulatory and/or immunosuppressive properties, are compounds in which G represents a 4-methoxybenzyl group, a triphenylmethyl group, a methoxy- and/or ethoxycarbonyl group, a tert-butoxycarbonyl group, an allyloxycarbonyl group or a trifluoroacetyl group.

Thus, compounds of formula (I) with benzyl-, diphenylmethyl-, triphenylmethyl-, or benzyloxycarbonyl groups as G are already catalytically converted at room temperature under mild conditions with elementary hydrogen or by transfer hydration in compounds of formula (I), wherein G is hydrogen.

Compounds of formula (I) with a 4-methoxybenzyl group are transformed into compounds of formula (I) wherein G is hydrogen by selective oxidation with ammonium-cer(IV)-nitrate.

The cleavage of simple alkoxycarbonyl groups such as the methoxy- or ethoxycarbonyl group as well as the trifluoroacetyl group as G in compounds of formula (I) succeed by alkali hydrolysis under mild conditions without cleaving the A and D linked amide function. This is suitably valid for the cleavage of the triphenylmethyl group and the tert-butoxycarbonyl group as G in compounds of formula (I), which occurs in acidic medium under mild conditions. Finally, compounds of formula (I) with an allyloxycarbonyl group as G can be converted into such with hydrogen as G in neutral medium with palladium catalyst.

The described methods are fully familiar to the person skilled in the art and are furthermore also documented in monographs (see for example Greene, Wuts, Protective Groups in Organic Synthesis, New York, 1991).

Compounds of formula (I), wherein R$^4$ is an alkyl, alkenyl, alkinyl or cycloalkyl residue according to the above definition can also be produced, aside from the methods (a) and (b), (g) by reacting compounds of formula (I), wherein R$^4$ is hydrogen, with a suitable alkylation agent of formula (VIII)

L—R$^4$ (VIII)

wherein R$^4$ is an alkyl, alkenyl, alkinyl or cycloalkyl residue according to the above definition and L is a suitable nucleofuge, i.e. for example a halogen atom such as chlorine, bromine or iodine or a sulfonic acid ester of an alcohol. Preferred sulfonic acid esters (VIII) contain a methylsulfonyloxy residue, trifluoromethanesulfonyloxy-, p-toluenesulfonyloxy-, p-bromobenzenesulfonyloxy- or m-nitrobenzenesulfonyloxy residue as L.

As an amide alkylation in the presence of tertiary amino groups, this reaction requires the use of strong auxiliary bases such as potassium-tert-butylate, sodium hydride, potassium hydride or butyl lithium in aprotic, inert solvents. Such solvents can be for example aliphatic or aromatic hydrocarbons (pentane, hexane, heptane, benzene, toluene), ethers (for example, tetrahydrofuran, dioxane) or polar solvents such as dimethylsulfoxide, dimethylformamide or N-methylpyrrolidone. Depending on the reactivity of the educts, the reaction temperatures can lie between −40° C. and 140° C. preferably between −20° C. and 80° C.

The compounds of formula (I) produced according to the methods (a) to (g) can be isolated and purified in a known manner, for example by subjecting the residue after distillation of the solvent to partition, extraction, re-precipitation or re-crystallization or another purification method. For this, column chromatography on a suitable support or preparative, middle or high pressure liquid chromatography are preferred for this.

The compounds (I) are first normally obtained in form of their free bases or their hydrates or solvates, depending on the type of isolation and purification. Their addition salts with pharmaceutically suitable acids are obtained in a typical manner by converting the base with the desired acid in a suitable solvent. Depending on the number of basic centers of compound (I), one or more equivalent acids per mole of base can be bound.

Suitable solvents are, for example, chlorinated hydrocarbons such as dichloromethane or chloroform; ethers such as diethyl ether, dioxane or tetrahydrofuran; acetonitrile; ketones such as acetone or ethyl methyl ketone; esters such as methyl acetate or ethyl acetate or low molecular alcohols such as methanol, ethanol or isopropanol; and water. Pure solvents as well as mixtures of two or three solvents can also be used. The salts can be isolated by crystallization, precipitation or the evaporation of the solvent. Thereby, they optionally accumulate as hydrates or solvates.

The bases can be recovered from the salts by alkalization, for example with aqueous ammonia solution, alkali carbonate or diluted sodium hydroxide solution.

The following listed compounds and/or their pharmaceutically acceptable salts are particularly preferred.

N-[4-(1-acetyl-piperidin-4-yl)-butyl]-3-(pyridin-3-yl)-propionamide,
N-[4-(1-benzoyl-piperidin-4-yl)-butyl]-3-(pyridin-3-yl)-propionamide,
N-[4-(1-diphenylacetyl-piperidin-4-yl)-butyl]-3-(pyridin-3-yl)-propionamide,
N-{4-[1-(9-oxo-9H-fluoren-4-carbonyl)-piperidin-4-yl]-butyl}-3-(pyridin-3-yl)-propionamide,
N-[4-(1-methylsulfonyl-piperidin-4-yl)-butyl]-3-(pyridin-3-yl)-propionamide,
N-{4-[1-(2-naphthyl-sulfonyl)-piperidin-4-yl]-butyl}-3-(pyridin-3-yl)-propionamide,
N-[4-(1-benzyl-piperidin-4-yl)-butyl]-3-(pyridin-3-yl)-propionamide,
N-(4-{1-[bis-(2-chlorophenyl)-methyl]-piperidin-4-yl}-butyl)-3-(pyridin-3-yl)-propionamide,
N-{4-[1-(phenyl-pyridin-3-yl-methyl)-piperidin-4-yl]-butyl}-3-(pyridin-3-yl)-propionamide,
N-{4-[1-(9H-fluoren-9-yl)-piperidin-4-yl]-butyl}-3-(pyridin-3-yl)-propionamide,
N-{4-[1-(6,11-dihydrodibenzo[b,e]oxepin-11-yl)-piperidin-4-yl]-butyl}-3-(pyridin-3-yl)-propionamide,
N-{4-[1-(1-naphthylaminocarbonyl)-piperidin-4-yl]-butyl}-3-(pyridin-3-yl)-propionamide,
N-[4-(1-diphenylaminocarbonyl-piperdin-4-yl)-butyl]-3-(pyridin-3-yl)-propionamide,
N-{4-[1-(10,11-dihydrodibenzo[b,f]azepin-5-yl-carbonyl)-piperidin-4-yl]-butyl}-3-(pyridin-3-yl)-propionamide,
N-[4-(1-diphenylphosphinoyl-piperidin-4-yl)-butyl]-3-(pyridin-3-yl)-propionamide,
N-[4-(1-diphenylmethyl-piperidin-4-yl)-butyl]-3-(2-fluorpyridin-3-yl)-propionamide,
N-[4-(1-diphenylmethyl-piperidin-4-yl)-butyl]-3-(5-fluorpyridin-4-yl)-propionamide,
N-[4-(1-diphenylmethyl-piperidin-4-yl)-butyl]-2,2-difluor-3-(pyridin-3-yl)-propionamide,
N-[4-(1-diphenylmethyl-piperidin-4-yl)-hexyl]-3-(pyridin-3-yl)-propionamide,
N-[2-(1-diphenylmethyl-piperidin-4-yl)-ethyl]-5-(pyridin-3-yl)-pentanoic acid amide,
N-[4-(1-diphenylmethyl-piperidin-4-yl)-butyl]-5-(pyridin-3-yl)-pentanoic acid amide,
N-[4-(1-diphenylmethyl-piperidin-4-yl)-butyl]-N-hydroxy-3-(pyridin-3-yl)-propionamide,
N-[4-(1-diphenylmethyl-piperidin-4-yl)-butyl]-2-hydroxy-3-(pyridin-3-yl)-propionamide,
N-[4-(1-diphenylmethyl-piperidin-4-yl)-butyl]-3-hydroxy-3-(pyridin-3-yl)-propionamide and
N-[4-(1-diphenylmethyl-piperidin-4-yl)-butyl]-3-(pyridin-3-yl)-propionamide.

SYNTHETIC EXAMPLES

For the End Products of the Invention According to Formula (I)

In the following production examples for the end products, the abbreviations stand for the following terms:
MP=melting point,
RT=room temperature,
THF=tetrahydrofuran,
DMF=dimethylformamide,
CDI=carbonyldiimidazol,
EDC=N-(3-dimethylaminopropyl)-N'-ethyl-carbodiimide hydrochloride,
HOBT=1-hydroxybenzotriazol,
TEA=triethylamine.
$^1$H-NMR-Spectrum=proton resonance spectrum, taken at 100 MHz. The chemical shifts are given in ppm against TMS as a standard ($\delta$=0.0), whereby
s=singlet,
d=doublet,
t=triplet,
dt=doublet-triplet,
m=multiplet,
ar=aromatic,
py=pyridine.

Example 1

N-[4-(1-Diphenylmethyl-piperidin-4-yl)-butyl]-2-(pyridin-3-yloxy)-acetamide (Substance 84)

5.0 g (32.6 mmol) 3-pyridyloxy acetic acid and 3.95 g (39.1 mmol) TEA are suspended in 200 ml absolute dichloromethane and cooled to ca. 0° C. under moisture exclusion. 6.34 g (41.3 mmol) 88% HOBT and 7.49 g (39.1 mmol) EDC are added and the mixture is stirred for 30 min under ice cooling 11.56 g (35.9 mmol) N-4-(1-diphenyl-methyl-piperidin-4-yl)-butylamine are dissolved in 50 ml absolute dichloromethane and added dropwise under ice cooling. The mixture is stirred at RT overnight without further cooling. Subsequently, the batch is washed once with 50 ml 1 M NaOH and twice, each with 70 ml water. The organic phase is dried over sodium sulfate and the solvent is removed under vacuum. The resinous residue is chromatographically purified over silica gel with $CHCl_3/CH_3OH$ (95/5 to 90/10) and crystallized from 30 ml acetic acid ethyl ester after drawing off the solvent. Colorless crystals with an MP of 103–105° C.; yield 3.45 g (23%).

$C_{29}H_{35}N_3O_2$ (457.6)

| IR-spectrum (KBr): | ν(NH) 3360 cm$^{-1}$ |
| --- | --- |
| | ν(C=O) 1660, 1540 cm$^{-1}$ |
| $^1$H-NMR-spectrum (CDCl$_3$): | 0.95–2.05(13H, m, piperidine, piperidine-(CH$_2$)$_3$) |
| | 2.70–3.00(2H, m, piperidine) |
| | 3.34(2H, dt, CONHCH$_2$, J=6.5Hz, J=12.9Hz) |
| | 4.21(1H, s, Ar$_2$CH) |
| | 4.51(2H, s, COCH$_2$O) |
| | 6.40–6.70(1H, m, NH) |
| | 7.00–7.60(12H, m, ar, py) |
| | 8.20–8.45 (2H, m, py) |

Example 2
N-[4-(1-Diphenylmethyl-piperidin-3-yl-carbonylamino)-butyl]-3-(pyridin-3-yl)-propionamide (Substance 106)

Production occurs analogously to example 1.

Batch size: 2.06 g (13.6 mmol) 3-(3-pyridyl)-propionic acid, 4.40 g (43.5 mmol) TEA, 2.40 g (14.1 mmol) 88% HOBT, 3.12 g (16.3 mmol) EDC and 5.48 g (15.0 mmol) 1-diphenylmethyl-piperidin-3-yl-carboxylic acid-(4-aminobutyl)-amide.

In the purification, this is chromatographed at first with $CHCl_3/CH_3OH$ (95/5) and subsequently crystallized from 60 ml acetonitrile. Colorless crystals with an MP of 159–161° C.; yield 3.2 g (47%).

$C_{31}H_{38}N_4O_2$ (498.7)

| IR-spectrum (KBr): | ν(NH) 3310 cm$^{-1}$ |
| --- | --- |
| | ν(C=O) 1640, 1560 cm$^{-1}$ |
| $^1$H-NMR-spectrum (CDCl$_3$): | 1.20–2.30(11H, m, piperidine, C—(CH$_2$)$_2$—C) |
| | 2.48(2H, t, CO—CH$_2$, J=7.5Hz) |
| | 2.60–2.90(2H, m, piperidine) |
| | 2.98(2H, t, py-CH$_2$, J=7.5Hz) |
| | 3.10–3.50(4H, m, CONHCH$_2$) |
| | 4.25(1H, s, Ar$_2$CH) |
| | 6.15–6.40(1H, m, NH) |
| | 7.10–7.65(12H, m, ar, py) |
| | 7.75–8.10(1H, m, NH) |
| | 8.35–8.55(2H, m, py) |

Example 3
N[-5-(1-Diphenylmethyl-piperidin-4-yl)-pentyl]-3-(pyridin-3-yl)-propionamide (Substance 101)

2.47 g (16.3 mmol) 3-(3-pyridyl)-propionic acid are suspended in 40 ml absolute dichloromethane and cooled to ca. 0° C. in an ice bath under moisture exclusion after addition of three drops pyridine. 1.90 ml (22.3 mmol) oxalyl chloride are slowly added, and the mixture is first stirred for 30 min under ice cooling and then at RT overnight. Subsequently, the solvent and excess oxalyl chloride are distilled on a rotary evaporator. In order to completely remove the oxalyl chloride, the colorless residue is dried for two hours under high-vacuum. The acid chloride obtained in this manner is suspended in 50 ml absolute dichloromethane without further purification and cooled to ca. 0° C. in an ice bath under moisture exclusion. 5.0 g (14.8 mmol) 5-(1-diphenylmethyl-piperidin-4-yl)-pentylamine are dissolved in 40 ml absolute dichloromethane and added dropwise to this suspension. After complete addition, the ice bath is removed, and the reaction is stirred for two hours at RT. The mixture is subsequently concentrated, taken up in 10% sodium hydroxide solution and extracted three times with acetic acid ethyl ester. The combined organic phases are washed with saturated NaCl-solution, dried over sodium sulfate and the solvent is removed under vacuum. The residue is chromatographically purified over silica gel with $CHCl_3/CH_3OH$ (96/4) and crystallized from 40 ml acetonitrile after drawing off the solvent. Colorless crystals with an MP of 112–114° C.; yield 3.5 g (50%).

$C_{31}H_{39}N_3O$ (469.7)

| IR-spectrum (KBr): | ν(NH) 3260 cm$^{-1}$ |
| --- | --- |
| | ν(C=O) 1635, 1550 cm$^{-1}$ |
| $^1$H-NMR-spectrum (CDCl$_3$): | 0.90–2.00(15H, m, piperidine, piperidine-(CH$_2$)$_4$) |
| | 2.44(2H, t, CO—CH$_2$, J=7.5Hz) |
| | 2.70–3.10(4H, m, piperidine, py-CH$_2$) |
| | 3.19(2H, dt, CONHCH$_2$, J=6.6Hz, J=12.6Hz) |
| | 4.21(1H, s, Ar$_2$CH) |
| | 5.30–5.60(1H, m, NH) |
| | 7.00–7.75(12H, m, ar, py) |
| | 8.35–8.65(2H, m, py) |

Example 4
N-[4-(1-Diphenylmethyl-piperidin-4-yl)-butyl]-3-(pyridin-3-yl)-propionamide (Substance 54)

21.6 g (131 mmol) 3-(3-pyridyl)-propionic acid methyl ester, 35.1 g (109 mmol) 4-(1-diphenylmethyl-piperidin-4-yl)-butylamine and 9.8 g (54.5 mmol) 30% sodium methylate solution in methanol are heated to boiling in 480 ml toluene for five hours. Subsequently, 30 ml of solvent is distilled off, sodium methylate precipitates thereby, and the temperature of the suspension increases under heavy foaming to 102° C. The mixture is cooled to 70–80° C. and extracted twice with 45 ml and 30 ml water. The organic phase is azeotropically dried in a moisture separator and cooled to ca. 0° C. The resulting precipitate is filtered and crystallized from 190 ml toluene. Colorless crystals with an MP of 139° C.; yield 46.3 g (93%).

$C_{30}H_{37}N_3O$ (455.6)

| IR-spectrum (KBr): | ν(NH) 3250 cm$^{-1}$ |
| --- | --- |
| | ν(C=O) 1630, 1570 cm$^{-1}$ |
| $^1$H-NMR-spectrum (CDCl$_3$): | 1.00–2.10(13H, m, piperidine, piperidine-(CH$_2$)$_3$) |
| | 2.43(2H, t, CO—CH$_2$, J=7.4Hz) |
| | 2.70–3.10(4H, m, piperidine, py-CH$_2$) |
| | 3.12(2H, dt, CONHCH$_2$, J=6.5Hz, J=12.5Hz) |

-continued 4.21(1H, s, Ar$_2$CH)
5.45–5.75(1H, m, NH)
7.05–7.60(12H, m, ar, py)
8.30–8.60(2H, m, py)

Example 5

N-{4-[1-(6,11-Dihydrodibenzo[b,e]oxepin-11-yl)-piperidin-4-yl-butyl}-3-(pyridin-3-yl)-propionamide (Substance 142)

3.46 g (15 mmol) 11-chloro-6,11-dihydrodibenzo[b,e]oxepine are dissolved in 90 ml absolute dichloromethane and 5.43 g (15 mmol) N-(4-piperidin-4-yl-butyl)-3-pyridin-3-yl-propionamide dihydrochloride is added. 5.0 g (49.5 mmol) TEA is dissolved in 20 ml absolute dichloromethane and added dropwise under ice cooling. The mixture is stirred for two days at RT without further cooling. Subsequently, the batch is washed twice, each with 50 ml water. The organic phase is dried over sodium sulfate and the solvent is removed under vacuum. The resinous residue is chromatographically purified over silica gel with CHCl$_3$/CH$_3$OH (95/5) and after drawing off the solvent, is first crystallized twice, each from 10 ml 1-chlorobutane and subsequently once from 10 ml acetic acid ethyl ester. Colorless crystals with a MP of 110–112° C. in a yield of 0.2 g (3%) are recovered.

C$_{31}$H$_{37}$N$_3$O$_2$ (483.6)

| IR-spectrum (KBr): | ν(NH) 3240 cm$^{-1}$ |
| --- | --- |
| | ν(C=O) 1630, 1570 cm$^{-1}$ |
| $^1$H-NMR-spectrum (CDCl$_3$): | 0.80–2.00(13H, m, piperidine, piperdine-(CH$_2$)$_3$) |
| | 2.43(2H, t, CO—CH$_2$, J=7.5Hz) |
| | 2.55–3.30(6H, m, piperidine, py-CH$_2$, CONHCH$_2$) |
| | 3.83(1H, s, Ar$_2$CH) |
| | 4.68(1H, d, O—CH, J=11.3Hz) |
| | 5.25–5.55(1H, m, NH) |
| | 6.65–7.65(11H, m, ar, py, O—CH) |
| | 8.35–8.60(2H, m, py) |

Example 6

N-[4-(1-Diphenylphosphinyl-piperidin-4-yl)-butyl]-3-(pyridin-3-yl)-propionamide (Substance 223)

3.4 ml (17.3 mmol) diphenylphosphinic acid chloride are dissolved in 100 ml absolute THF and cooled to ca. 0° C. under moisture exclusion. 5.0 g (17.3 mmol) N-(4-piperidin-4-yl-butyl)-3-(pyridin-3-yl)-propionamide and 4.8 ml (34.6 mmol) TEA are dissolved in 50 ml absolute THF and added dropwise under ice cooling. The mixture is stirred for three days at RT without further cooling. Subsequently, the solvent is removed under vacuum to a large extent and the residue is taken up in 100 ml 10% sodium hydroxide solution and extracted twice, each with 150 ml CHCl$_3$. The combined organic phases are washed with saturated NaCl-solution, dried over sodium sulfate and the solvent is removed under vacuum. The residue is chromatographically purified over silica gel with CHCl$_3$/CH$_3$OH (90/10) and crystallized from diisopropyl ether after drawing off the solvent. Colorless crystals with an MP of 134–135° C. yield 5.3 g (62%).

C$_{29}$H$_{36}$N$_3$O$_2$P (489.6)

| IR-spectrum (KBr): | ν(NH) 3240 cm$^{-1}$ |
| --- | --- |
| | ν(C=O) 1660, 1550 cm$^{-1}$ |
| $^1$H-NMR-spectrum (CDCl$_3$): | 0.90–1.90(11H, m, piperidine, piperidine-(CH$_2$)$_3$) |
| | 2.30–3.60(10H, m, piperidine, py-CH$_2$—CH$_2$, CONHCH$_2$) |
| | 6.35–6.70(1H, m, NH) |
| | 7.00–8.15(12H, m, ar, py) |
| | 8.25–8.70(2H, m, py) |

Example 7

N-[4-(1-Diphenylmethyl-piperidin-4-yl)-butyl]-5-(pyridin-3-yl)-pentanoic Acid Amide (Substance 90)

Production occurs analogously to example 3.

Batch size: 5.0 g (27.9 mmol) 5-(pyridin-3-yl)-pentanoic acid, 6.7 ml (76.1 mmol) oxalyl chloride and 8.2 g (25.3 mmol) 4-(1-diphenylmethyl-piperidin-4-yl)-butylamine.

During purification extraction is done three times, each with 100 ml CHCl$_3$ instead of acetic acid ethyl ester. The combined organic phases are washed twice, each with 50 ml saturated NaCl-solution. After chromatographic purification with CHCl$_3$/CH$_3$OH (95/5), this is crystallized from 70 ml acetic acid ethyl ester. Colorless crystals with an MP of 109° C.; yield 4.0 g (29%).

C$_{32}$H$_{41}$N$_3$O (483.7)

| IR-spectrum (KBr): | ν(NH) 3280 cm$^{-1}$ |
| --- | --- |
| | ν(C=O) 1630, 1545 cm$^{-1}$ |
| $^1$H-NMR-spectrum (CDCl$_3$): | 1.00–2.00(17H, m, piperidine, piperidine-(CH$_2$)3, C—CH$_2$—CH$_2$—C) |
| | 2.00–2.35(2H, m, CO—CH$_2$) |
| | 2.50–2.75(2H, m, py-CH$_2$) |
| | 2.75–3.00(2H, m, piperidine) |
| | 3.21(2H, dt, CONHCH$_2$, J=6.3Hz, J=12.2Hz) |
| | 4.21(1H, s, Ar$_2$CH) |
| | 5.35–5.70(1H, m, NH) |
| | 7.00–7.60(12H, m, ar, py) |
| | 8.30–8.50(2H, m, py) |

Example 8

N-{4-[1-(9H-Fluoren-9-yl)-piperidin-4-yl]-butyl)-3-(pyridin-3-yl)-propionamide (Substance 133)

8.0 g (27.7 mmol) N-(4-piperidin-4-yl-butyl)-3-(pyridin-3-yl)-propionamide and 5.6 g (55.3 mmol) TEA are placed in 100 ml acetonitrile and cooled to ca. 0° C. under moisture exclusion. 6.8 g (27.7 mmol) 9-bromofluorene are added in solid form and the mixture is stirred two days at ca. 65° C. and two days at RT. Subsequently, the solvent is drawn off under vacuum to a large extent, and the residue is dispersed between CHCl$_3$ and 10% NaOH. The organic phase is washed twice with water and dried over sodium sulfate. After the removal of the solvent, the residue is chromatographically purified over silica gel with CHCl$_3$/CH$_3$OH (98/2 to 94/6) and crystallized from 30 ml acetonitrile after drawing off the solvent. Colorless crystals with an MP of 131–132° C.; yield 2.5 g (20%).

$C_{30}H_{35}N_3O$ (453.6)

| IR-spectrum (KBr): | ν(NH) 3300 cm$^{-1}$ |
| --- | --- |
| | ν(C=O) 1630, 1530 cm$^{-1}$ |
| $^1$H-NMR-spectrum (CDCl$_3$): | 0.95–1.80(11H, m, piperidine, piperidine-(CH$_2$)$_3$) |
| | 2.25–2.80(6H, m, piperidine, CO—CH$_2$) |
| | 2.97(2H, t, py-CH$_2$, J=7.5Hz) |
| | 3.19(2H, dt, CONHCH$_2$, J=6.5Hz, J=12.5Hz) |
| | 4.82(1H, s, ArCH) |
| | 5.25–5.55(1H, m, NH) |
| | 7.10–7.80(10H, m, ar, py) |
| | 8.35–8.55(2H, m, py) |

Example 9
N-{4-[1-(2-naphthylsulfonyl)-piperidin-4-yl]-butyl}-3-(pyridin-3-yl)-propionamide (Substance 212)

3.5 g (12 mmol) N-(4-piperidin-4-yl-butyl)-3-(pyridin-3-yl)-propionamide and 6.7 ml (48.1 mmol) TEA are placed in 100 ml absolute dichloromethane and cooled to ca. 0° C. under moisture exclusion. 3.0 g (13.2 mmol) naphthalin-2-sulfonic acid chloride are dissolved in 40 ml absolute dichloromethane and added dropwise. The mixture is stirred without further cooling at RT overnight. Subsequently, the batch is washed twice, each with 80 ml water. The organic phase is dried over sodium sulfate and the solvent is removed under vacuum. The residue is chromatographically purified over silica gel with CHCl$_3$/CH$_3$OH (97/3) and crystallized from acetic acid ethyl ester after drawing off the solvent. Colorless crystals with an MP of 103–105° C.; yield 2.87 g (50%).

$C_{27}H_{33}N_3O_3S$ (479.6)

| IR-spectrum (KBr): | ν(NH) 3320 cm$^{-1}$ |
| --- | --- |
| | ν(C=O) 1645, 1530 cm$^{-1}$ |
| $^1$H-NMR-spectrum (CDCl$_3$): | 0.90–1.90(11H, m, piperidine, piperidine-(CH$_2$)$_3$) |
| | 2.05–2.40(2H, m, piperidine) |
| | 2.42(2H, t, CO—CH$_2$, J=7.4Hz) |
| | 2.80–3.30(4H, t, dt, py-CH$_2$, J=7.4Hz, CONHCH$_2$) |
| | 3.70–4.00(2H, m, piperidine) |
| | 5.40–5.70(1H, m, NH) |
| | 7.10–8.15(8H, m, ar, py) |
| | 8.25–8.55(3H, m, ar, py) |

Example 10
N-[4-(1-benzoylpiperidin-4-yl)-butyl]-3-(pyridin-3-yl)-propionamide (Substance 162)

3.48 ml (30 mmol) benzoyl chloride, 8.7 g (30 mmol) N-(4-piperidin-4-yl-butyl)-3-(pyridin-3-yl)-propionamide and 16.6 g (120 mmol) potassium carbonate are stirred in 160 ml DMF at RT overnight. Subsequently, this is filtered and the filtrate is concentrated under vacuum to a large extent. The residue is taken up in 400 ml CHCl$_3$ and washed twice, each with 100 ml water. The organic phase is dried over sodium sulfate and the solvent is removed under vacuum. The residue is chromatographically purified over silica gel with CHCl$_3$/CH$_3$OH (95/5) and precipitates as an amorphous solid after drawing off the solvent.

$C_{24}H_{31}N_3O_2$ (393.5)

| IR-spectrum (KBr): | ν(NH) 3250 cm$^{-1}$ |
| --- | --- |
| | ν(C=O) 1630, 1550 cm$^{-1}$ |
| $^1$H-NMR-spectrum (CDCl$_3$): | 0.85–1.95(11H, m, piperidine, piperidine-(CH$_2$)$_3$) |
| | 2.44(2H, t, CO—CH$_2$, J=7.4Hz) |
| | 2.50–3.35(6H, m, piperidine, py-CH$_2$, CONHCH$_2$) |
| | 3.50–4.00(1H, m, piperidine) |
| | 4.40–4.90(1H, m, piperidine) |
| | 5.70–6.05(1H, m, NH) |
| | 7.10–7.65(7H, m, ar, py) |
| | 8.35–8.55(2H, m, py) |

Example 11
N-{4-1[-(1-naphthylaminocarbonyl)-piperidin-4-yl]-butyl}-3-(pyridin-3-yl)-propionamide (Substance 194)

2.6 ml (17.7 mmol) 1-naphthyl isocyanate are dissolved in 15 ml absolute THF and cooled to ca. 0° C. under moisture exclusion. 5.1 g (17.7 mmol) N-(4-piperidin-4-yl-butyl)-3-(pyridin-3-yl)-propionamide are dissolved in 35 ml absolute THF and added dropwise under ice cooling. The mixture is stirred at RT overnight without further cooling. Subsequently, the solvent is drawn off under vacuum to a large extent and the residue is chromatographically pre-purified over silica gel with CHCl$_3$/CH$_3$OH (90/10) and further purified by flash-chromatography with CHCl$_3$/CH$_3$OH (95/5 to 90/10). After drawing off the solvent, this is crystallized from isopropanol/diisopropyl ether. Colorless crystals with an MP of 143–144° C.; yield 0.77 g (9%).

$C_{28}H_{34}N_4O_2$ (458.6)

| IR-spectrum (KBr): | ν(NH) 3240 cm$^{-1}$ |
| --- | --- |
| | ν(C=O) 1630, 1560 cm$^{-1}$ |
| $^1$H-NMR-spectrum (CDCl$_3$): | 0.95–1.95(11H, m, piperidine, piperidine-(CH$_2$)$_3$) |
| | 2.40(2H, t, CO—CH$_2$, J=7.4Hz) |
| | 2.75–3.40(6H, m, piperidine, py-CH$_2$, CONHCH$_2$) |
| | 4.00–4.30(2H, m, piperidine) |
| | 5.55–5.85(1H, m, NH) |
| | 6.77(1H, s, NH) |
| | 7.10–8.00(9H, m, ar, py) |
| | 8.35–8.55(2H, m, py) |

Example 12
N-{4-[1-(cyclohexylphenylmethyl)-piperidin-4-yl]-butyl}-3-(pyridin-3-yl)-propionamide (Substance 46)

3.8 g (15.0 mmol) (bromocyclohexylphenyl)-methane, 4.3 g (15.0 mmol) N-(4-piperidin-4-yl-butyl)-3-(pyridin-3-yl)-propionamide, 3.1 g (22.5 mmol) potassium carbonate and 0.22 g (1.5 mmol) sodium iodide are stirred in 40 ml DMF for two hours at ca. 105° C. After cooling, the mixture is poured into 100 ml water and extracted with 150 ml acetic acid ethyl ester. The organic phase is dried over sodium sulfate and the solvent is removed under vacuum. The residue is chromatographically purified twice over silica gel with CHCl$_3$/CH$_3$OH (90/10 and 95/5) and crystallized from 10 ml acetonitrile after drawing off the solvent. Beige colored crystals with an MP of 109–110° C., yield 1.4 g (20%).

$C_{30}H_{43}N_3O$ (461.7)

| IR-spectrum (KBr): | ν(NH) 3290 cm$^{-1}$ |
| --- | --- |
| | ν(C=O) 1635, 1545 cm$^{-1}$ |
| $^1$H-NMR-spectrum (CDCl$_3$): | 0.50–2.20(24H, m, piperidine, piperidine-(CH$_2$)$_3$, cyclohexane) |
| | 2.43(2H, t, CO—CH$_2$, J=7.4Hz) |
| | 2.50–3.40(7H, m, piperidine, py-CH$_2$, CONHCH$_2$, ar-CH) |
| | 5.40–5.80(1H, m, NH) |
| | 6.90–7.70(7H, m, ar, py) |
| | 8.30–8.60(2H, m, py) |

Example 13

N[-2-(1-Diphenylmethyl-piperidin-4-ylamino)-ethyl]-3-(pyridin-3-yl)-propionamide Trihydrochloride Semiisopropanolate (Substance 52 as a Hydrochloride)

Production occurs analogously to example 1.

Batch size: 1.8 g (11.7 mmol) 3-(3-pyridyl)-propionic acid, 1.6 ml (11.7 mmol) TEA, 2.4 g (14.4 mmol) 81% HOBT, 2.7 g (14.1 mmol) EDC and 4.0 g (12.9 mmol) N-1-(1-diphenylmethyl-piperidin-4-yl)-ethan-1,2-diamine in 100 ml absolute dichloromethane.

In the purification, this is first chromatographically pre-purified with CHCl$_3$/CH$_3$OH/NH$_4$OH (90/9/1) and flash-chromatography is subsequently carried out with CHCl$_3$/CH$_3$OH (90/10). After removing the solvent, the residue is dissolved in 50 ml isopropanol and added to 4.1 ml ca. 4 M isopropanolic hydrochloric acid. The salt precipitated in the cold is drawn off and dried. Yield of yellow foam 1.1 g (17%).

$C_{28}H_{34}N_4O.3$ HCl.½ isopropanol (582.0)

| IR-spectrum (KBr): | ν(NH) 3400 cm$^{-1}$ |
| --- | --- |
| | ν(C=O) 1650, 1540 cm$^{-1}$ |
| $^1$H-NMR-spectrum (D$_2$O): | 1.70–2.35(4H, m, piperidine) |
| | 2.54(2H, t, CO—CH$_2$, J=7.2Hz) |
| | 2.80–3.60(11H, m, piperidine, py-CH$_2$, NH—CH$_2$, CONHCH$_2$) |
| | 5.23(1H, s, Ar$_2$CH) |
| | 7.20–7.60(10H, m, ar) |
| | 7.70–7.90(1H, m, py) |
| | 8.20–8.55(3H, m, py) |

Example 14

N-[3-(1-benzylpiperidin-4-yloxy)-propyl]-3-(pyridin-3-yl)-propionamide (Substance 36)

Production occurs analogously to example 3.

Batch size: 2.2 g (14.6 mmol) 3-(3-pyridyl)-propionic acid, 3.8 ml (43.9 mmol) oxalyl chloride and 4.0 g (16.1 mmol) 3-(1-benzylpiperidin-4-yloxy)-propylamine in 50 ml absolute dichloromethane.

In the purification, this is chromatographically purified twice over silica gel with CHCl$_3$/CH$_3$OH/NH$_4$OH (90/10/0 to 90/10/1) and CHCl$_3$/CH$_3$OH (95/5 to 90/10) and crystallized from 10 ml 1-chlorobutane after drawing off the solvent. Orange-yellow colored crystals with an MP of 55–57° C., yield 1.8 g (32%).

$C_{23}H_{31}N_3O_2$ (381.5)

| IR-spectrum (KBr): | ν(NH) 3305 cm$^{-1}$ |
| --- | --- |
| | ν(C=O) 1630, 1530 cm$^{-1}$ |
| $^1$H-NMR-spectrum (CDCl$_3$): | 1.35–2.35(8H, m, piperidine, C—(CH$_2$)—C) |
| | 2.43(2H, t, CO—CH$_2$, J=7.4Hz) |
| | 2.60–2.90(2H, m, piperidine) |
| | 2.97(2H, t, py-CH$_2$, J=7.4Hz) |
| | 3.10–3.60(7H, m, piperidine, CONHCH$_2$, O—CH$_2$, ar-CH$_2$) |
| | 6.10–6.55(1H, m, NH) |
| | 7.10–7.40(6H, m, ar, py) |
| | 7.40–7.65(1H, m, py) |
| | 8.35–8.55(2H, m, py) |

Example 15

N-(4-{1-bis-(2-Chlorophenyl)-methyl]-piperidin-4-yl)-butyl}-3-(pyridin-3-yl)-propionamide (Substance 118)

Production occurs analogously to example 12.

Batch size: 4.0 g (1 2.7 mmol) bis-(2-chlorophenyl)-bromomethane, 3.7 g (12.7 mmol) N-(4-piperidin-4-yl-butyl)-3-(pyridin-3-yl)-propionamide, 2.6 g (19.0 mmol) potassium carbonate and 0.2 g (1.3 mmol) sodium iodide in 40 ml DMF.

The reaction temperature and time are 85° C. and 11 hours.

In the purification, this is chromatographically purified twice over silica gel with CHCl$_3$/CH$_3$OH (95/5 to 90/10 and 95/5) and crystallized three times from 10 ml acetonitrile, from 10 ml 1-chlorobutane and subsequently from 6 ml isopropanol/diisopropyl ether (5/1) after drawing off the solvent. Colorless crystals with an MP of 125° C.; yield 1.6 g (24%).

$C_{30}H_{35}C_{12}N_3O$ (524.5)

| IR-spectrum (KBr): | ν(NH) 3240 cm$^{-1}$ |
| --- | --- |
| | ν(C=O) 1625, 1545 cm$^{-1}$ |
| $^1$H-NMR-spectrum (CDCl$_3$): | 0.90–1.85(11H, m, piperidine, piperidine-(CH$_2$)$_3$) |
| | 1.90–2.30(2H, m, piperidine) |
| | 2.44(2H, t, CO—CH$_2$, J=7.5Hz) |
| | 255–2.85(2H, m, piperidine) |
| | 2.97(2H, t, py-CH$_2$, J=7.5Hz) |
| | 3.19(2H, dt, CONHCH$_2$, J=6.5Hz, J=12.4Hz) |
| | 5.31(1H, s, Ar$_2$CH) |
| | 5.35–5.60(1H, m, NH) |
| | 6.95–7.70(10H, m, ar, py) |
| | 8.30–8.55(2H, m, py) |

Example 16

N-[4-(1-Diphenylmethyl-piperidin-4-yl)-butyl]-N-ethyl-3-(pyridin-3-yl)-propionamide (Substance 68)

0.79 g (26.3 mmol) 80% sodium hydride are suspended in 30 ml DMF and 10.0 g (22.0 mmol) N-[4-(1-diphenylmethyl-piperidin-4-yl)-butyl]-3-(pyridin-3-yl)-propionamide (substance 54) are added. The mixture is warmed to ca. 30° C. and, after addition of 0.2 g tetrabutyl ammonium iodide, this is stirred for one hour. Subsequently, 2.0 ml (24.1 mmol) ethyl iodide is added at RT (foam development) and the orange-brown suspension is stirred at RT overnight. Excess sodium hydride is destroyed by addition of 1 ml water and the mixture is concentrated under vacuum to a large extent. The residue is dispersed between 50 ml water and 100 ml dichloromethane. The organic phase is dried over sodium sulfate and the solvent is removed under vacuum. The residue is chromatographically purified three times over silica gel with CHCl₃/CH₃OH (97/3 and 100/0 to 97/3 and 98/2) and crystallized from 10 ml 1-chlorobutane/petroleum ether (3/7) after drawing off the solvent. Beige colored crystals with an MP of 72–74° C.; yield 3.6 g (34%).

$C_{32}H_{41}N_3O$ (483.7)

| IR-spectrum (KBr): | ν(C=O) 1630 cm⁻¹ |
|---|---|
| ¹H-NMR-spectrum (CDCl₃): | 0.90–2.00(16H, m, piperidine, piperidine-(CH₂)₃, CH₃) |
| | 2.40–3.50(10H, m, CO—CH₂, N—CH₂, py-CH₂, piperidine) |
| | 4.21(1H, s, Ar₂CH) |
| | 6.95–7.70(12H, m, ar, py) |
| | 8.35–8.60(2H, m, py) |

Example 17

N-{4-[1-(Biphenyl-4-carbonyl)-piperidin-4-yl]-butyl}-3-(pyridin-3-yl)-propionamide (Substance 168)

Production occurs analogously to example 10.

Batch size: 5.0 g (23.1 mmol) biphenyl-4-carboxylic acid chloride, 6.7 g (23.1 mmol) N-(4-piperidin-4-yl-butyl)-3-(pyridin-3-yl)-propionamide and 12.8 g (92.3 mmol) potassium carbonate in 120 ml DMF.

In the work up, this is dispersed between 300 ml CHCl₃ and 75 ml water. In the purification, this is first chromatographed over silica gel with CHCl₃/CH₃OH (95/5) and subsequently crystallized from 1-chlorobutane. Colorless crystals with an MP of 104–105° C.; yield 6.1 g (56%).

$C_{30}H_{35}N_3O_2$ (469.6)

| IR-spectrum (KBr): | ν(NH) 3310 cm⁻¹ |
|---|---|
| | ν(C=O) 1625, 1530 cm⁻¹ |
| ¹H-NMR-spectrum (CDCl₃): | 0.95–2.10(11H, m, piperidine, piperidine-(CH₂)₃) |
| | 2.56(2H, t, CO—CH₂, J=7.4Hz) |
| | 2.65–3.50(6H, m, piperidine, py-CH₂, CONHCH₂) |
| | 3.65–4.20(1H, m, piperidine) |
| | 4.50–5.00(1H, m, piperidine) |
| | 5.70–6.05(1H, m, NH) |
| | 7.10–7.90(11H, m, ar, py) |
| | 8.40–8.70(2H, m, py) |

Example 18

N-{4-[1-(2-Naphthoyl)-piperidin-4-yl]-butyl}-3-(pyridin-3-yl)-propionamide (Substance 175)

6.0 g (20.7 mmol) N-(4-piperidin-4-yl-butyl)-3-(pyridin-3-yl)-propionamide and 2.1 g (20.7 mmol) TEA are dissolved in 30 ml absolute dichloromethane and cooled to ca. 0° C. under moisture exclusion. 3.95 g (20.7 mmol) 2-naphthoyl chloride are dissolved in 40 ml absolute dichloromethane and added dropwise under ice cooling. The mixture is stirred for two hours at RT without further cooling. Subsequently, the batch is made alkaline with 10% sodium hydroxide solution and washed twice with a small amount of water. The organic phase is dried over sodium sulfate and the solvent is removed under vacuum. The resinous residue is chromatographically purified over silica gel with CHCl₃/CH₃OH (96/4). Yield of colorless resin 5.4 g (59%).

$C_{28}H_{33}N_3O_2$ (443.6)

| IR-spectrum(KBr): | ν(NH) 3280 cm⁻¹ |
|---|---|
| | ν(C=O) 1620, 1545 cm⁻¹ |
| ¹H-NMR-spectrum(CDCl₃): | 1.00–2.05(11H, m, piperidine, piperidine-(CH₂)₃) |
| | 2.55(2H, t, CO—CH₂, J=7.5Hz) |
| | 2.70–3.45(6H, m, piperidine, py-CH₂, CONHCH₂) |
| | 3.65–4.15(1H, m, piperidine) |
| | 4.50–5.05(1H, m, piperidine) |
| | 5.60–5.85(1H, m, NH) |
| | 7.20–7.35(1H, m, py) |
| | 750–7.75(4H, m, ar, py) |
| | 7.85–8.10(4H, m, ar) |
| | 8.40–8.65(2H, m, py) |

Example 19

N-(4-Piperidin-4-yl-butyl)-3-(pyridin-3-yl)-propionamide (Substance 12)

100 g (219.5 mmol) N-[4-(1-diphenylmethyl-piperidin-4-yl)-butyl]-3-(pyridin-3-yl)-propionamide (substance 54) are dissolved in 500 ml ethanol and added to 8.0 g palladium (5%) on activated carbon (moistened with 40 ml water) and 25 ml conc. hydrochloric acid. The mixture is heated to ca. 45° C. and stirred ca. five hours long under hydrogen atmosphere until the consumption of the theoretical amount of hydrogen to be taken up. After cooling, this is filtered from the catalyst and the solvent is removed under vacuum. The residue is taken up in 200 ml water and washed three times with a total of 200 ml CHCl₃. The organic phases are discarded and the aqueous phase is made alkaline with 11 g sodium hydroxide and extracted three times, each with 100 ml CHCl₃. After washing the organic phase with 30 ml water, the solvent is removed under vacuum. The oily residue is filtered over silica gel with CHCl₃/CH₃OH/NH₄OH (80/20/2). Yield of a slowly hardening resin: 53.0 g (83%).

$C_{17}H_{27}N_3O$ (289.4)

| IR-spectrum(KBr): | ν(NH) 3300 cm⁻¹ |
|---|---|
| | ν(C=O) 1630, 1540 cm⁻¹ |
| ¹H-NMR-spectrum(CDCl₃): | 0.90–1.80(11H, m, piperidine, piperidine-(CH₂)₃) |
| | 2.35–2.75(4H, m, CO—CH₂, piperidine) |
| | 2.80–3.35(6H, m, piperidine, py-CH₂, CONHCH₂) |
| | 6.05–6.40(1H, m, NH) |
| | 7.10–7.35(1H, m, py) |
| | 7.40–7.60(1H, m, py) |
| | 8.30–8.55(2H, m, py) |

Example 20

N-(4-Piperidin-4-yl-butyl)-3-(pyridin-3-yl)-pentanoic Acid Amide (Substance 13)

Production occurs analogously to example 19.

Batch size: 37.0 g (76.5 mmol) 5-(pyridin-3-yl)-pentanoic acid-[4-(1-diphenylmethyl-piperidin-4-yl)-butyl]-amide (substance 90)), 2.6 g palladium (5%) on activated carbon (moistened with 15 ml water) and 17 ml conc. hydrochloric acid in 200 ml ethanol. Reactions time ca. 8 hours.

In the work up, the aqueous phase is alkalized with 9.5 g sodium hydroxide solution and extracted three times with CHCl₃ (100 ml. 20 ml and 20 ml). After washing the organic phase twice, each with 20 ml water, the solvent is removed under vacuum and the oily residue is dried under high-vacuum. Yield of a gradually hardening orange colored resin. 24.0 g (98%).

$C_{19}H_{31}N_3O$ (317.4)

| IR-spectrum(KBr): | $\nu$(NH) 3290 cm$^{-1}$ |
| --- | --- |
| | $\nu$(C=O) 1630, 1540 cm$^{-1}$ |
| $^1$H-NMR-spectrum(CDCl$_3$): | 0.70–1.90(16H, m, piperidine, NH piperidine-(CH$_2$)$_3$, C—(CH$_2$)$_2$—C) |
| | 2.00–2.35(2H, m, CO—CH$_2$) |
| | 2.35–2.75(4H, m, piperidine, py-CH$_2$) |
| | 2.90–3.40(4H, m, piperidine, CONHC$\underline{H}_2$) |
| | 5.40–5.75(1H, m, NH) |
| | 7.10–7.30(1H, m, py) |
| | 7.40–7.60(1H, m, py) |
| | 8.30–8.55(2H, m, py) |

A series of synthesis examples are additionally listed in the following table 2 for further illustration of the invention.

TABLE 2

Prepared compounds of formula (I)

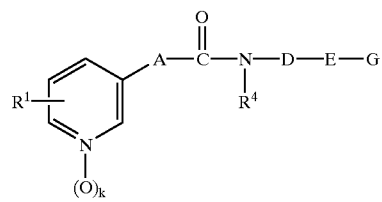

| Nr | R$^1$ | A | D-E-G | MP [° C.] (solvent)$^1$ |
| --- | --- | --- | --- | --- |
| 12 | H | CH$_2$CH$_2$ | CH$_2$CH$_2$CH$_2$CH$_2$-piperidine-N—H | 60–62 (CHCl$_3$/MeOH) |
| 13 | H | CH$_2$CH$_2$CH$_2$CH$_2$ | CH$_2$CH$_2$CH$_2$CH$_2$-piperidine-N—H | 57–59 (CHCl$_3$) |
| 28 | H | CH$_2$CH$_2$ | CH$_2$CH$_2$CH$_2$CH$_2$-piperidine-N—CH$_2$-phenyl | 61–63 (iPr$_2$O) |
| 36 | H | CH$_2$CH$_2$ | CH$_2$CH$_2$CH$_2$O-piperidine-N—CH$_2$-phenyl | 55–57 (BuCl) |
| 44 | H | CH$_2$CH$_2$ | CH$_2$CH$_2$CH$_2$CH$_2$-piperidine-N—CH$_2$-biphenyl | 125 (EE) |
| 45 | H | CH$_2$CH$_2$ | CH$_2$CH$_2$CH$_2$CH$_2$-piperidine-N—CH$_2$-anthracenyl | 133–135 (EtOH) |

TABLE 2-continued

Prepared compounds of formula (I)

| Nr | R¹ | A | D-E-G | MP [° C.] (solvent)[1] |
|---|---|---|---|---|
| 46 | H | CH₂CH₂ | CH₂CH₂CH₂CH₂—[piperidine]—N—CH(C₆H₅)(cyclohexyl) | 109–110 (MeCN) |
| 51 | H | CH₂CH₂ | CH₂CH₂CH₂—[piperidine]—N—CH(C₆H₅)₂ | 109–110 (BuCl) |
| 52 | H | CH₂CH₂ | CH₂CH₂NH—[piperidine]—N—CH(C₆H₅)₂ | 162–171[2] (iPrOH) |
| 54 | H | CH₂CH₂ | CH₂CH₂CH₂CH₂—[piperidine]—N—CH(C₆H₅)₂ | 139 (EE) |
| 55 | | [pyridine N-oxide]—CH₂CH₂—C(O)—NH—CH₂CH₂CH₂CH₂—[piperidine]—N—CH(C₆H₅)₂ | | Harz[3] |
| 65 | 2-OH | CH₂CH₂ | CH₂CH₂CH₂CH₂—[piperidine]—N—CH(C₆H₅)₂ | 135–136 (MeCN) |
| 66 | 6-CH₃O | CH₂CH₂ | CH₂CH₂CH₂CH₂—[piperidine]—N—CH(C₆H₅)₂ | 135–137 (BuCl) |
| 67 | 6-C₆H₅O | CH₂CH₂ | CH₂CH₂CH₂CH₂—[piperidine]—N—CH(C₆H₅)₂ | 116–118 (BuCl) |
| 68 | | [pyridine]—CH₂CH₂—C(O)—N(CH₂CH₃)—CH₂CH₂CH₂CH₂—[piperidine]—N—CH(C₆H₅)₂ | | 72–74 (BuCl/PE) |
| 72 | H | CHCH₂ \| CH₃ | CH₂CH₂CH₂CH₂—[piperidine]—N—CH(C₆H₅)₂ | Harz[3] |

TABLE 2-continued

Prepared compounds of formula (I)

[Structure: R¹-substituted pyridine (with (O)ₖ on N) — A — C(=O) — N(R⁴) — D — E — G]

| Nr | R¹ | A | D-E-G | MP [° C.] (solvent)[1] |
|---|---|---|---|---|
| 73 | H | CH₂CH(C₂H₅) | CH₂CH₂CH₂CH₂—[piperidine]—CH(C₆H₅)₂ | 137–138 (EE) |
| 74 | H | CH₂CH(C₆H₅) | CH₂CH₂CH₂CH₂—[piperidine]—CH(C₆H₅)₂ | 58–60 (BuCl) |
| 84 | H | OCH₂ | CH₂CH₂CH₂CH₂—[piperidine]—CH(C₆H₅)₂ | 103–105 (EE) |
| 90 | H | CH₂CH₂CH₂CH₂ | CH₂CH₂CH₂CH₂—[piperidine]—CH(C₆H₅)₂ | 109 (EE) |
| 91 | H | CH₂NHCH₂CH₂ | CH₂CH₂CH₂CH₂—[piperidine]—CH(C₆H₅)₂ | 138–140[4] (iPrOH) |
| 93 | H | CH₂N(CHO)CH₂CH₂ | CH₂CH₂CH₂CH₂—[piperidine]—CH(C₆H₅)₂ | Harz[3] |
| 101 | H | CH₂CH₂ | CH₂CH₂CH₂CH₂CH₂—[piperidine]—CH(C₆H₅)₂ | 112–114 (MeCN) |
| 105 | H | CH₂CH₂ | CH₂CH₂CH₂CH₂NH—C(=O)—[piperidine]—CH(C₆H₅)₂ | 159–161 (MeCN) |
| 105 | H | CH₂CH₂ | (CH₂)₆NH—C(=O)—[piperidine]—CH(C₆H₅)₂ | 76–78 (MeCN) |

115
TABLE 2-continued
Prepared compounds of formula (I)
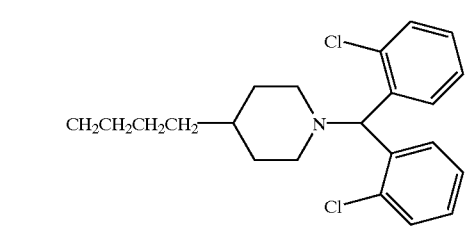
| Nr | R¹ | A | D-E-G | MP [° C.] (solvent)[1] |
|---|---|---|---|---|
| 118 | H | CH₂CH₂ | 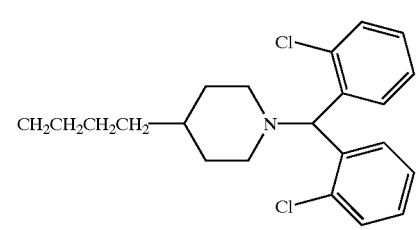 | 125 (iPrOH) |
| 120 | H | CH₂CH₂CH₂CH₂ | 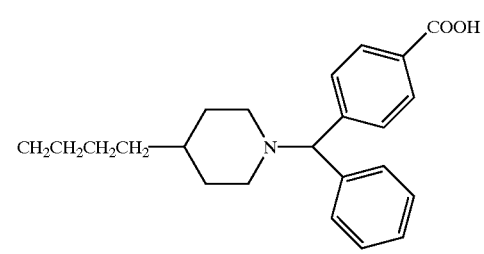 | viskoses Ol[3] |
| 125 | H | CH₂CH₂ | 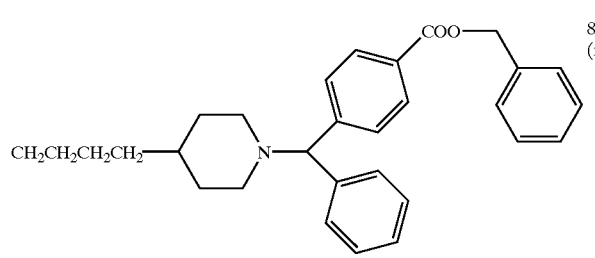 | 82–87 (amorph; CHCl₃/MeOH) |
| 126 | H | CH₂CH₂ | 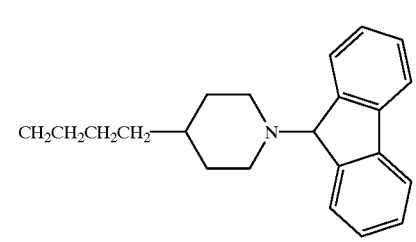 | 84–85 (iPr₂O/MTBE) |
| 133 | H | CH₂CH₂ |  | 131–132 (MeCN) |

TABLE 2-continued
Prepared compounds of formula (I)
| Nr | R¹ | A | D-E-G | MP [° C.] (solvent)[1] |
|---|---|---|---|---|
| 135 | H | CH$_2$CH$_2$ | 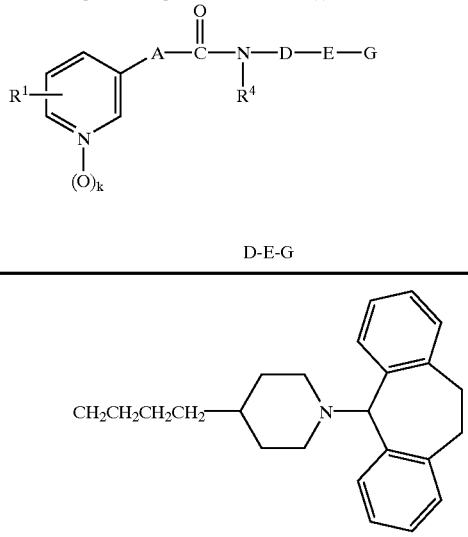 | 113–115 (EE) |
| 142 | H | CH$_2$CH$_2$ | 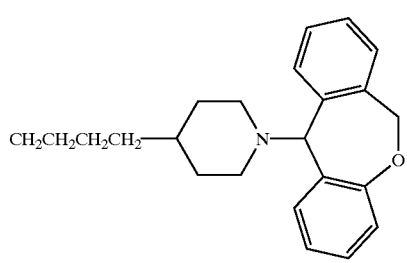 | 110–112 (EE) |
| 157 | H | CH$_2$CH$_2$CH$_2$CH$_2$ | 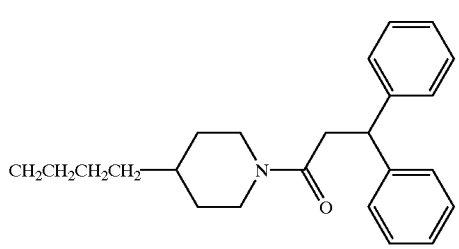 | Harz[3] |
| 158 | H | CH$_2$CH$_2$ | 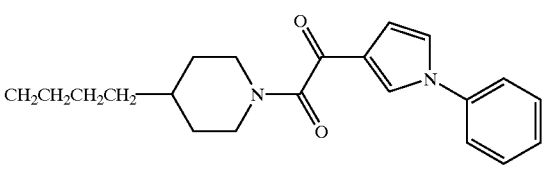 | 119–121 (EtOH) |
| 162 | H | CH$_2$CH$_2$ | 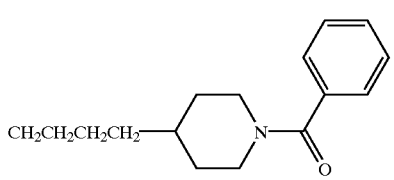 | 72–74 (CHCl$_3$/MeOH) |
| 166 | H | CH$_2$CH$_2$ | 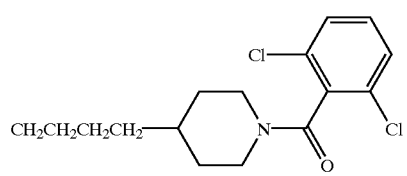 | Harz[3] |

TABLE 2-continued

Prepared compounds of formula (I)

| Nr | R¹ | A | D-E-G | MP [° C.] (solvent)[1] |
|---|---|---|---|---|
| 168 | H | $CH_2CH_2$ | $CH_2CH_2CH_2CH_2$-piperidine-N-C(O)-C₆H₄-C₆H₅ | 104–105 (BuCl) |
| 170 | H | $CH_2CH_2$ | $CH_2CH_2CH_2CH_2$-piperidine-N-C(O)-(2-phenyl)phenyl | Harz[3] |
| 172 | H | $CH_2CH_2$ | $CH_2CH_2CH_2CH_2$-piperidine-N-C(O)-1-naphthyl | Harz[3] |
| 175 | H | $CH_2CH_2$ | $CH_2CH_2CH_2CH_2$-piperidine-N-C(O)-2-naphthyl | Harz[3] |
| 183 | H | $CH_2CH_2$ | $CH_2CH_2CH_2CH_2$-piperidine-N-C(O)-2-furyl | 98–99 (BuCl) |
| 184 | H | $CH_2CH_2$ | $CH_2CH_2CH_2CH_2$-piperidine-N-C(O)-3-pyridyl | 85–87 (EtOH) |
| 194 | H | $CH_2CH_2$ | $CH_2CH_2CH_2CH_2$-piperidine-N-C(O)-NH-1-naphthyl | 143–144 (iPrOH) |

TABLE 2-continued

Prepared compounds of formula (I)

| Nr | R¹ | A | D-E-G | MP [° C.] (solvent)¹ |
|---|---|---|---|---|
| 201 | H | $CH_2CH_2$ | $CH_2CH_2CH_2CH_2$-piperidine-N-C(=O)-N(10,11-dihydrodibenz[b,f]azepine) | Harz³ |
| 202 | H | $CH_2CH_2CH_2CH_2$ | $CH_2CH_2CH_2CH_2$-piperidine-N-C(=O)-N(10,11-dihydrodibenz[b,f]azepine) | Harz³ |
| 211 | H | $CH_2CH_2$ | $CH_2CH_2CH_2CH_2$-piperidine-N-$SO_2$-(naphthalen-1-yl) | Harz³ |
| 212 | H | $CH_2CH_2$ | $CH_2CH_2CH_2CH_2$-piperidine-N-$SO_2$-(naphthalen-2-yl) | 103–105 (EE) |
| 214 | H | $CH_2CH_2CH_2CH_2$ | $CH_2CH_2CH_2CH_2$-piperidine-N-$SO_2$-(naphthalen-2-yl) | 97–98 (EE) |
| 221 | H | $CH_2CH_2$ | $CH_2CH_2CH_2CH_2$-piperidine-N-$SO_2$-(5-chloro-3-methylbenzo[b]thiophen-2-yl) | 159–160 (MeCN) |
| 223 | H | $CH_2CH_2$ | $CH_2CH_2CH_2CH_2$-piperidine-N-P(=O)(phenyl)$_2$ | 134–135 (iPr₂O) |

Table annotation
[1]MeOH = methanol
iPr₂O = diisopropylether
BuCl = 1-chlorobutane TABLE 2-continued Prepared compounds of formula (I)

| Nr | R¹ | A | D-E-G | MP [° C.] (solvent)[1] |
|---|---|---|---|---|

EE = ethyl acetate
EtOH = ethanol
MeCN = acetonitrile
iPrOH = isopropanol
PE = petroleum ether
MTBE = methyl tert-butyl ether
[2]as a trihydrochloride
[3]purified by column chromatography Several examples for the synthesis of the starting materials are given in the following for a better understanding of the production methods for the end products

SYNTHESIS OF STARTING PRODUCTS

Example 1A
4-(1-Diphenylmethyl-piperidin-4-yl)-butylamine 88.9 g (196 mmol) 2-[4-(1-diphenylmethyl-piperidin-4-yl)-butyl]-isoindol-1,3-dione are suspended in 1000 ml ethanol and added to 22.0 g (440 mmol) hydrazine hydrate and heated to boiling for four hours. After cooling, the mixture is filtered and the solvent is removed under vacuum. The solid residue is dispersed in the heat together with the filter residue between 300 ml 10% sodium hydroxide solution and 300 ml acetic acid ethyl ester. The aqueous phase is extracted once with 150 ml warm acetic acid ethyl ester. The combined organic phases are extracted twice, each with 300 ml 10% hydrochloric acid. The combined aqueous phases are made basic with 10% sodium hydroxide solution and extracted twice, each with 400 ml acetic acid ethyl ester. The combined organic phases are washed with 100 ml water and dried over sodium sulfate. The solvent is removed under vacuum, the residue is dried under high-vacuum and processed further without additional purification. Yield of a gradually hardening resin: 63 g (99%).

Example 2A
2-[4-(1-Diphenylmethyl-piperidin-4-yl)-butyl]-isoindol-1,3-dione 135.0 g (417. mmol) 4-(1-diphenylmethyl-piperidin-4-yl)-butan-1-ol, 109.5 g (417 mmol) triphenylphosphine and 61.3 g (417 mmol) phthalimide are suspended in THF. Thereafter, 2.6 g (417 mmol) azodicarboxylic acid diethyl ester are added dropwise within two and a half hours under protective atmosphere and light cooling (ca. 15–25° C.). After an additional hour, the solvent is removed under vacuum and the residue is crystallized three times from acetic acid ethyl ester (1000 ml, 1200 ml and 1100 ml). Colorless crystals with an MP of 150–152° C.; yield 103 g (54.5 %).

Example 3A
4-(1-Diphenylmethyl-piperidin-4-yl)-butan-1-ol 120 g (620 mmol) 4-piperidin-4-yl-butan-1-ol hydrochloride are suspended in 400 ml 3,4-dihydro-2H-pyran and added to 1.5 g pyridinium tosylate and 5 ml 8 M methaneolic hydrochloric acid. This is stirred for three hours and left to stand at RT overnight. After addition of 5 g potassium carbonate, this is concentrated under vacuum to dryness. The resulting 4-[4-Tetrahydro-pyran-2-yloxy)-butyl]-piperidine is. dissolved in 500 ml acetonitrile without further purification and added to 193 g (742 mmol) diphenylmethyl bromide (95%) and 160 g (1157 mmol) potassium carbonate and stirred for three days at RT. The mixture is filtered and the filtrate is stirred with a further 20 g (76.8 mmol) diphenylmethyl bromide (95%) and 16 g (115.8 mmol) potassium carbonate for one day at RT. The mixture is filtered and the solvent is removed under vacuum. The resulting 1-diphenylmethyl-4-[4-(tetrahydro-pyran-2-yloxy)-butyl]-piperidine is dissolved in 700 ml methanol without further purification, added to 120 ml conc. hydrochloric acid and the mixture is left to stand for two days at RT. Subsequently, the solvent is drawn off under vacuum, the residue is taken up with 1500 ml water and extracted with 1500 ml acetic acid ethyl ester. The organic phase is discarded and the aqueous phase is made alkaline with 95 g sodium hydroxide and extracted with 700 ml acetic acid ethyl ester. After washing the organic phase with 200 ml water, this is dried over sodium sulfate and the solvent is removed under vacuum. The brown oil is dried under high-vacuum and further processed without additional purification. Yield 145 g (72%).

Example 4A
3-(1-Benzylpiperidin-4-yloxy)-propylamine 10 g (40.9 mmol) 3-(1-benzylpiperidin-4-yloxy)-propionitrile are dissolved in 100 ml ethanol and added to a spatula tip Raney-Nickel. The mixture is stirred at RT and under hydrogen atmosphere until the consumption of the theoretical amount of hydrogen to be taken up (ca. two days). Subsequently, this is filtered from the catalyst and the solvent is removed under vacuum. The residue is distilled in a bulb tube apparatus. Yield of a colorless oil: 7.5 g (73%).

Example 5A
N-1-(1-Diphenylmethyl-piperidin-4-yl)-ethan-1,2-diamine 10 g (37.7 mmol) N-diphenylmethyl-4-piperidone and 22.2 g (349 mmol) ethylenediamine are dissolved in methanol and added to 1.7 g (45.2 mmol).sodium borohydride. The mixture is stirred for two hours at RT. Subsequently, the solvent is removed under vacuum. The residue is dispersed between CHCl$_3$ and water and the aqueous phase is extracted twice, each with 100 ml CHCl$_3$. The combined organic phases are dried over sodium sulfate and the solvent is removed under vacuum. The residue is chromatographically purified over silica gel with CHCl$_3$/CH$_3$OH/NH$_4$OH (90/10/0 to 90/10/1). Yield: 11.2 g (96%).

Example 6A 5-(1-Diphenylmethyl-piperidin-4-yl)-pentylamine 19.0 g (57.1 mmol) 5-(1-diphenylmethyl-piperidin-4-yl)-pentanitrile are dissolved in 240 ml dioxane/ethanol (1/1) and added to 3.2 g Raney-Nickel. The mixture is stirred at RT under hydrogen atmosphere until the uptake of the theoretical amount of hydrogen. The mixture is filtered from the catalyst and the solvent is removed under vacuum. The residue is dispersed between 100 ml water and 250 ml acetic acid ethyl ester. The organic phase is dried with sodium sulfate and the solvent is removed under vacuum. The resin is further processed without additional purification. Yield: 17.0 g (88%).

Example 7A 5-(1-Diphenylmethyl-piperidin-4-yl)-pentannitrile 24.9 (69.2 mmol) 4-(1-diphenylmethyl-piperidin-4-yl)-butan-1-ol hydrochloride are suspended in 160 ml absolute dichloromethane and cooled to ca. 0° C. under moisture exclusion. At this temperature, 16.0 g (159 mmol) TEA are first added and thereafter a solution of 0.3 g (90.0 mmol) methanesulfonoic acid chloride in a little absolute dichloromethane is added dropwise. The mixture is then subsequently stirred for three hours at RT and then placed in ice water. The organic phase is washed once with 50 ml water, dried over sodium sulfate and the solvent is removed under vacuum. The resulting methanesulfonoic acid-4-(1-diphenylmethyl-piperidin-4-yl)-butyl ester is dissolved in 120 ml DMF without further purification and with 7.7 g (158 mmol) sodium cyanide and two drops 15-crown-5 and stirred for six hours at 65° C. After cooling, the mixture is poured in ice water. The precipitated solid is drawn off and dried at 40° C. in high-vacuum. The solid is processed further without additional purification. Yield: 19.9 g (86%).

Example 8A

1-Diphenylmethyl-piperidin-3-carboxylic Acid-(4-aminobutyl)-amide

Analogously to example 3, 5.6 g (16.8 mmol) 1-diphenylmethyl-piperidin-3-carboxylic acid hydrochloride is reacted with 3.8 g (30.1 mmol) oxalyl chloride to the acid chloride. This is suspended in absolute dichloromethane and added to 2.28 g (15.3 mmol) N-(tert-butoxycarbonyl)-butanediamine and 1.55 g (15.3 mmol) TEA and stirred at RT overnight. The mixture is subsequently concentrated, taken up in CHCl$_3$ and washed once with 50 ml 10% sodium hydroxide solution and twice, each with 50 ml water. The organic phase is dried over sodium sulfate and the solvent is removed under vacuum. The residue is chromatographically purified over silica gel CHCl$_3$/CH$_3$OH (98/2 to 96/4) and dissolved in 70 ml ethanol. After addition of 5 ml conc. hydrochloric acid, the mixture is heated to boiling for 5 hours. After cooling, the solvent is removed under vacuum and azeotropically dehydrated twice with toluene and subsequently dried under high-vacuum. The resin is further processed without additional purification. Yield: 5.9 g (81%).

Example 9A

1-Diphenylmethyl-piperidin-3-carboxylic Acid Hydrochloride 15.7 g (100 mmol) piperidin-3-carboxylic acid ethyl ester and 30.4 g (220 mmol) potassium carbonate are placed in 100 ml DMF and 24.1 g diphenylmethyl bromide is added dropwise. The mixture is stirred at RT overnight and subsequently filtered. The filtrate is concentrated under vacuum and the residue is taken up with 150 ml acetic acid ethyl ester, then extracted twice, each with 50 ml 10% hydrochloric acid. The organic phase is discarded and the combined aqueous phases are made basic with 10% sodium hydroxide solution and extracted twice, each with 50 ml acetic acid ethyl ester. The combined organic phases are cooled to ca. 0° C. and the precipitated solid is drawn off and dried. Yield 20.5 g (63%) of the compound 1-diphenylmethyl-piperidin-3-carboxylic acid ethyl ester with a MP of 166–168° C. This compound is heated to boiling together with 24 ml 20% hydrochloric acid in 100 ml water for 8 hours. After cooling, the precipitate is filtered and crystallized from 70 ml methanol. Yield. 15.6 g (74%).

The active ingredients according to the invention can be processed to the desired medicaments in the form of their acid addition salts, hydrates or solvates individually or in combination with each other, optionally under addition of other active ingredients, for the indications tumor treatment or immunosuppression. In the case of the combination of active ingredients according to the invention with other medicinal forms, these can also optionally be separately present next to each other in the medicine packaging, for example as tablets next to viles, depending on the requirements.

Further subject-matter of the invention is a method for the treatment of the human or animal body in which a compound or compound mixture according to formula (I), wherein the substituents have the above described meaning, is administered for treatment of tumors and/or as a cytostatic agent, cancerostatic agent, immunosuppressing agent, optionally in combination with further cytostatic or immunosuppressive active ingredients or other active ingredients suitable in the named indications.

Furthermore, the invention relates to a compound or compound mixture according to formula (I) for use in a therepeutic method in which the therapeutic use is carried out in connection with one or more medical indications with tumors or for immunosuppression, optimally in combination with further pharmaceuticals suitable in the named indications.

The use of one or more compounds according to formula (I) for the production of medicaments for the treatment of the human or animal body, especially in connection with one or more medical indications in the treatment of tumors or for immunosuppression, optimally in combination with further pharmaceuticals suitable in these indications or the use of compounds according to formula (I) in a corresponding diagnosis method represent an embodiment according to the invention.

The respective suitable tumor indications are illustrated in the last section of the description in the discussion of the pharmacological test results.

A method for the production of medicaments with an amount of one or more compounds according to formula (I) which are suitable for the processing of these active ingredients together with respective suitable pharmaceutically acceptable carriers and adjuvants for finished medicinal forms equally belongs to the scope of protection according to the invention.

Depending on the medical indication being considered, the respective suitable medical form is selected for the suitable therapeutic application.

The invention also relates to the use of the compounds according to formula (I) for treatment in the above indications.

The production of the respective suitable medicaments as well as a series of examples of medicinal forms are described in the following for better understanding of the invention.

Therapeutic Administration Forms

The production of medicaments with an amount of one or more compounds according to the invention and/or their use in the application according to the invention occurs in the customary manner by means of common pharmaceutical technology methods. For this, the active ingredients as such or in the form of their salts are processed together with suitable, pharmaceutically acceptable adjuvents and carriers to medicinal forms suitable for the various indications and types of application. Thereby, the medicaments can be produced in such a manner that the respective desired release rate is obtained, for example a quick flooding and/or a sustained or depot effect.

Preparations for parenteral use, to which injections and infusions belong, are amono the most important systemically employed medicaments for tumor treatment as well as for other indications.

Preferably, injections are administered, for the treatment of tumors. These are prepared either in the form of vials or also as so-called ready-to-use injection preparations, for example as ready-to-use syringes or single use syringes in addition to perforation bottles for multiple withdrawals. Administration of the injection preparations can occur in the form of subcutaneous (s.c.), intramuscular (i.m.), intravenous (i.v.) or intracutaneous (i.c.) application. The respective suitable injection forms can especially be produced as solutions, crystal suspensions, nanoparticular or colloid-disperse systems, such as for example, hydrosols.

The injectable formulations can also be produced as concentrates which can be adjusted with aqueous isotonic dilution agents to the desired active ingredient dosage. Furthermore, they can also be produced as powders, such as for example lyophilisates, which are then preferably dissolved or dispersed immediately before application with suitable diluents. The infusions can also be formulated in the form of isotonic solutions, fat emulsions, liposome formulations, microemulsions and liquids based on mixed micells, for example, based on phospholipids. As with injection preparations, infusion formulations can also be prepared in the form of concentrates to dilute. The injectable formulations can also be applied in the form of continuous infusions as in stationary as well as in out-patient therapy, for example in the form of mini-pumps.

Albumin, plasma expanders, surface active compounds, organic solvents, pH influencing compounds, complex forming compounds or polymeric compounds can be added to the parenteral medicinal forms, especially as substances for influencing the adsorption of the active ingredients to protein or polymers or also with the aim of decreasing the adsorption of the active ingredient to materials such as injection instruments or packaging materials, for example plastic or glass.

The active ingredients can be bound to nanoparticles in the preparations for parenteral use, for example on finely dispersed particles based on poly(meth)acrylates, polyacetates, polyglycolates, polyamino acids or polyether urethanes. The parenteral formulations can also be constructively modified as depot preparations, for example on the multiple unit principle, where the active ingredients are incorporated in a most finely distributed and/or dispersed, suspended form or as crystal suspensions, or on the single unit principle, where the active ingredient is enclosed in a medicinal form for example, a tablet or a seed which is subsequently implanted. Often, these implantations or depot medicaments in single unit and multiple unit medicinal forms consist of so-called biodegradable polymers, such as for example, polyether urethanes of lactic and glycolic acid, polyether urethanes, polyarnino acids, poly(meth)acrylates or polysaccharides.

Sterilized water, pH value influencing substances, such as for example organic and inorganic acids or bases as well as their salts, buffer substances for setting the pH value, agents for isotonicity, such as for example sodium chloride, monosodium carbonate, glucose and fructose, tensides and/or surface active substances and emulsifiers, such as for example, partial fatty acid esters of polyoxyethylene sorbitan (Tween®) or for example fatty acid esters of polyoxethylene (Cremophor®), fatty oils such as for example peanut oil, soybean oil and castor oil, synthetic fatty acid esters, such as for example ethyl oleate, isopropyl myristate and neutral oil (Miglyol®) as well as polymer adjuvents such as for example gelatin, dextran, polyvinylpyrrolidone, organic solvent additives which increase solubility, such as for example propylene glycol, ethanol, N,N-dimethylacetamide, propylene glycol or complex forming compounds such as for example citrates and urea, preservatives, such as for example hydroxypropyl benzoate and hydroxymethyl benzoate, benzyl alcohol, anti-oxidants, such as for example sodium sulfite and stabilizers, such as for example EDTA, are suitable as adjuvents and carriers in the production of preparations for parenteral use.

In suspensions, addition of thickening agents to prevent the settling of the active ingredients from tensides and peptizers, to secure the ability of the sediment to be shaken, or complex formers, such as EDTA, ensues. This can also be achieved with the various polymeric agent complexes, for example with polyethylene glycols, polystyrol, carboxymethylcellulose, Pluronics® or polyethylene glycol sorbitan fatty acid esters. The active ingredient can also be incorporated in liquid formulations in the form of inclusion compounds, for example with cyclodextrins. As further adjuvents, dispersion agents are also suitable. For production of lyophilisates, builders are also used, such as for example mannite, dextran, saccharose, human albumin, lactose, PVP or gelatin varieties.

As long as the active ingredients are not incorporated in the liquid medicinal formulations in the form of a base, they are used in the form of their acid addition salts, hydrates or solvates in the preparations for parenteral use.

A further systemic application form of importance is peroral administration as tablets, hard or soft gelatin capsules, coated tablets, powders, pellets, microcapsules, oblong compressives, granules, chewable tablets, lozenges, gums or sachets. These solid peroral administration forms can also be prepared as sustained action and/or depot systems. Among these are medicaments with an amount of one or more micronized active ingredients, diffusions and erosion forms based on matrices, for example by using fats, wax-like and/or polymeric compounds, or so-called reservoir systems. As a retarding agent and/or agent for controlled release, film or matrix forming substances, such as for example ethylcellulose, hydroxypropylmethylcellulose, poly(meth)acrylate derivatives (for example Eudragit®), hydroxypropylmethylcellulose phthalate are suitable in organic solutions as well as in the form of aqueous dispersions. In this connection, so-called bio-adhesive preparations are also to be named in which the increased retention time in the body is achieved by intensive contact with the mucus membranes of the body. An example of a bio-adhesive polymer is the group of Carbomers®.

For sublingual application, compressives, such as for example non-disintegrating tablets in oblong form of a suitable size with a slow release of active ingredient, are especially suitable. For purposes of a targeted release of active ingredients in the various sections of the gastrointestinal tract, mixtures of pellets which release at the various places are employable, for example mixtures of gastric fluid soluble and small intestine soluble and/or gastric fluid resistant and large intestine soluble pellets. The same goal of releasing at various sections of the gastrointestinal tract can also be conceived by suitably produced laminated tablets with a core, whereby the coating of the agent is quickly released in gastric fluid and the core of the agent is slowly released in the small intestine milieu. The goal of controlled release at various sections of the gastrointestinal tract can also be attained by multilayer tablets. The pellet mixtures with differentially released agent can be filled into hard gelatin capsules.

Anti-stick and lubricant and separating agents, dispersion agents such as flame dispersed silicone dioxide, disintegrants, such as various starch types, PVC, cellulose esters as granulating or retarding agents, such as for example wax-like and/or polymeric compounds on the basis of Eudragit®, cellulose or Cremophor® are used as a further adjuvents for the production of compressives, such as for example tablets or hard and soft gelatin capsules as well as coated tablets and granulates.

Anti-oxidants, sweetening agents, such as for example saccharose, xylite or mannite, masking flavors, aromatics, preservatives, colorants, buffer substances, direct tableting agents, such as for example microcrystalline cellulose, starch and starch hydrolysates (for example Celutab®), lactose, polyethylene glycols, polyvinylpyrrolidone and dicalcium phosphate, lubricants, fillers, such as lactose or starch, binding agents in the form of lactose, starch varieties, such as for example wheat or corn and/or rice starch, cellulose derivatives, for example methylcellulose, hydroxypropylcellulose or silica, talcum powder, stearates, such as for example magnesium stearate, aluminum stearate, calcium stearate, talc, siliconized talc, stearic acid, acetyl alcohol and hydrated fats are used.

In this connection, oral therapeutic systems constructed especially on osmotic principles, such as for example GIT (gastrointestinal therapeutic system) or OROS (oral osmotic system), are also to be mentioned.

Effervescent tablets or tabs, both of which represent immediately drinkable instant medicinal forms which are quickly dissolved or suspended in water are among the perorally administratable compressives. Among the perorally administratable forms are also solutions, for example drops, juices and suspensions, which can be produced according to the above given method, and can still contain preservatives for increasing stability and optionally aromatics for reasons of easier intake, and colorants for better differentiation as well as antioxidants and/or vitamins and sweeteners such as sugar or artificial sweetening agents. This is also true for inspisated juices which are formulated with water before ingestion. Ion exchange resins in combination with one or more active ingredients are also to be mentioned for the production of liquid ingestable forms.

A special release form consists in the preparation of so-called floating medicinal forms, for example based on tablets or pellets which develop gas after contact with body fluids and therefore float on the surface of the gastric fluid. Furthermore, so-called electronically controlled release systems can also be formulated by which active ingredient release can be selectively adjusted to individual needs.

A further group of systemic administration and also optionally topically effective medicinal forms are represented by rectally applicable medicaments. Among these are suppositories and enema formulations. The enema formulations can be prepared based on tablets with aqueous solvents for producing this administration form. Rectal capsules can also be made available based on gelatin or other carriers.

Hardened fat, such as for example Witepsol®, Massa Estarinum®, Novata®, coconut fat, glycerol-gelatin masses, glycerol-soap-gels and polyethylene glycols are suitable as suppository bases.

For long-term application with a systematic active ingredient release up to several weeks, pressed implants are suitable which are preferably formulated on the basis of so-called biodegradable polymers.

As a further important group of systemically active medicaments, transdermal systems are also to be emphasized which distinguish themselves, as with the above-mentioned rectal forms, by circumventing the liver circulation system and/or liver metabolism. These plasters can be especially prepared as transdermal systems which are capable of releasing the active ingredient in a controlled manner over longer or shorter time periods based on different layers and/or mixtures of suitable adjuvents and carriers. Aside from suitable adjuvents and carriers such as solvents and polymeric components, for example based on Eudragit®, membrane infiltration increasing substances and/ or permeation promoters, such as for example oleic acid, Azone(®, adipinic acid derivatives, ethanol, urea, propylglycol are suitable in the production of transdermal systems of this type for the purpose of improved and/or accelerated penetration.

As topically, locally or regionally administration medicaments, the following are suitable as special formulations: vaginally or genitally applicable emulsions, creams, foam tablets, depot implants, ovular or transurethral administration installation solutions. For opthalmological application, highly sterile eye ointments, solutions and/or drops or creams and emulsions are suitable.

In the same manner, corresponding otological drops, ointments or creams can be designated for application to the ear. For both of the above-mentioned applications, the adminstration of semi-solid formulations, such as for example gels based on Carbopols® or other polymer compounds such as for example polyvinylpyrolidone and cellulose derivatives is also possible.

For customary application to the skin or also to the mucus membrane, normal emulsions, gels, ointments, creams or mixed phase and/or amphiphilic emulsion systems (oil/ water-water/oil mixed phase) as well as liposomes and transfersomes can be named. Sodium algenate as a gel builder for production of a suitable foundation or celluolose derivatives, such as for example guar or xanthene gum, inorganic gel builders, such as for example aluminum hydroxides or bentonites (so-called thixotropic gel builder), polyacrylic acid derivatives, such as for example Carbopol®R, polyvinylpyrolidone, microcrystalline cellulose or carboxymethylcellulose are suitable as adjuvents and/or carriers. Furthermore, amphiphilic low and high molecular weight compounds as well as phospholipids are suitable. The gels can be present either as hydrogels based on water or as hydrophobic organogels, for example based on mixtures of low and high molecular paraffin hydrocarbons and vaseline.

Anionic, cationic or neutral tensides can be employed as emulsifiers, for example alkalized soaps, methyl soaps, amine soaps, sulfanated compounds, cationic soaps, high fatty alcohols, partial fatty acid esters of sorbitan and polyoxyethylene sorbitan, for example lanette types, wool wax, lanolin, or other synthetic products for the production of oil/water and/or water/oil emulsions.

Hydrophilic organogels can be formulated, for example, on the basis of high molecular polyethylene glycols. These gel-like forms are washable. Vaseline, natural or synthetic waxes, fatty acids, fatty alcohols, fatty acid esters, for example as mono-, di-, or triglycerides, paraffin oil or vegetable oils, hardened castor oil or coconut oil, pig fat, synthetic fats, for example based on acrylic, caprinic, lauric and stearic acid, such as for example Softisan® or triglyceride mixtures such as Miglyol® are employed as lipids in the form of fat and/or oil and/or wax-like components for the production of ointments, creams or emulsions.

Osmotically effective acids and bases, such as for example hydrochloric acid, citric acid, sodium hydroxide solution, potassium hydroxide solution, monosodium carbonate, further buffer systems, such as for example citrate, phosphate, Tris-buffer or triethanolamine are used for adjusting the pH value.

Preservatives, for example such as methyl- or propyl benzoate (parabenes) or sorbic acid can be added for increasing stability.

Pastes, powders or solutions are to be mentioned as further topically applicable forms. Pastes often contain lipophilic and hydrophilic auxiliary agents with very high amounts of fatty matter as a consistency-giving base.

Powders or topically applicable powders can contain for example starch varieties such as wheat or rice starch, flame dispersed silicon dioxide or silica, which also serve as diluents, for increasing flowability as well as lubricity as well as for preventing aglomerates.

Nose drops or nose sprays serve as nasal application forms. In this connection, nebulizers or nose creams or ointments can come to use.

Furthermore, nose spray or dry powder formulations as well as controlled dosage aerosols are also suitable for systemic administeration of the active ingredients.

These pressure and/or controlled dosage aerosols and dry powder formulations can be inhaled and/or insufflated. Administration forms of this type also certainly have importance for direct, regional application in the lung or bronchi and larynx. Thereby, the dry powder compositions can be formulated for example as active ingredient-soft pellets, as an active ingredient-pellet mixture with suitable carriers, such as for example lactose and/or glucose. For inhalation or insufflation, common applicators are suitable which are suitable for the treatment of the nose, mouth and/or pharynx. The active ingredients can also be applied by means of an ultrasonic nebulizing device. As a propellant gas for aerosol spray formulations and/or controlled dosage aerosols, tetrafluoroethane or HFC 134a and /or heptafluoropropane or HFC 227 are suitable, wherein non-fluorinated hydrocarbons or other propellants which are gaseous at normal pressure and room temperature, such as for example propane, butane or dimethyl ether can be preferred. Instead of controlled dosage aerosols, propellant-free, manual pump systems can also be used.

The propellant gas aerosols can also suitably contain surface active adjuvents, such as for example isopropyl myristate, polyoxyethylene sorbitan fatty acid ester, sorbitan trioleate, lecithins or soya lecithin.

For regional application in situ, solutions for installation, for example for transurethral administration in bladder tumors or genital tumors, or for profusion in liver tumors or other organ carcinomas are suitable.

The respective suitable medicinal forms can be produced in accordance with the prescription and procedures based on pharmaceutical-physical fundamentals as they are described for example in the following handbooks and are included in the present inventive subject-matter with respect to the production of the respective suitable medicaments.

Physical Pharmacy (A. N. Martin, J. Swarbrick, A. Cammarata), 2nd Ed., Philadelphia Pa., (1970), German version: Physikalische Pharmazie, (1987), 3rd edition, Stuttgart;

R. Voigt, M. Bornschein, Lehrbuch der pharmazeutischen Technologie, Verlag Chemie, Weinheim, (1984), 5th edition;

P. H. List, Arzneimformenlehre, Wissenschaftliche Verlagsgesellschaft mbH, Stuttgart, (1985), 4th edition;

H. Sucker, P. Fuchs, P. Speiser, Pharmazeutische Technologie, Georg Thieme Verlag, Stuttgart—New York, (1991), 2nd edition;

A. T. Florence, D. Attwood, Physicochemical Principles of Pharmacy, The Maximillan Press Ltd., Hong Kong, (1981);

L. A. Trissel, Handbook on Injectable Drugs, American Society of Hospital Pharmacists, (1994), 8th edition;

Y. W. Chien, Transdermal Controlled Systemic Medications, Marcel Dekker Inc., New York—Basel, (1987);

K. E. Avis, L. Lachmann, H. A. Liebermann, Pharmaceutical Dosage Forms: Parenteral Medications, volume 2, Marcel Dekker Inc., New York—Basel, (1986);

B. W. Müller, Controlled Drug Delivery, Paperback APV, volume 17, Wissenschaftliche Verlagsgesellschaft mbH, Stuttgart, (1987);

H. Asch, D. Essig, P. C. Schmidt, Technologie von Salben, Suspensionen und Emulsionen, Wissenschaftliche Verlagsgesellschaft mbH, Stuttgart, (1984);

H. A. Liebermann, L. Lachman, J. B. Schwartz, Pharmaceutical Dosage forms: Tablets, Volume 1, Marcel Dekker Inc., New York, 2nd Edition (1989);

D. Chulin, M. Deleuil, Y. Pourcelot, Powder Technology and Pharmaceutical Processes, in J. C. Williams, T. Allen, Handbook of Powder Technology, Elsevier Amsterdam—London—New York—Tokyo, (1994);

J. T. Carstensen, Pharmaceutical Principles of Solid Dosage Forms, Technomic Publishing Co., Inc., Lancaster—Basel, (1993).

PRODUCTION EXAMPLES

1. Injection Therapeutics
   a) Parenteral Solution

| | |
|---|---|
| active ingredient used according to the invention | 5.000 g |
| acid sodium phosphate | 5.000 g |
| sodium tartrate | 12.000 g |

| | |
|---|---|
| benzyl alcohol | 7.500 g |
| water for injection purposes | to 1000.000 ml |

The solution is produced according to the customary method, sterilized and filled into 10 ml vials. One vial contains 50 mg of the compound according to the invention.

b) Penteral Solution

| | |
|---|---|
| active ingredient used according to the invention | 1.000 g |
| hydrochloric acid, dilute | 5.000 g |
| sodium chloride | 6.000 g |
| water for injection purposes | to 1000.000 ml |

The solution is produced according to a customary method by stirring, the medicinal form is adjusted to a suitable pH value by acid addition and subsequently filled into 100 ml vials and sterilized. A vial contains 100 mg of the compound according to the invention.

c) Parenteral Dispersion

| | |
|---|---|
| active ingredient used according to the invention | 10.000 g |
| soya lecithin | 20.000 g |
| saturated triglycerides | 100.000 g |
| sodium hydroxide | 7.650 g |
| water for injection purposes | to 1000.000 ml |

The active ingredient(s) used according to the invention is dispersed in the saturated triglycerides. Then the soya lecithin is added under stirring, and subsequent to this, the aqueous solution of sodium hydroxide is added with subsequent homogenization. The dispersion is sterilized and filled into 10 ml vials. A vial contains 50 mg of the compound according to the invention.

d) Biodegradable Parenteral Depot Medicinal Form

| | |
|---|---|
| active ingredient used according to the invention | 10.000 |
| polylactic acid/polygylcolic acid polymer | 70.000 |
| polyvinylpyrrolidone | 0.200 |
| gelatin | 2.000 |
| soya lecithin | 2.000 |
| isotonic sodium chloride solution | to 1000.000 ml |

First, the active ingredient is incorporated into the biodegradable polymer comprising polylactic acid and polyglycolic acid by a suitable method (spray drying, solvent-evaporation or phase separation) and subsequently subjected to a sterilization process. The particles are introduced into a 2-chamber ready-made syringe in which the adjuvent solution, which is also produced in a sterile manner, is filled. The biodegradable microparticles are mixed with the dispersion agent shortly before application and dispersed. A ready-made syringe contains 200 mg of the active compound according to the invention.

e) Parenteral Dispersion for Subcutaneous Installation

| | |
|---|---|
| active ingredient used according to the invention | 25,000 g |
| soya lecithin | 25,000 g |
| arachis oil | 400,000 g |
| benzyl alcohol | 50,000 g |
| Miglyole ® | to 1000,000 g |

The active ingredient is dispersed together with soya lecithin and arachis oil. The benzyl alcohol is dissolved in Miglyole® and added to the dispersion. The entire dispersion is sterilized and subsequently filled into vials with 2 ml content. A vial contains 50 mg active ingredient.

f) Parenteral Perfusions Solution

The solution named under example b) can also be used for perfusion of liver for example.

According to need, instead of ampules with injection solution, so-called perforation bottles (vials), which can also be optionally preserved, and infusion solutions with an amount of one or more active ingredients according to the invention can also be made available in the customary manner under addition of buffer substances for adjustment of physiological pH value and/or the isotonicity and/or a best possible suitable pH value for the medicinal form (euhydria) and optional further required nutrients, vitamins, amino acids, stablizers and other necessary adjuvents, possibly in combination with further medicinal agents suitable for the mentioned indications.

2. Solid, Peroral Administration Medicaments a) Tablets

| | |
|---|---|
| active ingredient used according to the invention | 10,000 g |
| lactose | 5,200 g |
| starch, soluble | 1,800 g |
| hydroxypropylmethylcellulose | 900 g |
| magnesium stearate | 100 g |

The above components are mixed with each other and compacted in a conventional manner, wherein a tablet weight of 180 mg is set. Each tablet contains 100 mg active ingredient. If desired, the tablets obtained in this manner are coated, provided with a film coat and/or enterically coated.

b) Coated Tablet Core

| | |
|---|---|
| active ingredient used according to the invention | 10,000 g |
| flame dispersed silicon dioxide | 500 g |
| corn starch | 2,250 g |
| stearic acid | 350 g |
| ethanol | 3.0 l |
| gelatin | 900 g |
| purified water | 10.0 l |
| talcum | 300 g |
| magnesium stearate | 180 g |

From these components, a granulate is produced which is pressed to the desired coated tablet cores. Each core contains 50 mg of active ingredient. The core can be further processed in a customary manner to coated tablets. If desired, a gastric fluid resistant or retarding film coat can be applied in a known manner.

c) Drink Suspension in Vials

| | |
|---|---|
| active ingredient used according to the invention | 0.050 g |
| glycerin | 0.500 g |
| sorbite, 70% solution | 0.500 g |

-continued

| | |
|---|---|
| sodium saccharinate | 0.010 g |
| methyl-p-hydroxybenzoate | 0.040 g |
| aromatic agent | q.s. |
| sterile wasser | q.s to 5 ml |

The above-mentioned components are mixed in a customary manner to a suspension and filled in a suitable drink vial having 5 ml content.

d) Poorly Soluble Sublingual Tablets

| | |
|---|---|
| active ingredient used according to the invention | 0.030 g |
| lactose | 0.100 g |
| stearic acid | 0.004 g |
| talcum purum | 0.015 g |
| sweetener | q.s |
| aromatic agent | q.s. |
| rice starch | q.s to 0.500 g |

The active ingredient is compacted together with the adjuvents under high pressure to sublingual tablets, favorably in oblong form.

e) Soft Gel Capsule

| | |
|---|---|
| active ingredient used according to the invention | 0.050 g |
| fatty acid glyceride mixture (Miglyole ®) | q.s. to 0.500 g |

The active ingredient is impasted together with the fluid carrier mixture and mixed together with further adjuvents suitable for the incapsulation and filled into elastic soft gelatin capsules which are sealed.

f) Hard Gelatin Capsules

| | |
|---|---|
| active ingredient used according to the invention | 0.150 g |
| microcrystalline cellulose | 0.100 g |
| hydroxypropylmethyl cellulose | 0.030 g |
| mannite | 0.100 g |
| ethylcellulose | 0.050 g |
| triethyl citrate | 0.010 g |

The active ingredient is mixed together with the adjuvents, microcrystalline cellulose, hydroxypropylmethylcellulose and mannite, wet with granulation liquid and formed into pellets. These are subsequently coated with a solution of ethylcellulose and triethyl citrate in organic solvents in a fluidized-bed apparatus. A hard gelatin capsule contains 150 mg of active ingredient.

3. Topically Administratable Medicinal Forms a) Hydrophilic Ointment

| | |
|---|---|
| active ingredient used according to the invention | 0.500 g |
| Eucerinum ® anhydricum | 60.000 g |
| microcrystalline wax | 15.000 g |
| vaseline oil | q.s to 100.000 g |

The above-mentioned adjuvants are melted and further processed together with the active ingredient to an ointment in a customary manner.

b) Lipophilic Ointment

| | |
|---|---|
| active ingredient used according to the invention | 10.000 g |
| propylene glycol | 50.000 g |
| paraffin, liquid | 100.000 g |
| paraffin wax | 100.000 g |
| vaseline | to 1000.000 ml |

The active ingredient(s) used according to the invention is dissolved in propylene glycol at ca. 60° C. At the same time, the lipophilic components are melted at 60–70° C. and subsequently combined with the active ingredient solution. The ointment is emulsified at first at 60–70° C. and subsequently cooled to 35–40° C. under constant emulsification and then filled in 10 g tubes. A tube contains 100 mg of the compound according to the invention.

4. Inhalation Therapeutic

Further subject-matter is a pharmaceutical formulation which is characterized in that it contians an active ingredient (s) used according to the invention as a base or a physiologically acceptable salt thereof together with carriers and/or diluents customary for this and suitable for administration by means of inhalation.

In connection with the production of the medicaments, particularly suitable physiologically acceptable salts of the active ingredients are, as already illustrated in the synthesis section, acid addition salts derived from inorganic or organic acids such as for example especially hydrochloride, hydrobromide, sulfate, phosphate, maleate, tartrate, citrate, benzoate, 4-methoxybenzoate, 2- or 4-hydroxybenzoate, 4-chlorobenzoate, p-tosylate, methaneosulfonate, ascorbate, salicylate, acetate, formate, succinate, lactate, glutarate, gluconate or tricarballylate.

The administration of the active ingredient(s) used of the invention by means of inhalation occurs according to the invention in conventional ways customary for administrations of this form, for example in the form of a commercial controlled dosage aerosol or in combination with a spacer. In controlled dosage aerosols, a metering valve is delivered with whose help, a dosed amount of the composition is administered. For spraying, the present compositions can be formulated for example as aqueous solutions or suspensions and be administered by means of an atomizer. Aerosol spray formulations in which the active ingredient is either suspended with one or two stabilizers in a propellant as a carrier and/or diluent, for example tetrafluoroethane or HFC 134a and/or heptafluoropropane or HFC 227 can equally be used, whereby however, non-fluorinated hydrocarbons or other propellants which are gaseous at normal pressure and room temperature, such as propane, butane or dimethyl ether, can be preferred. Thereby, propellant-free manual pump systems or dry powder systems as described below can also be used.

Suitably, the propellant aerosols can also contain surface active adjuvents, such as for. example isopropyl myristate, polyoxyethylene sorbitan fatty acid ester, sorbitan trioleate, lecithins, oleic acid.

For administration by means of inhalation and/or insufflation, the medicaments with an amount of compounds according to the invention can also be formulated in the form of dry powder compositions, for example as active ingredient-soft pellets or as an active ingredient-powder mixture with a suitable carrier, such as for example lactose and/or glucose. The powder compositions can be formulated and administered as single doses or as multiple doses.

The compounds according to the invention are preferably administered by means of a controlled dosage aerosol or in the form of a dry powder dosage formulation, wherein the latter preferably contains glucose and/or lactose as a carrier substance.

As applicators for inhalation of the pharmaceutical formulations containing one or more of the active ingredient(s) used according to the invention, all applicators are generally suitable which are suitable for controlled dosage aerosols and/or a dry powder dosage formulation, such as for example usual applicators for the nose, mouth and or pharynx, or also devices standing under propellant gas for the delivery of a spray (as controlled dosage aerosol or dry powder dosage formulation) as they are also used for inhalations in the nose, mouth and/or pharynx.

A further embodiment can also consist of an aqueous solution of the active ingredient(s) used according to the invention, which also optionally contains further active ingredients and/or additives, which are applied by means of an ultrasound atomizer.

|  | Intended dose per stroke | per aerosol % by weight |
|---|---|---|
| a) Controlled Dosage Aerosol |  |  |
| active ingredient used according to the invention | 0.500 mg | 0.66 |
| stabilizer | 0.075 mg | 0.10 |
| HFC 134a | 75.500 mg | 99.24 |
| b) Controlled Dosage Aerosol |  |  |
| active ingredient used according to the invention | 0.250 mg | 0.32 |
| Stabilizer | 0.038 mg | 0.05 |
| HFC 227 | 79.180 mg | 99.63 |

In the examples a) and b) the micronized active ingredient is, after previous dispersion in a small amount of the stabilizer, placed in a suspension vessel in which the bulk amount of propellant gas solution is found. The corresponding suspension is dispersed by means of a suitable stirring system (for example high performance mixer or ultrasound mixer) until an ultra-fine dispersion results. The suspension is then continuously held in flux in a filling apparatus suitable for cold propellants or pressure fillings. Alternatively, the suspension can also be produced in a suitable cooled stabilizer solution in HFC 134a/227.

The examples c) to d) describe the composition and production of dosage dry powder formulations.

|  | mg/dose |
|---|---|
| c) Dosage-Dry Powder Formulation |  |
| active ingredient used according to the invention | 0.500 mg |
| d) Dosage-Dry Powder Formulation |  |
| active ingredient used according to the invention | 0.500 mg |
| lactose Ph. Eur. | to 2.5 mg or to 5.0 mg |
| e) Dosage-Dry Powder Formulation |  |
| active ingredient used according to the invention | 0.250 mg |
| lactose Ph. Eur. | to 2.5 mg or to 5.0 mg |

Im example c) the active ingredient is formulated after micronization under addition of steam as pellets with an MMAD between 0,1 and 0,3 mm diameter and brought to use in a multi-dose powder applicator.

In the examples d) and e) the active ingredient is micronized, thereafter, bulk material is mixed with the lactose in the given amounts, and subsequently, filled in a multi-dose powder inhilator.

In all of the examples set forth above, the active ingredient or the medicinal agent in the form of the respective suitable pharmaceutical acceptable salt and/or acid addition salts can be present, insofar as the base is not preferred in each case.

In the following, the pharmaceutical test results obtained in connection with the newly found indications based, in a representative manner, on the specifically structured new compounds are described.

PHARMACEUTICAL EXPERIMENTAL SECTION

1. Growth Inhibition of Human Tumor Cells

The tumor growth inhibiting activity of the substances was determined on human tumor cells in standardized in vitro test systems. In the screening tests, the substances gave $IC_{50}$-values in a concentration range of 0.1 nM to 10 $\mu$M.

Example

HepG2 cells plated at a density of 20,000 cells/ml in 12-well plastic dishes. Cultivation occurred in Richters IMEM-ZO nutrient medium with 5% fetal calf serum (FCS) in a tissue culture incubator with a gas mixture of 5% $CO_2$ and 95% air at a temperature of 37° C. One day after plating, the culture medium was aspirated from the cells and replaced by fresh medium which contained the respective concentrations of the test substance. For the individual concentrations and the controls without test substances, three-fold batch were done for each. Three days after the beginning of treatment, the medium was again renewed with the test compounds. After six days of substance incubation, the test was ended and the protein amount in the individual wells was determined with the sulforhodamin-B-method (according to P. Skehan et al.: New Colorimetric Cytotoxicity Assay for Anticancer-Drug Screening. J. Natl. Cancer Inst. 82: 1107–1112, 1990). The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [$\mu$M] |
|---|---|
| 54 | 0.02 |
| 84 | 0.08 |
| 101 | 0.03 |

2. Indications

The compounds of formula (I) and their salts permit a therapeutic use in malignant illness of human and animals through their excellent inhibition of the growth of tumor cells. The anti-neoplastic activity of the described substances can be used for prophylactic, adjunct, palliative, and curative treatment of solid tumors, leukemic illnesses and lymphomas as well as for decreasing or preventing metastasis formation in humans and animals. The therapeutic use is possible in the following illnesses for example: gynecological tumors, such as of the uterus or the vagina, ovarian carcinomas, testicle tumors, prostate carcinomas, skin cancer, kidney cancer, bladder tumors, esophagus carcinomas, stomach cancer, rectal carcinomas, pancreas carcinomas, thyroid cancer, adrenal tumors, leukemia and lymphomas, such as Hodgkin's disease, tumor illnesses of the CNS, soft-tissue sarcomas, bone sarcomas, benign and malignant mesotheliomas, but especially intestine cancer, liver cancer, breast cancer, bronchial and lung carcinomas, melanomas, acute and chronic leukemias. Thereby, benign papillomatosis tumors are also considered for therapy. The broad activity of the new compounds was tested in vitro on various human tumor cells. Thereby, the following $IC_{50}$ values were obtained for compound Nr. 54:

| Cell line | Source | $IC_{50}$ Values [μM] |
|---|---|---|
| HT-29 | colon carcenoma | 0.08 |
| HepG2 | hepatocellular carcinoma | 0.02 |
| MCF-7 | ER-positive mammacarcinoma | 0.08 |
| Saos-2 | osteosarcoma | 0.02 |
| THP-1 | monocytic leukemia | 0.03 |
| Namalwa | Burkitt's lymphoma | 0.05 |

The novel structural class of compounds possesses an independent activity profile in the effectiveness against the various tumor types. Thus, tumors which are resistant to customary cytostatic agents, for example, respond entirely to these substances. In addition, based on the independent characteristics, combinations of the new compounds with known chemo-therapeutically used pharmaceuticals or other methods of treatment are considered, wherein their various properties are complimented in a suitable manner. The integration of the presently used compounds with their specific structures in a therapy scheme is successful with one or more substances from the following classes for example: anti-metabolites (for example cytarabine, 5-fluorouracil, 6-mercaptopurine, methotrexate), alkylating agents (for example busulfan, carmustine, cisplatin, carboplatin, cyclophosphamide, dacarbazine, melphalane, thiotepa), DNA-intercalating substances and topoisomerase inhibitors (for example actinomycin D, daunorubicin, doxorubicin, mitomycin C, mitoxantrone, etoposide, teniposide, topotecan, irinotecan), spindle poisons (for example vincristine, navelbin, taxol, taxoter), hormonally active agents (for example tamoxifen, flutamide, formestan, goserelin) or other cytostatic agents with complex modes of action (for example L-asparaginase, bleomycin, hydroxyurea). Resistant tumor cells can be made sensitive again by interaction of the new compounds with a mechanism of resistance for common cytostatic agents (for example P-glycoprotein, MRP, glutathione-S-transferase, metallothionein). A combination is also suitable with radiation therapy, hyperthermia or immunotherapy.

3. Immuno Suppressing Activity

Many anti-tumor agents have not only a cytotoxic effect on tumor cells, but also on the blood cell system. This leads to a weakening of the immune defence, which can, in turn, be specifically employed to suppress the rejection reaction after an organ transplantation for example. Therefore, a use of the main compounds, optionally in combination with other compounds effective for these indications is suitable in diseases such as psoriasis or autoimmune diseases. In order to test the possibility for a therapeutic use in illnesses of this type, the substance activity was tested on freshly isolated lymphocytes as follows:

The spleen of a Swiss mouse served as a lymphocyte source. The lymphocyte population was isolated from the spleen cell suspension over a ficoll gradient and taken up in IMEM-ZO culture medium with 0,1% dextran 70,000 and 2% fetal calf serum. The cells were plated at a density of ca. 500,000 cells/well/ml in a 12-well plate, 1 ml doubly concentrated test substance solution was pipetted per well and this was subsequently incubated in a tissue culture incubator at 37° C. and 5% $CO_2$. After 2 days, a 1 ml-aliquot with 5 μl of the fluorescent dye solutions propidium iodide (8 mg/ml) and 3,3'-dihexyloxacarbocyanin iodide (40 μg/ml) each was added per well, and incubated for 3 minutes at room temperature. Subsequently, 10,000 cells per each sample were measured on a flow-through cytometer and the percentage amount of vital cells in the population was determined. By means of the dose-response curves, $IC_{50}$-values were calculated which were also employed in the following Tables for the characterization of the individual substances:

| Test Substance No. | $IC_{50}$ [μM] |
|---|---|
| 54 | 0.003 |

Furthermore, the independent class of the compounds used according to the invention also permits a combination with known immunosuppressive agents such as for example cyclosporin A, tacrolimus, rapamycin, azathioprin and glucocorticoids.

The invention is in no way limited to the present respective concretely named active ingredient concentrations, dosages, combinations with one or more other cytostatic agents, tumor inhibitors, cancerostatic agents, immunosuppressive agents or further medicinal agents suitable for the respective specific indications or the type of tumor to treated or immunological illness, etc.

What is claimed is:

1. Compounds of formula (I) and pharmaceutically acceptable salts of formula (I)

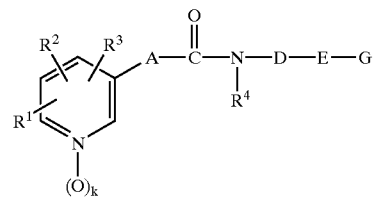

(I)

wherein
$R^1$ is selected from the group consisting of hydrogen, halogen, cyano, $C_1$–$C_6$-alkyl, $C_3$–$C_6$-alkenyl, $C_3$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, $NR^5R^6$, and bridged $R^1R^2$ wherein
    $R^5$ is selected from the group consisting of hydrogen, $C_1$–$C_6$-alkyl, $C_3$–$C_6$-alkenyl and $C_3$–$C_6$-alkinyl,
    $R^6$ is selected from the group consisting of hydrogen, $C_1$–$C_6$-alkyl, $C_3$–$C_6$-alkenyl and $C_3$–$C_6$-alkinyl,
$R^2$ is selected from the group consisting of hydrogen, halogen, cyano, $C_1$–$C_6$-alkyl, trifluoromethyl, hydroxy, $C_1$–$C_6$-alkoxy, benzyloxy, $C_1$–$C_7$-alkanoyloxy, and bridged $R^1R^2$;

wherein bridged $R^1R^2$ is where $R^1R^2$ are adjacent and form a bridge which is selected from the group consisting of —(CH$_2$)$_4$— and —(CH=CH)$_2$— and —CH$_2$O—CR$^7$R$^8$—O—, wherein
$R^7$ is selected from the group consisting of hydrogen and C$_1$–C$_6$-alkyl and
$R^8$ is selected from the group consisting of hydrogen and C$_1$–C$_6$-alkyl,
$R^3$ is selected from the group consisting of hydrogen, halogen, C$_1$–C$_6$-alkyl, trifluoromethyl and C$_1$–C$_6$-hydroxyalkyl;
$R^4$ is selected from the group consisting of hydrogen, C$_1$–C$_6$-alkyl, C$_3$–C$_6$-alkenyl, C$_3$–C$_6$-alkinyl, C$_3$–C$_6$-cycloalkyl, hydroxy, C$_1$–C$_6$-alkoxy and benzyloxy;
k is 0 or 1,
A is selected from the group consisting of C$_1$–C$_6$-alkylene, a substituted C$_1$–C$_6$-alkylene which is substituted once to three-fold by C$_1$–C$_3$-alkyl, hydroxy, C$_1$–C$_3$-alkoxy, fluorine or phenyl,
a 1,2-cyclopropylene and an isosterically substituted C$_2$–C$_6$-alkylene, which has a methylene unit which is isosterically replaced by O, S, NR$^9$, CO, SO or SO$_2$, wherein the isosteric replacement, with the exception of =CO, is not adjacent to the amide group, and wherein
$R^9$ is selected from the group consisting of hydrogen, C$_1$–C$_6$-alkyl, C$_3$–C$_6$-alkenyl, C$_3$–C$_6$-alkinyl, C$_1$–C$_6$-acyl and C$_1$–C$_6$-alkylsulfonyl,
D is selected from C$_1$–C$_{10}$-alkylene, a substituted C$_1$–C$_{10}$-alkylene which is substituted once or twice by C$_1$–C$_6$-alkyl, hydroxy, or C$_1$–C$_6$-alkoxy,
a C$_2$–C$_{10}$-alkenylene, a substituted C$_2$–C$_{10}$-alkenylene which is substituted once or twice by C$_1$–C$_6$-alkyl, hydroxy, C$_1$–C$_6$-alkoxy,
an E double bonded C$_2$–C$_{10}$-alkenylene which has a double bond to ring E,
an E double bonded substituted C$_2$–C$_{10}$-alkenylene which has a double bond to ring E,
a C$_3$–C$_{10}$-alkinylene, a substituted C$_3$–C$_{10}$-alkinylene which is substituted once or twice by C$_1$–C$_6$-alkyl, hydroxy, or C$_1$–C$_6$-alkoxy, and
an isosterically replaced C$_1$–C$_{10}$-alkylene, C$_2$–C$_{10}$-alkenylene or C$_3$–C$_{10}$-alkinylene, having an isosterically replaced group having one to three methylene units which are each isosterically replaced by O, S, NR$^{10}$, CO, SO or SO$_2$, wherein
$R^{10}$ has the same meaning as $R^9$, but is selected independently therefrom,
E is

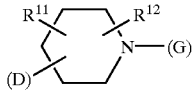

$R^{11}$ is selected from the group consisting of hydrogen, C$_1$–C$_6$-alkyl, hydroxy, hydroxymethyl, carboxy and C$_2$–C$_7$-alkoxycarbonyl, and
$R^{12}$ is selected from the group consisting of hydrogen, C$_1$–C$_6$-alkyl and an oxo group adjacent to the nitrogen atom, or
$R^{11}$ and $R^{12}$ together form a C$_1$–C$_3$-alkylene bridge under formation of a bi-cyclic ring system,
G is selected from the group consisting of hydrogen, G1, G2, G3, G4 and G5, wherein G1 is —(CH$_2$)$_r$—(CR$^{14}$R$^{15}$)$_s$—R$^{13}$ wherein
r is an integer from 1 to 3 or 0,
s is 0 or 1,
$R^{13}$ is selected from the group consisting of hydrogen, C$_1$–C$_6$-alkyl, C$_3$–C$_6$-alkenyl, C$_3$–C$_6$-alkinyl, C$_3$–C$_8$-cycloalkyl, benzyl, phenyl, anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group,
$R^{14}$ has the same meaning as $R^{13}$, but is selected independently thereof,
$R^{15}$ is selected from the group consisting of hydrogen, hydroxy, methyl, benzyl, phenyl, anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group,
G2 is selected from the group consisting of

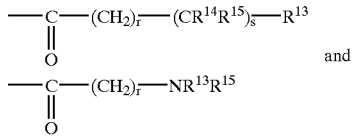

and wherein the substituents $R^{13}$ and $R^{15}$ have the above meaning,
G3 is —SO$_2$—(CH$_2$)$_r$R$^{13}$ and
G4 is

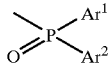

wherein
Ar$^1$ is selected from the group consisting of phenyl, and naphthyl, Ar$^2$ is selected from the group consisting of phenyl, and naphthyl, and
G5 is —COR$^{16}$ wherein
$R^{16}$ is selected from the group consisting of trifluoromethyl, C$_1$–C$_6$-alkoxy, C$_3$–C$_6$-alkenyloxy, and benzyloxy,
and wherein aromatic rings in the substituents $R^1$, $R^2$, $R^4$, $R^{13}$, $R^{14}$, $R^{15}$, $R^{16}$, Ar$^1$ and Ar$^2$ are substituted and unsubstituted, the substituted rings in $R^1$, $R^2$, $R^4$, $R^{13}$, $R^{14}$, $R^{15}$, $R^{16}$, Ar$^1$ and Ar$^2$ having substitutents which are independently selected from halgen, cyano, C$_1$–C$_6$-alkyl, trifluoromethyl, C$_3$–C$_8$-cycloalkyl, phenyl, benzyl, hydroxy, C$_1$–C$_6$-alkoxy, benzyloxy, phenoxy, mercapto, C$_1$–C$_6$-alkylthio, carboxy, C$_1$–C$_6$-alkoxycarbonyl, benzyloxycarbonyl, nitro, amino, mono-C$_1$–C$_6$-alkylamino, di-(C$_1$–C$_6$-alkyl)-amino, and substituted C$_1$–C$_6$ alkoxy which is entirely or partially substituted by fluorine, wherein two adjacent groups on the aromatic ring may form an additional ring over a methylenedioxy bridge.

2. Compounds according to claim 1, wherein
halogen is selected from the group consisting of fluorine, chlorine, bromine and iodine, C₁–C₆-alkyl is selected from the group consisting of methyl, ethyl, propyl, isopropyl, butyl, isobutyl, sec-butyl, tert-butyl, cyclopropylmethyl, pentyl, isopentyl, tert-pentyl, neopentyl, cyclopropylethyl, cyclobutylmethyl and hexyl, C₁–C₁₀-alkylene is selected from the group consisting of methylene, ethylene, propylene, butylene, pentylene, hexylene, heptylene, octylene, nonylene and decylene, C₁–C₆-alkylene is selected from the group consisting of methylene, ethylene, propylene, butylene, pentylene and hexylene, C₂–C₆-alkylene is selected from the group consisting of ethylene, propylene, butylene, pentylene and hexylene, C₁–C₃-alkylene is selected from the group consisting of methylene, ethylene and propylene, C₃–C₆-alkenyl is selected from the group consisting of allyl, 2-butenyl, 3-butenyl, 2-methyl-2-propenyl, 2-pentenyl, 4-pentenyl, 2-methyl-2-butenyl, 3-methyl-2-butenyl, 2-hexenyl, 5-hexenyl, 4-methyl-3-pentenyl and 2,2-dimethyl-3-butenyl, C₂–C₁₀-alkenylene is selected from the group consisting of ethenylene, propenylene, butenylene, pentenylene, hexenylene, hexadienylene, heptenylene, octenylene, nonenylene and decenylene, C₃–C₆-alkinyl is selected from the group consisting of propargyl, 2-butinyl, 3-butinyl, 4-pentinyl, 5-hexinyl and 4-methyl-2-pentinyl, C₃–C₁₀-alkinylene is selected from the group consisting of propinylene, butinylene, pentinylene, hexinylene, heptinylene, octinylene, noninylene and decinylene, C₃–C₈-cycloalkyl is selected from the group consisting of cyclopropyl, cyclobutyl, cyclopentyl, cyclohexyl, cycloheptyl and cyclooctyl, C₁–C₆-hydroxyalkyl is hydroxymethyl or hydroxyethyl C₁–C₆-alkoxy is selected from the group consisting of methoxy, ethoxy, isopropoxy, tert-butoxy, difluoromethoxy, trifluoromethoxy and 2,2,2-trifluoroethoxy, C₃–C₆-alkenyloxy is allyloxy, C₃–C₆-alkinyloxy is propargyloxy, C₁–C₆-alkylthio is selected from the group consisting of methylthio, ethylthio, isopropylthio and tert-butylthio, C₃–C₈-cycloalkyloxy is cyclopentyloxy or cylohexyloxy, C₃–C₈-cycloalkylthio is cyclopentylthio or cyclohexylthio, C₁–C₇-alkanoyloxy is selected from the group consisting of acetoxy, proplonyloxy and pivaloyloxy, C₂–C₇-alkoxycarbonyl is selected from the group consisting of methoxycarbonyl, ethoxycarbonyl, isopropoxycarbonyl, isobutoxycarbonyl and tert-butoxycarbonyl, C₂–C₇-alkoxycarbonyloxy is selected from the group consisting of methoxycarbonyloxy, ethoxycarbonyloxy, isopropoxycarbonyloxy, isobutoxycarbonyloxy, and tert-butoxycarbonyloxy, C₃–C₁₃-dialkylaminocarbonyl is selected from the group consisting of dimethylaminocarbonyl, diethylaminocarbonyl and diisopropylaminocarbonyl NR⁵R⁶ is selected from the group consisting of amino, C₁–C₆-alkylamino and di-(C₁–C₆-alkyl)amino, whereas C₁–C₆-alkylamino is selected from the group consisting of methylamino, ethylamino, propylamino, isopropylamino, butylamino and tert-butylamino, di-(C₁–C₆-alkyl)amino is selected from dimethylamino, diethylamino, dipropylamino, diisopropylamino, isopropylmethylamino, dibutylamino and tert-butylmethylamino, C₁–C₆-acyl is selected from the group consisting of formyl, acetyl, propionyl, acryloyl, butyryl, isobutyryl, methacryloyl, cyclopropylcarbonyl, pentanoyl, pivaloyl, cyclobutylcarbonyl, hexanoyl and dimethylacryloyl, C₁–C₆-alkylsulfonyl is selected from the group consisting of methanesulfonyl, ethanesulfonyl, propanesulfonyl, butanesulfonyl, pentanesulfonyl and hexanesulfonyl, tautomeres in the case of substitution in an anellated ring system by free hydroxy-, mercapto- and/or amino groups, and cis/trans-isomers, endo/exo-isomers, enantiomers, diastereomers as pure isomers or mixtures and racemic mixtures as the pharmacologically acceptable salts, the salts being selected from the group consisting of hydrochlorides, hydrobromides, hydroiodides, sulfates phosphates, acetates, benzoates, 4-methoxybenzoate, 2- or 4-hydroxybenzoate, 4-chlorobenzoate, ascorbate, salicylate, formiate, glutarate, tricarballylate, citrates, fumarates, gluconates, malates, maleates, methanesulfonates, lactates, oxalates, succinates, tartrates and toluenesulfonates.

3. Compounds of formula (I) and pharmaceutically acceptable salts of formula (I)

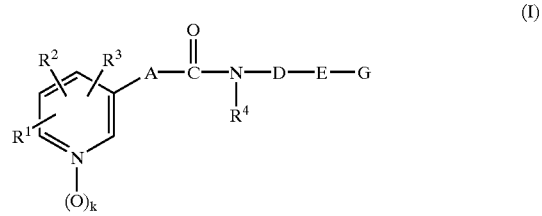

wherein

R¹ is selected from the group consisting of hydrogen, halogen, cyano, C₁–C₆-alkyl, trifluoromethyl, C₃–C₈-cycloalkyl, C₁–C₄-hydroxyalkyl, hydroxy, C₁–C₄-alkoxy, benzyloxy, C₁–C₄-alkanoyloxy, C₁–C₄-alkylthio, C₂–C₅-alkoxycarbonyl, aminocarbonyl, C₃–C₉-dialkylaminocarbonyl, carboxy, phenyl, phenoxy, NR⁵R⁶, and bridged R¹R², wherein R⁵ is selected from the group consisting of hydrogen and and C₁–C₆-alkyl and R⁶ is selected from the group consisting of hydrogen and C₁–C₆-alkyl, R² is selected from the group consisting of hydrogen, halogen, C₁–C₆-alkyl, trifluoromethyl, hydroxy, and bridged R¹R², wherein bridged R¹R² is where R¹R² are adjacent and form a bridge which is selected from the bridge members —(CH₂)₄— and —(CH=CH)₂— and —CH₂O—CR⁷R⁸—O—, wherein R⁷ is selected from the group consisting of hydrogen and C₁–C₆-alkyl and R⁸ is selected from the group consisting of hydrogen or C₁–C₆-alkyl, R³ is selected from the group consisting of hydrogen, halogen, and C₁–C₆-alkyl, R⁴ is selected from the group consisting of hydrogen, C₁–C₆-alkyl, C₃–C₆-alkenyl, hydroxy, C₁–C₆-alkoxy and benzyloxy, k is 0 or 1, A is selected from the group consisting of $C_1$–$C_6$-alkylene,
a substituted $C_1$–$C_6$-alkylene which is substituted once to three-fold by $C_1$–$C_3$-alkyl, hydroxy, fluorine or phenyl, 1,2-cyclopropylene and an isosterically substituted $C_2$–$C_6$-alkylene, wherein the isosterically substituted $C_2$–$C_6$ alkylene has a methylene unit which is isosterically replaced by O, S, $NR^9$, CO, SO or $SO_2$, and wherein the isosteric replacement, with the exception of =CO, is not adjacent to the amide group, and wherein $R^9$ is selected from the group consisting of hydrogen, $C_1$–$C_3$-alkyl, $C_1$–$C_6$-acyl and methanesulfonyl, D is selected from the group consisting of $C_1$–$C_{10}$-alkylene,
a substituted $C_1$–$C_{10}$-alkylene which is substituted once or twice by $C_1$–$C_3$-alkyl or hydroxy, a $C_2$–$C_{10}$-alkenylene, a $C_2$–$C_{10}$-alkenylene which is substituted once or twice by $C_1$–$C_3$-alkyl or hydroxy, an E double bonded $C_2$–$C_{10}$ alkenylene which has a double bond to ring E, an E double bonded substituted $C_2$–$C_{10}$-alkenylene which has a double bond to ring E, a $C_3$–$C_{10}$-alkinylene, a substituted $C_3$–$C_{10}$-alkinylene which is substituted once or twice by $C_1$–$C_3$-alkyl, hydroxy, and an isosterically replaced $C_1$–$C_{10}$-alkylene, $C_2$–$C_{10}$-alkenylene or $C_3$–$C_{10}$-alkinylene, having an isosterically replaced group having one to three methylene units which are each isosterically replaced by O, S, $NR^{10}$, CO, SO or $SO_2$, wherein $R^{10}$ has the same meaning as $R^9$, but is selected independently therefrom, E is

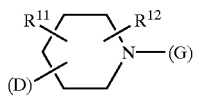

$R^{11}$ is selected from the group consisting of hydrogen, $C_1$–$C_3$-alkyl, hydroxy, hydroxymethyl, carboxy and $C_2$–$C_7$-alkoxycarbonyl, $R^{12}$ is selected from the group consisting of hydrogen an oxo group adjacent to the nitrogen atom, G is selected from the group consisting of hydrogen, G1, G2, G3, G4 and G5, wherein
G1 is

 (G1)

wherein
r is 0, 1 or 2 and
s is 0 or 1, $R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl, benzyl, phenyl, anellated bi- and tricyclic aromatic or partially hydrogenated carbocyclic ring systems with 8 to 16 ring atoms and at least one aromatic ring, whereby the bond occurs either over an aromatic or a hydrogenated ring and either directly or over a methylene group, $R^{14}$ has the same meaning as $R^{13}$, but is selected independently thereof, $R^{15}$ is selected from hydrogen, hydroxy, methyl, benzyl, phenyl, anellated bi- and tricyclic aromatic or partially hydrogenated carbocyclic ring systems with 8 to 16 ring atoms and at least one aromatic ring, wherein the bond occurs either over an aromatic or a hydrogenated ring and either directly or over a methylene group, G2 is

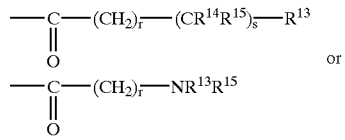

wherein the substituents $R^3$ and $R^{15}$ have the above meaning,

G3 is —$SO_2$—$(CH_2)_r R^{13}$

G4 is

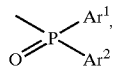

wherein
$Ar^1$ is selected from the group consisting of phenyl, and naphthyl,
$Ar^2$ is selected from the group consisting of phenyl, and naphthyl, and
G5 is —$COR^{16}$ (G5) wherein
$R^{16}$ is selected from the group consisting of trifluoromethyl, $C_1$–$C_6$-alkoxy, $C_3$–$C_6$-alkenyloxy, and benzyloxy, and wherein aromatic rings in the substituents $R^1$, $R^2$, $R^4$, $R^{13}$, $R^{14}$, $R^{15}$, $R^{16}$, $AR^1$ and $Ar^2$ are substituted or unsubstituted the substituted rings in $R^1$, $R^2$, $R^4$, $R^{13}$, $R^{14}$, $R^{15}$, $R^{16}$ $Ar^1$ and $Ar^2$ having one to three substituents which are independently selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-alkoxy, benzyloxy, phenoxy, mercapto, $C_1$–$C_6$-alkylthio, carboxy, $C_1$–$C_6$-alkoxycarbonyl, benzyloxycarbonyl, nitro, amino, mono-$C_1$–$C_6$-alkylamino, di-($C_1$–$C_6$-alkyl)-amino, and substituted $C_1$–$C_6$-alkoxy, wherein two adjacent groups on the aromatic ring may form an additional ring over a methylenedioxy bridge.

4. Compounds according to claim 3, wherein
$R^1$ is selected from the group consisting of hydrogen, halogen, cyano, methyl, trifluoromethyl, hydroxy, $C_1$–$C_4$-alkoxy, ethylthio, methoxycarbonyl, tert-butoxycarbonyl, aminocarbonyl, carboxy, and phenoxy,
$R^2$ is selected from the group consisting of hydrogen, halogen, trifluoromethyl and hydroxy,
$R^3$ is hydrogen or halogen,
$R^4$ is selected from the group consisting of hydrogen, $C_1$–$C_3$-alkyl, hydroxy and $C_1$–$C_3$-alkoxy,
A is selected from the group consisting of $C_2$–$C_6$-alkylene, a substituted $C_2$–$C_6$-alkylene which is substituted once or twice by $C_1$–$C_3$-alkyl, hydroxy or fluorine, and
an isosterically susbstituted $C_2$–$C_6$-alkylene, which has a methylene unit which is isosterically replaced by O, S, CO or $SO_2$, wherein the isosteric replacement, with the exception of CO is not adjacent to the amide group,
D is selected from the group consisting of $C_1$–$C_8$-alkylene, a substituted $C_1$–$C_8$-alkylene which is substituted once or twice by methyl or hydroxy,
$C_2$–$C_8$-alkenylene, a substituted $C_2$–$C_8$-alkenylene which is substituted once or twice by methyl or hydroxy, an E bonded $C_2$–$C_8$-alkylene which has a double bond to ring E, an E double bonded substituted $C_2$–$C_{10}$-alkenylene which has a double bond to ring E, $C_3$–$C_8$-alkinylene, a substituted $C_3$–$C_8$-alkinylene which is substituted once or twice by methyl or hydroxy, and an isosterically replaced $C_1$–$C_8$-alkylene, $C_2$–$C_8$-alkenylene and $C_3$–$C_8$-alkinylene, having an isosterically replaced group having one to three methylene units which are isosterically replaced by O, S, NH, N(CH$_3$), N(COCH$_3$), N(SO$_2$CH$_3$), CO, SO or SO$_2$, $R^{11}$ is selected from the group consisting of hydrogen, $C_1$–$C_3$-alkyl, hydroxy, and hydroxymethyl, $R^{12}$ is selected from the group consisting of hydrogen and an oxo group which is adjacent to the nitrogen atom, G is selected from the group consisting of hydrogen, G1, G2, G3, G4 and G5, wherein G1 is

     (G1)

wherein r is 0, 1 or 2 and s is 0 or 1, $R^{13}$ is selected from the group consisting of hydrogen, $C_1$–$C_6$-alkyl, $C_3$–$C_8$-cycloalkyl, benzyl, phenyl, benzocyclobutyl, indanyl, indenyl, oxoindanyl, naphthyl, dihydronaphthyl, tetrahydronaphthyl, oxotetrahydronaphthyl, biphenylenyl, fluorenyl, oxofluorenyl, anthryl, dihydroanthryl, oxodihydroanthryl, dioxodihydroanthryl, phenanthryl, dihydrophenanthryl, oxodihydrophenanthryl, dibenzocycloheptenyl, oxodibenzocycloheptenyl, dihydrodibenzocycloheptenyl, oxodihydrodibenzocycloheptenyl, dihydrodibenzocyclooctenyl, tetrahydrodibenzocyclooctenyl, and oxotetrahydrodibenzocyclooctenyl, bound directly or over a methylene group, $R^{14}$ has the same meaning as $R^{13}$, but is selected independently therefrom, $R^{15}$ is selected from the group consisting of hydrogen, hydroxy, methyl, benzyl, phenyl, indanyl, indenyl, naphthyl, dihydronaphthyl, and tetrahydronaphthyl.

5. Compounds according to claim 3, wherein $R^1$ is selected from the group consisting of hydrogen, halogen, cyano, methyl, trifluoromethyl, hydroxy, methoxy and methoxycarbonyl, $R^2$ is hydrogen or halogen, $R^3$ is hydrogen, $R^4$ is selected from the group consisting of hydrogen, $C_1$–$C_3$-alkyl and hydroxy, A is selected from the group consisting of $C_2$–$C_6$-alkylene, a substituted $C_2$–$C_6$-alkylene which is substituted once or twice by hydroxy or fluorine, and an isosterically substituted $C_2$–$C_6$-alkylene, which has a methylene unit which is isosterically replaced by O, S or CO, and the isosteric substitute, with the exception of CO, is not adjacent to the amide group and, D is selected from the group consisting of $C_2$–$C_8$-alkylene, a substituted $C_2$–$C_8$-alkylene which is substituted by methyl or hydroxy, a $C_2$–$C_8$-alkenylene, a substituted $C_2$–$C_8$-alkenylene which is substituted by methyl or hydroxy, an E double bonded $C_2$–$C_8$-alkenylene which has a double bond to ring E, an E double bonded substituted $C_2$–$C_8$-alkenylene which has a double bond to ring E, and an isosterically replaced $C_2$–$C_8$-alkylene, and $C_2$–$C_8$-alkenylene, having an isosterically replaced group having one to three methylene units which are isosterically replaced by O, NH, N(CH$_3$), N(COCH$_3$), N(SO$_2$CH$_3$) or CO, $R^{11}$ is selected from the group consisting of hydrogen, methyl and hydroxyl, $R^{12}$ is selected from the group consisting of hydrogen and an oxo group adjacent to the nitrogen atom, G is selected from the group consisting of hydrogen, $C_3$–$C_8$-cycloalkyl, methoxycarbonyl, tert-butoxycarbonyl, benzyloxycarbonyl, trifluoroacetyl, diphenylphosphinoyl,

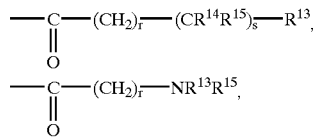

and

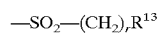

wherein r is 0, 1 or 2 and s is 0 or 1, $R^{13}$ is selected from the group consisting of hydrogen, methyl, benzyl, phenyl, indanyl, indenyl, oxoindanyl, naphthyl, dihydronaphthyl, tetrahydronaphthyl, oxotetrahydronaphthyl, fluorenyl, oxofluorenyl, anthryl, dihydroanthryl, oxodihydroanthryl, dioxodihydroanthryl, dibenzocycloheptenyl, oxodibenzocycloheptenyl, dihydrodibenzocycloheptenyl, and oxodihydrodibenzocycloheptenyl, wherein the linkage occurs either directly or over a methylene group, $R^{14}$ is selected from the group consisting of hydrogen, methyl, benzyl and phenyl, $R^{15}$ is selected from the group consisting of hydrogen, hydroxy, methyl, benzyl, phenyl, and napthyl.

6. Compounds according to claim 3, wherein $R^1$ is selected from the group consisting of hydrogen, fluorine, chlorine, bromine, methyl, trifluoromethyl and hydroxy, $R^2$ and $R^3$ are hydrogen, $R^4$ is hydrogen or hydroxy, k is 0 or 1, A is $C_2$–$C_6$-alkylene, or a substituted $C_2$–$C_6$-alkylene which is substituted once or twice by hydroxy or fluorine, D is selected from the group consisting of $C_2$–$C_6$-alkylene, $C_2$–$C_6$-alkenylene, an E double bonded $C_2$–$C_6$-alkenylene, which has a double bond to ring E, and the group consisting of $C_2$–$C_6$-alkylene and $C_2$–$C_6$-alkenylene, wherein a methylene unit is isosterically replaced by O, NH, N(CH$_3$) or CO, or an ethylene group is isosterically replaced by NH—CO or CO—NH or a propylene group is isosterically replaced by NH—CO—O or O—CO—NH, G is selected from the group consisting of hydrogen, tert-butoxycarbonyl, diphenylphosphinoyl, and

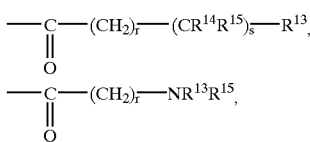

and

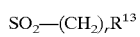

wherein
r is 0 or 1 and
s is 0 or 1,
R$^{13}$ is selected from the group consisting of hydrogen, methyl, benzyl, phenyl, indenyl, oxoindanyl, naphthyl, tetrahydronaphthyl, fluorenyl, oxofluorenyl, anthryl, dihydroanthryl, oxodihydroanthryl, dioxodihydroanthryl, dibenzocycloheptenyl, and dihydrodibenzocycloheptenyl, wherein the linkage occurs either directly or over a methylene group,
R$^{14}$ is selected from the group consisting of hydrogen, methyl, benzyl and phenyl,
R$^{15}$ is selected from the group consisting of hydrogen, hydroxy, methyl, benzyl, phenyl, and
wherein aromatic ring systems in the substituents are substituted, independently of each other, by one to three substituents which are independently selected from the group consisting of halogen, cyano, C$_1$–C$_6$-alkyl, trifluoromethyl, C$_3$–C$_8$-cycloalkyl, phenyl, benzyl, hydroxy, C$_1$–C$_6$-alkoxy, benzyloxy, phenoxy, mercapto, C$_1$–C$_6$-alkylthio, carboxy, C$_1$–C$_6$-alkoxycarbonyl, benzyloxycarbonyl, nitro, amino, mono-C$_1$–C$_6$-alkylamino, di-(C$_1$–C$_6$-alkyl)-amino, and substituted C$_1$–C$_6$-alkoxy, which are entirely or partially substituted by fluorine, whereby two adjacent groups on the aromatic ring may form an additional ring over a methylenedioxy bridge.

7. Compounds having a general formula (I) and pharmaceutically acceptable salts of formula (I)

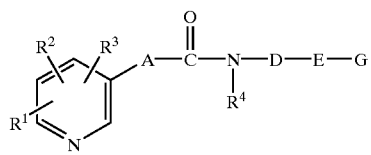

wherein
R$^1$ is selected from the group consisting of hydrogen, fluorine, methyl, trifluoromethyl and hydroxy,
R$^2$ and R$^3$ are hydrogen,
R$^4$ is hydrogen or hydroxy,
A is selected from the group consisting of ethylene, propylene, butylene, substituted ethylene substituted by hydroxy or one or two fluorine, substituted propylene substituted by hydroxy or one or two fluorine, and substituted butylene substituted by hydroxy or one or two fluorine,
D is selected from the group consisting of C$_2$–C$_6$-alkylene, C$_2$–C$_6$-alkenylene, an E double bonded C$_2$–C$_6$-alkylene which has a double bond to ring E,
E is piperidine,
G is selected from the group consisting of benzyl, phenethyl, fluorenylmethyl, anthrylmethyl, diphenylmethyl, fluorenyl, dihydrodibenzocycloheptenyl, acetyl, pivaloyl, phenylacetyl, diphenylacetyl, diphenylpropionyl, naphthylacetyl, benzoyl, naphthoyl, anthrylcarbonyl, oxofluorenylcarbonyl, oxodihydroanthrylcarbonyl, dioxodihydroanthrylcarbonyl, naphthylsulfonyl, and diphenylphosphinoyl,
wherein aromatic rings in G may be substituted independently of each other by one to three substituents which are independently selected from the group consisting of halogen, cyano, C$_1$–C$_6$-alkyl, trifluoromethyl, C$_3$–C$_6$-cycloalkyl, phenyl, benzyl, hydroxy, C$_1$–C$_6$-alkoxy, benzyloxy, phenoxy, mercapto, C$_1$–C$_6$-alkylthio, carboxy, C$_1$–C$_6$-alkoxycarbonyl, benzyloxycarbonyl, nitro, amino, mono-C$_1$–C$_6$-alkylamino, di-(C$_1$–C$_6$-alkyl)-amino, substituted C$_1$–C$_6$-alkoxy which is entirely or partially substituted by fluorine, wherein two adjacent groups in the ring may form an additional ring over a methylenedioxy bridge.

8. Compound according to claim 3 wherein it is present in the form of N-[4-(1-acetyl-piperidin-4-yl)-butyl]-3-(pyridin-3-yl)-propionamide, N-[4-(1-benzoyl-piperidin-4-yl)-butyl]-3-(pyridin-3-yl)-propionamide, N-[4-(1-diphenylacetyl-piperidin-4-yl)-butyl]-3-(pyridin-3-yl)-propionamide, N-{4-[1-(9-oxo-9H-fluoren-4-carbonyl)-piperidin-4-yl]-butyl}-3-(pyridin-3-yl)-propionamide, N-[4-(1-methylsulfonyl-piperidin-4-yl)-butyl]-3-(pyridin-3-yl)-propionamide or N-{4-[1-(2-naphthylsulfonyl)-piperidin-4-yl]-butyl}-3-(pyridin-3-yl)-propionamide, and/or as a pharmaceutically acceptable salt thereof.

9. Compound according to claim 3, wherein it is present in the form of N-[4-(1-benzylpiperidin-4-yl)-butyl]-3-(pyridin-3-yl)-propionamide, N-(4-{1-[bis-(2-chlorophenyl)-methyl]-piperidin-4-yl}-butyl)-3-(pyridin-3-yl)-propionamide, N-{4-[1-(phenylpyridin-3-yl-methyl)-piperidin-4-yl]-butyl}-3-(pyridin-3-yl)-propionamide, N-(4-[1-(9H-fluoren-9-yl)-piperidin-4-yl]-butyl}-3-(pyridin-3-yl)-propionamide and/or as a pharmaceutically acceptable salt thereof.

10. Compound according to claim 3, wherein it is present in the form of N-{4-[1-(1-naphthylaminocarbonyl)-piperidin-4-yl]-butyl}-3-(pyridin-3-yl)-propionamide, N-[4-(1-diphenylaminocarbonyl-piperidin-4-yl)-butyl]-3-(pyridin-3-yl)-propionamide, or N-[4-(1-diphenylphosphinoyl-piperidin-4-yl)-butyl]-3-(pyridin-3-yl)-propionamide, and/or as a pharmaceutically acceptable salt thereof.

11. Compound according to claim 3, wherein it is present in the form of N-[4-(1-diphenylmethyl-piperidin-4-yl)-butyl]-3-(2-fluoropyridin-3-yl)-propionamide, N-[4-(1-diphenylmethyl-piperidin-4-yl)-butyl]-3-(5-fluoropyridin-3-yl)-propionamide, N-[4-(1-diphenylmethyl-piperidin-4-yl)-butyl]-2-fluoro-3-(pyridin-3-yl)-propionamide or N-[4-(1-diphenylmethyl-piperidin-4-yl)-butyl]-2,2-difluoro-3-(pyridin-3-yl)-propionamide, and/or as a pharmaceutically acceptable salt thereof.

12. Compound according to one of the 3, wherein it is present in the form of N-[5-(1-diphenylmethyl-piperidin-4-yl)-pentyl]-3-(pyridin-3-yl)-propionamide, N-[6-(1-diphenylmethyl-piperidin-4-yl)-hexyl]-3-(pyridin-3-yl)-propionamide, N-[2-(1-diphenylmethyl-piperidin-4-yl)-ethyl]-5-(pyridin-3-yl)-pentanoic acid amide, N-[4-(1-diphenylmethyl-piperidin-4-yl)-butyl]-3-(pyridin-3-yl)-propionamide, or N-[4-(1-diphenylmethyl-piperidin-4-yl)-butyl]-5-(pyridin-3-yl)-pentanoic acid amide, and/or as a pharmaceutically acceptable salt thereof.

13. Compound according to claim 3, wherein it is present in the form of N-[4-(1-diphenylmethylpiperidin-4-yl)-butyl]-N-hydroxy-3-(pyridin-3-yl)-propionamide, N-[4-(1- diphenylmethylpiperidin-4-yl)-butyl]-2-hydroxy-3-(pyridin-3-yl)-propionamide or N-[4-(1-diphenylmethyl-piperidin-4-yl)-butyl]-3-hydroxy-3-(pyridin-3-yl)-propionamide, and/or as a pharmaceutically acceptable salt thereof.

14. A method for the production of compounds having general formula (I)

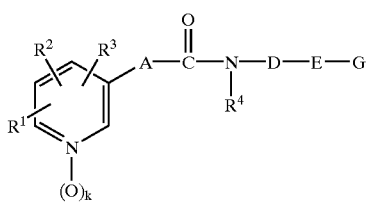

(I)

the method comprising:
reacting a carboxylic acids of formula (II)

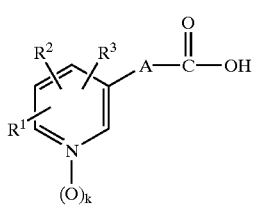

(II)

with compounds of formula (III)

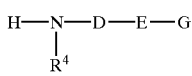

(III)

wherein
$R^1$ is selected from the group consisting of hydrogen, halogen, cyano, $C_1$–$C_6$-alkyl, $C_3$–$C_6$-alkenyl, $C_3$–$C_6$-alkinyl, trifluoromethyl, $C_3$–$C_8$cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, $NR^5R^6$, and bridged $R^1R^2$ wherein
$R^5$ is selected from the group consisting of hydrogen, $C_1$–$C_6$-alkyl, $C_3$–$C_6$-alkenyl and $C_3$–$C_6$-alkinyl,
$R^6$ is selected from the group consisting of hydrogen, $C_1$–$C_6$-alkyl, $C_3$–$C_6$-alkenyl and $C_3$–$C_6$-alkinyl,
$R^2$ is selected from the group consisting of hydrogen, halogen, cyano, $C_1$–$C_6$-alkyl, trifluoromethyl, hydroxy, $C_1$–$C_6$-alkoxy, benzyloxy, $C_1$–$C_7$-alkanoyloxy, and bridged $R^1R^2$;
wherein bridged $R^1R^2$ is where $R^1R^2$ are adjacent and form a bridge which is selected from the group consisting of —(CH$_2$)$_4$— and —(CH=CH)$_2$— and —CH$_2$O—CR$^7$R$^8$—O—, wherein
$R^7$ is selected from the group consisting of hydrogen and $C_1$–$C_6$-alkyl and
$R^8$ is selected from the group consisting of hydrogen and $C_1$–$C_6$-alkyl,
$R^3$ is selected from the group consisting of hydrogen, halogen, $C_1$–$C_6$-alkyl, trifluoromethyl and $C_1$–$C_6$-hydroxyalkyl;

$R^4$ is selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;
k is 0 or 1,
A is selected from the group consisting of $C_1$–$C_6$-alkylene, a substituted $C_1$–$C_6$-alkylene which is substituted once to three-fold by $C_1$–$C_3$-alkyl, hydroxy, $C_1$–$C_3$-alkoxy, fluorine or phenyl,
a 1,2-cyclopropylene and an isosterically substituted $C_2$–$C_6$-alkylene, which has a methylene unit which is isosterically replaced by O, S, $NR^9$, CO, SO or SO$_2$, wherein the isosteric replacement, with the exception of CO, is not adjacent to the amide group, and wherein $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkylsulfonyl,
D is selected from the group consisting of $C_1$–$C_{10}$-alkylene, a substituted $C_1$–$C_{10}$-alkylene which is substituted once or twice by $C_1$–$C_6$-alkyl, hydroxy, or $C_1$–$C_6$-alkoxy,
a $C_2$–$C_{10}$-alkenylene, a substituted $C_2$–$C_{10}$-alkenylene which is substituted once or twice by $C_1$–$C_6$-alkyl, hydroxy, $C_1$–$C_6$-alkoxy,
an E double bonded $C_2$–$C_{10}$-alkenylene which has a double bond to ring E,
an E double bonded substituted $C_2$–$C_{10}$-alkenylene which has a double bond to ring E,
a $C_3$–$C_{10}$-alkinylene, a substituted $C_3$–$C_{10}$-alkinylene which is substituted once or twice by $C_1$–$C_6$-alkyl, hydroxy, or $C_1$–$C_6$-alkoxy, and
an isosterically replaced $C_1$–$C_{10}$-alkylene, $C_2$–$C_{10}$-alkenylene or $C_3$–$C_{10}$-alkinylene having an isosterically replaced group having one to three methylene units are each isosterically replaced by O, S, $NR^{10}$, CO, SO or SO$_2$, wherein
$R^{10}$ has the same meaning as $R^9$, but is selected independently therefrom,
E is

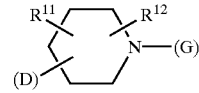

$R^{11}$ is selected from the group consisting of hydrogen, $C_1$–$C_6$-alkyl, hydroxy, hydroxymethyl, carboxy and $C_2$–$C_7$-alkoxycarbonyl, and
$R^{12}$ is selected from the group consisting of hydrogen, $C_1$–$C_6$-alkyl and an oxo group adjacent to the nitrogen atom, or
$R^{11}$ and $R^{12}$ together form a $C_1$–$C_3$-alkylene bridge under formation of a bi-cyclic ring system,
G is selected from the group consisting of hydrogen, G1, G2, G3, G4 and G5, wherein
G1 is

wherein
r is an integer from 1 to 3 or 0,
s is 0 or 1,
$R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl, benzyl, phenyl, anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group, R$^{14}$ has the same meaning as R$^{13}$, but is selected independently thereof, R$^{15}$ is selected from the group consisting of hydrogen, hydroxy, methyl, benzyl, phenyl, anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group, G2 is selected from the group consisting of

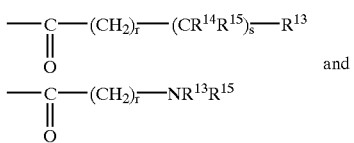

and wherein the substituents R$^3$ and R$^{15}$ have the above meaning,

G3 is SO$_2$—(CH$_2$)$_r$R$^{13}$ and
G4 is wherein

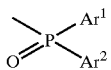

Ar$^1$ is selected from the group consisting of phenyl, and naphthyl, Ar$^2$ is selected from the group consisting of phenyl, and naphthyl, and G5 is —COR$^{16}$ wherein R$^{16}$ is selected from the group consisting of trifluoromethyl, C$_1$–C$_6$-alkoxy, C$_3$–C$_6$-alkenyloxy, and benzyloxy, and wherein aromatic rings in the substituents R$^1$, R$^2$, R$^4$, R$^{13}$, R$^{14}$, R$^{15}$, R$^{16}$, AR$^1$ and Ar$^2$ are substituted and unsubstituted the substituted rings in R$^1$, R$^2$, R$^4$, R$^{13}$, R$^{14}$, R$^{15}$, R$^{16}$, AR$^1$ and Ar$^2$ having substitutents which are independently selected from halogen, cyano, C$_1$–C$_6$-alkyl, trifluoromethyl, C$_3$–C$_8$-cycloalkyl, phenyl, benzyl, hydroxy, C$_1$–C$_6$-alkoxy, benzyloxy, phenoxy, mercapto, C$_1$–C$_6$-alkylthio, carboxy, C$_1$–C$_6$-alkoxycarbonyl, benzyloxycarbonyl, nitro, amino, mono-C$_1$–C$_6$-alkylamino, di-(C$_1$–C$_6$-alkyl)-amino, and substituted C$_1$–C$_6$ alkoxy which is entirely or partially substituted by fluorine, wherein two adjacent groups on the aromatic ring may form an additional ring over a methylenedioxy bridge.

15. Compounds of formula (I) and pharmaceutically acceptable salts of formula (I)

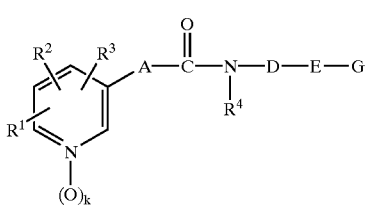

(I)

wherein
R$^1$ is selected from the group consisting of hydrogen, halogen, cyano, C$_1$–C$_6$-alkyl, C$_3$–C$_6$-alkenyl, C$_3$–C$_6$-alkinyl, trifluoromethyl, C$_3$–C$_8$-cycloalkyl, C$_1$–C$_6$-hydroxyalkyl, hydroxy, C$_1$–C$_6$-alkoxy, C$_3$–C$_6$-alkenyloxy, C$_3$–C$_6$-alkinyloxy, benzyloxy, C$_2$–C$_7$-alkanoyloxy, C$_2$–C$_7$-alkoxycarbonyloxy, C$_1$–C$_6$-alkylthio, C$_3$–C$_6$-alkenylthio, C$_3$–C$_6$-alkinylthio, C$_3$–C$_8$-cycloalkyloxy, C$_3$–C$_8$-cycloalkylthio, C$_2$–C$_7$-alkoxycarbonyl, aminocarbonyl, C$_2$–C$_7$-alkylaminocarbonyl, C$_3$–C$_{13}$-dialkylaminocarbonyl, carboxy, phenyl, phenoxy, phenylthio, NR$^5$R$^6{}_1$ and bridged R$^1$R$^2$ wherein R$^5$ is selected from the group consisting of hydrogen, C$_1$–C$_6$-alkyl, C$_3$–C$_6$-alkenyl and C$_3$–C$_6$-alkinyl, R$^6$ is selected from the group consisting of hydrogen, C$_1$–C$_6$-alkyl, C$_3$–C$_6$-alkenyl and C$_3$–C$_6$-alkinyl, R$^2$ is selected from the group consisting of hydrogen, halogen, cyano, C$_1$–C$_6$-alkyl, trifluoromethyl, hydroxy, C$_1$–C$_6$-alkoxy, benzyloxy, C$_1$–C$_7$-alkanoyloxy, and bridged R$^1$R$^2$;

wherein bridged R$^1$R$^2$ is where R$^1$R$^2$ are adjacent and form a bridge which is selected from the group consisting of —(CH$_2$)$_4$— and —(CH=CH)$_2$— and —CH$_2$O—CR$^7$R$^8$—O—, wherein R$^7$ is selected from the group consisting of hydrogen and C$_1$–C$_6$-alkyl and R$^8$ is selected from the group consisting of hydrogen and C$_1$–C$_6$-alkyl, R$^3$ is selected from the group consisting of hydrogen, halogen, C$_1$–C$_6$-alkyl, trifluoromethyl and C$_1$–C$_6$-hydroxyalkyl;

R$^4$ is selected from the group consisting of hydrogen, C$_1$–C$_6$-alkyl, C$_3$–C$_6$-alkenyl, C$_3$–C$_6$-alkinyl, C$_3$–C$_6$-cycloalkyl, hydroxy, C$_1$–C$_{10}$-alkoxy and benzyloxy;

k is 0 or 1,

A is selected from the group consisting of C$_1$–C$_6$-alkylene, a substituted C$_1$–C$_6$-alkylene which is substituted once to three-fold by C$_1$–C$_3$-alkyl, hydroxy, C$_1$–C$_3$-alkoxy, fluorine or phenyl, a 1,2-cyclopropylene and an isosterically substituted C$_2$–C$_6$-alkylene, which has a methylene unit which is isosterically replaced by O, S, NR$^9$, CO, SO or SO$_2$, wherein the isosteric replacement, with the exception of =CO, is not adjacent to the amide group, and wherein R$^9$ is selected from the group consisting of hydrogen, C$_1$–C$_6$-alkyl, C$_3$–C$_6$-alkenyl, C$_3$–C$_6$-alkinyl, C$_1$–C$_6$-acyl and C$_1$–C$_6$-alkylsulfonyl, wherein DEG is selected from the group consisting of

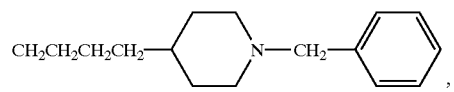

,

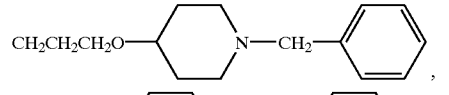

,

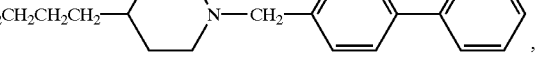

,

155
-continued
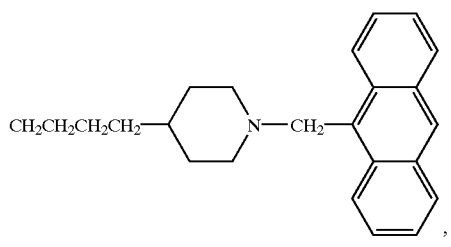
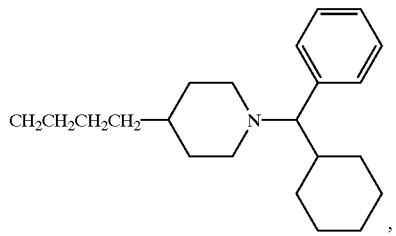
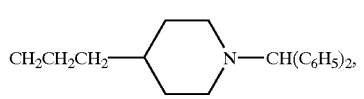
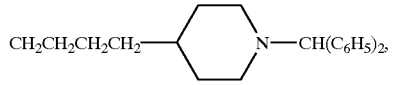
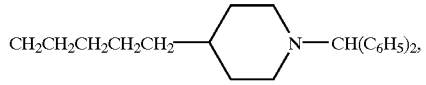
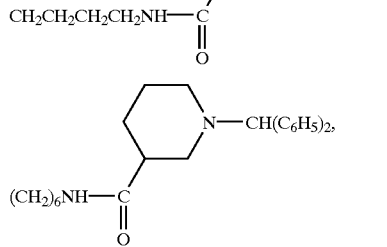
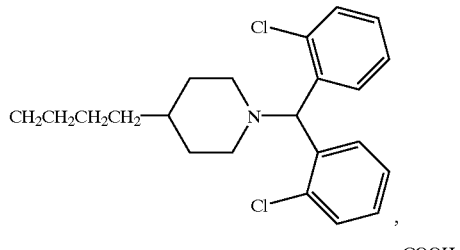
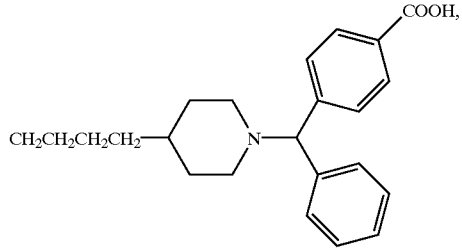
156
-continued
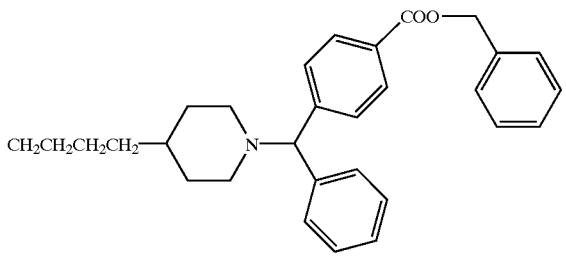
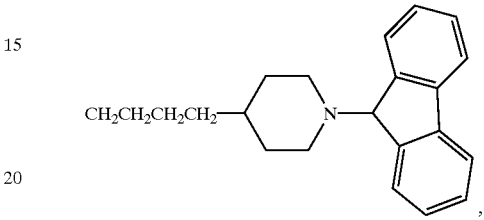
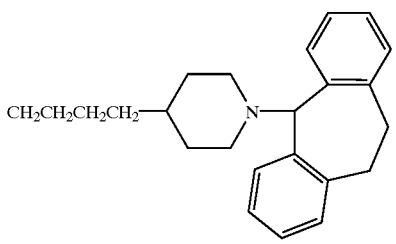
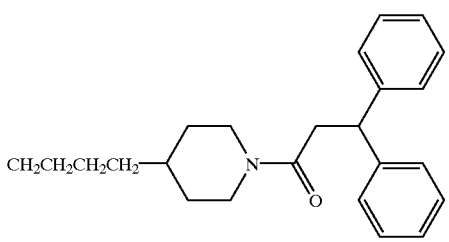
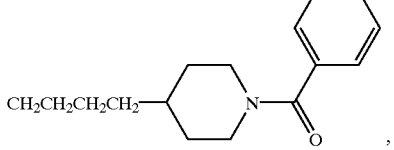
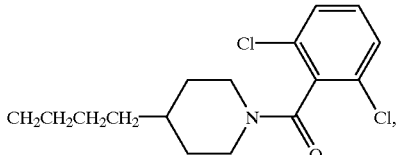
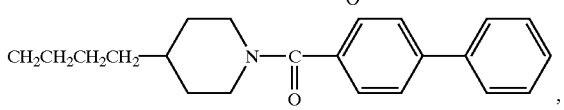
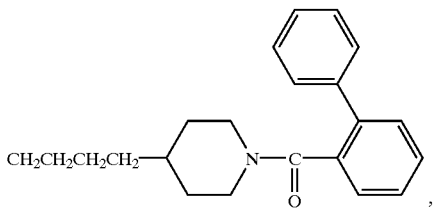

-continued
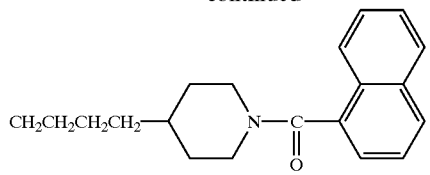
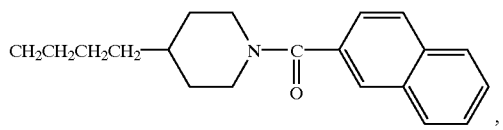
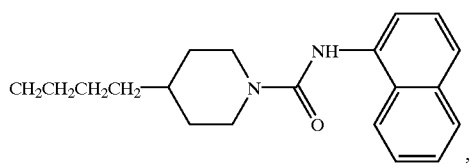
-continued
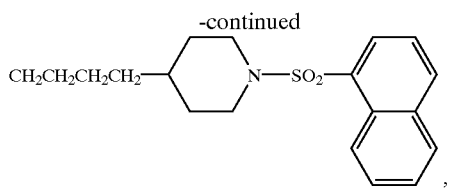
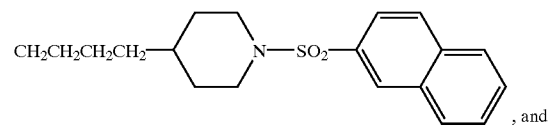
, and
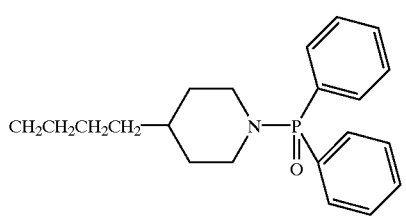
.
* * * * *